United States Patent
Paras et al.

(10) Patent No.: US 8,735,384 B2
(45) Date of Patent: May 27, 2014

(54) AMINO HETEROARYL COMPOUNDS AS BETA-SECRETASE MODULATORS AND METHODS OF USE

(75) Inventors: Nick A. Paras, San Francisco, CA (US); James Brown, Moorpark, CA (US); Yuan Cheng, Newbury Park, CA (US); Stephen A. Hitchcock, Jupiter, FL (US); Ted Judd, Granada Hills, CA (US); Patricia Lopez, West Hills, CA (US); Ana Elena Minatti, Santa Monica, CA (US); Thomas Nixey, Newbury Park, CA (US); Timothy Powers, Malibu, CA (US); Christopher M. Tegley, Thousand Oaks, CA (US); Qiufen Xue, Newbury Park, CA (US); Bryant Yang, Simi Valley, CA (US); Wenge Zhong, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/522,823

(22) PCT Filed: Jan. 14, 2011

(86) PCT No.: PCT/US2011/021423
§ 371 (c)(1),
(2), (4) Date: Oct. 2, 2012

(87) PCT Pub. No.: WO2011/090911
PCT Pub. Date: Jul. 28, 2011

(65) Prior Publication Data
US 2013/0040931 A1    Feb. 14, 2013

Related U.S. Application Data

(60) Provisional application No. 61/296,416, filed on Jan. 19, 2010.

(51) Int. Cl.
*A61K 31/535* (2006.01)
*A01N 57/00* (2006.01)
*A61K 31/675* (2006.01)

(52) U.S. Cl.
USPC ............ 514/210.18; 514/231.2; 514/80

(58) Field of Classification Search
None
See application file for complete search history.

(56) References Cited

U.S. PATENT DOCUMENTS

| | | |
|---|---|---|
| 5,441,870 A | 8/1995 | Seubert et al. |
| 5,712,130 A | 1/1998 | Hajko et al. |
| 5,942,400 A | 8/1999 | Anderson et al. |
| 2010/0041698 A1 | 2/2010 | Amberg et al. |

FOREIGN PATENT DOCUMENTS

| | | |
|---|---|---|
| WF | 2007092846 A2 | 8/2007 |
| WO | 2005009969 A1 | 2/2005 |
| WO | 2007022946 A1 | 3/2007 |
| WO | 2007092854 A2 | 8/2007 |
| WO | 2009097278 A1 | 8/2009 |
| WO | 2009097401 A1 | 8/2009 |

OTHER PUBLICATIONS

CAS RN: 582293-02-5 (entered STN Sep. 10, 2003).*
Sabbagh, M. et al., *Alz. Dis. Rev.* 3:1-19 (1997).
Cole, S.L., Vasser, R., *Molecular Degeneration* 2:22, 2007.
Luo et al., *Nature Neuroscience*, 4:231-232 (2001).
*Bulletin of Experimental Biology and Medicine* 129 (6): 544-546).
IPRP PCT/US2011/021423.
Joachim et al., *Alz. Dis. Assoc. Dis.*, 6:7-34 (1992).
Selkoe, *Neuron*, 6:487 (1991).
Seubert et al., *Nature*, 359:325-327 (1992).
Citron, Trends in Pharmacological Sciences, 25(2):92-97 (2004).
Shnakar, G.M., *Nature Medicine* (Jun. 22, 2008) online doi 10:1038 nm 1782.
Sinha et al., *Nature*, 402:537-554 (1999) (p510).

* cited by examiner

*Primary Examiner* — Craig Ricci
*Assistant Examiner* — Jared D Barsky
(74) *Attorney, Agent, or Firm* — G. Prabhakar Reddy

(57) ABSTRACT

The present invention comprises a new class of compounds useful for the modulation of Beta-secretase enzyme activity and for the treatment of Beta-secretase mediated diseases, including Alzheimer's disease (AD) and related conditions. In one embodiment, the compounds have a general Formula (I); wherein ring A, $B^1$, $B^2$, $B^3$, L, $R^1$, $R^2$, ring Z, m and n of Formula I are defined herein. The invention also includes use of these compounds in pharmaceutical compositions for treatment, prophylactic or therapeutic, of disorders and conditions related to the activity of beta-secretase protein. Such disorders include, for example, Alzheimer's Disease (AD), cognitive deficits, cognitive impairment, schizophrenia and other central nervous system conditions related to and/or caused by the formation and/or deposition of plaque on the brain. The invention also comprises further embodiments of Formula (I), intermediates and processes useful for the preparation of compounds of Formula (I).

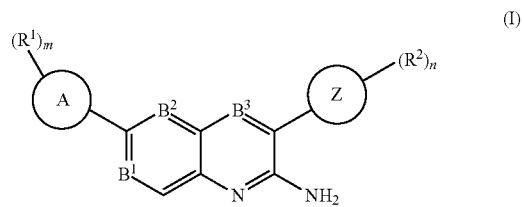

3 Claims, No Drawings

AMINO HETEROARYL COMPOUNDS AS BETA-SECRETASE MODULATORS AND METHODS OF USE

RELATED APPLICATIONS

This application is a national stage application under 35 U.S.C. §371 of International Application No. PCT/US2011/021423, having an international filing date of Jan. 14, 2011, which claims the benefit of, and priority to, U.S. Provisional Patent Application No. 61/296,416, filed on Jan. 19, 2010, which is hereby incorporated herein by reference in its entirety.

FIELD OF THE INVENTION

The invention relates generally to new compounds, pharmaceutical compositions and methods of use thereof, to treat Beta-Secretase mediated diseases and conditions, including, without limitation, Alzheimer's disease, plaque formation in the brain as well as in the peripheral central nervous system and disorders related thereto.

BACKGROUND OF THE INVENTION

Alzheimer's disease (AD) affects greater than 12 million aging people worldwide. AD accounts for the majority of dementia clinically diagnosed after the age of 60. AD is generally characterized by the progressive decline of memory, reasoning, judgement and orientation. As the disease progresses, motor, sensory, and vocal abilities are affected until there is global impairment of multiple cognitive functions. The loss of cognitive function occurs gradually, typically leading to a diminished cognition of self, family and friends. Patients with severe cognitive impairment and/or diagnosed as end-stage AD are generally bedridden, incontinent, and dependent on custodial care. The AD patient eventually dies in about nine to ten years, on average, after initial diagnosis. Due to the incapacitating, generally humiliating and ultimately fatal effects of AD, there is a need to effectively treat AD upon diagnosis.

AD is characterized by two major physiological changes in the brain. The first change, beta amyloid plaque formation, supports the "amyloid cascade hypothesis" which conveys the thought that AD is caused by the formation of characteristic beta amyloid peptide (A-beta), or A-beta fragments thereof, deposits in the brain (commonly referred to as beta amyloid "plaques" or "plaque deposits") and in cerebral blood vessels (beta amyloid angiopathy). A wealth of evidence suggests that beta-amyloid and accompanying amyloid plaque formation is central to the pathophysiology of AD and is likely to play an early role in this intractable neurodegenerative disorder. The second change in AD is the formation of intraneuronal tangles, consisting of an aggregate form of the protein tau. Besides being found in patients with AD, intraneuronal tangles are also found in other dementia-inducing disorders. Joachim et al., *Alz. Dis. Assoc. Dis.*, 6:7-34 (1992).

Several lines of evidence indicate that progressive cerebral deposition of A-beta plays a seminal role in the pathogenisis of AD and can precede cognitive symptoms by years or even decades. Selkoe, *Neuron*, 6:487 (1991). Release of A-beta from neuronal cells grown in culture and the presence of A-beta in cerebrospinal fluid (CSF) of both normal individuals and AD patients has been demonstrated. Seubert et al., *Nature*, 359:325-327 (1992). Autopsies of AD patients have revealed large numbers of lesions comprising these 2 factors in areas of the human brain believed to be important for memory and cognition.

Smaller numbers of these lesions in a more restricted anatomical distribution are found in the brains of most aged humans who do not have clinical AD. Amyloid containing plaques and vascular amyloid angiopathy were also found in the brains of individuals with Down's Syndrome, Hereditary Cerebral Hemorrhage with Amyloidosis of the Dutch-type (HCHWA-D), and other neurodegenerative disorders.

It has been hypothesized that A-beta formation is a causative precursor or factor in the development of AD. More specifically, deposition of A-beta in areas of the brain responsible for cognitive factors is believed to be a major factor in the development of AD. Beta amyloid plaques are primarily composed of amyloid beta peptide (A-beta peptide). A-beta peptide is derived from the proteolytic cleavage of a large transmembrane amyloid precursor protein (APP), and is a peptide ranging in about 39-42 amino acid residues. A-beta 42 (42 amino acids long) is thought to be the major component of these plaque deposits in the brains of Alzheimer's Disease patients. Citron, *Trends in Pharmacological Sciences*, 25 (2):92-97 (2004).

Similar plaques appear in some variants of Lewy body dementia and in inclusion body myositis, a muscle disease. Aβ also forms aggregates coating cerebral blood vessels in cerebral amyloid angiopathy. These plaques are composed of a tangle of regularly ordered fibrillar aggregates called amyloid fibers, a protein fold shared by other peptides such as prions associated with protein misfolding diseases. Research on laboratory rats suggest that the two-molecule, soluble form of the peptide is a causative agent in the development of Alzheimer's and that the two-molecule form is the smallest synaptotoxic species of soluble amyloid beta oligomer. Shnakar, G. M., *Nature Medicine* (Jun. 22, 2008) online doi 10:1038 nm 1782.

Several aspartyl proteases are thought to be involved in the processing or cleavage of APP, resulting in the formation of A-beta peptide. Beta secretase (BACE, also commonly referred to as memapsin) is thought to first cleave APP to generate two fragments: (1) a first N-terminus fragment (beta APP) and (2) a second C-99 fragment, which is subsequently cleaved by gamma secretase to generate the A-beta peptide. APP has also found to be cleaved by alpha-secretase to produce alpha-sAPP, a secreted form of APP that does not result in beta-amyloid plaque formation. This alternate pathway precludes the formation of A-beta peptide. A description of the proteolytic processing fragments of APP is found, for example, in U.S. Pat. Nos. 5,441,870, 5,712,130 and 5,942,400.

BACE is an aspartyl protease enzyme comprising 501 amino acids and responsible for processing APP at the beta-secretase specific cleavage site. BACE is present in two forms, BACE 1 and BACE 2, designated as such depending upon the specific cleavage site of APP. Beta secretase is described in Sinha et al., *Nature*, 402:537-554 (1999) (p510) and PCT application WO 2000/17369. It has been proposed that A-beta peptide accumulates as a result of APP processing by BACE. Moreover, in vivo processing of APP at the beta secretase cleavage site is thought to be a rate-limiting step in A-beta production. Sabbagh, M. et al., *Alz. Dis. Rev.* 3:1-19 (1997). Thus, inhibition of the BACE enzyme activity is desirable for the treatment of AD.

Studies have shown that the inhibition of BACE may be linked to the treatment of AD. The BACE enzyme is essential for the generation of beta-amyloid or A-beta. BACE knockout mice do not produce beta-amyloid and are free from Alzheimer's associated pathologies including neuronal loss and certain memory deficits. Cole, S. L., Vasser, R., *Molecular Degeneration* 2:22, 2007. When crossed with transgenic mice that over express APP, the progeny of BACE deficient mice show reduced amounts of A-beta in brain extracts as compares with control animals (Luo et al., *Nature Neuroscience*, 4:231-232 (2001)). The fact that BACE initiates the formation of beta-amyloid, and the observation that BACE levels are elevated in this disease provide direct and compelling reasons to develop therapies directed at BACE inhibition thus reducing beta-amyloid and its associated toxicities.

Recently dimebolin has attracted renewed interest after being shown to have positive effects on persons suffering from Alzheimer's disease. Animal studies showing potential beneficial effects on Alzheimer's disease models were shown in Russian research in 2000 (Lermontova N N, Lukoyanov N V, Serkova T P, Lukoyanova E A, Bachurin S O (June 2000). "Dimebon improves learning in animals with experimental Alzheimer's disease". *Bulletin of Experimental Biology and Medicine* 129 (6): 544-546). Preliminary results from human trials have also been promising. In an initial six-month phase II trial, results have shown that at 12 months there was significant improvement over placebo. Dimebolin appears to operate through multiple mechanisms of action, both blocking the action of neurotoxic beta amyloid proteins and inhibiting L-type calcium channels modulating the action of AMPA and NMDA glutamate receptors. To this end, inhibition of cleavage or fragmentation of beta amyloid protein via the beta secretase pathway may provide a therapeutic method for treating AD and other beta amyloid or plaque related disorders.

Several approaches have been taken to potentially treat AD and plaque-related disorders. One approach has been to attempt to reduce the formation of plaque on the brain, by inhibiting or reducing the activity of BACE. For example, each of the following PCT publications: WO 03/045913, WO 04/043916, WO 03/002122, WO 03/006021, WO 03/002518, WO 04/024081, WO 03/040096, WO 04/050619, WO 04/080376, WO 04/099376, WO 05/004802, WO 04/080459, WO 04/062625, WO 04/042910, WO 05/004803, WO 05/005374, WO 03/106405, WO 03/062209, WO 03/030886, WO 02/002505, WO 01/070671, WO 03/057721, WO 03/006013, WO 03/037325, WO 04/094384, WO 04/094413, WO 03/006423, WO 03/050073, WO 03/029169 and WO 04/000821, describe inhibitors of BACE, potentially useful for treating AD and other beta-secretase mediated disorders. Despite these efforts, there is always a need to find new compounds which may effectively treat such plaque-related conditions and disorders, such as AD.

BRIEF DESCRIPTION OF THE INVENTION

The present invention provides a new class of compounds useful for the modulation of beta secretase activity. To that end, the compounds of the invention are useful for the regulation or reduction of the formation of A-beta peptide and, consequently, the regulation and/or reduction of beta amyloid plaque formation on the brain. Accordingly, the compounds are useful for the treatment of Alzheimer's disease and other beta secretase and/or plaque mediated disorders. For example, the compounds are useful for the prophylaxis and/or treatment, acute and/or chronic, of AD and other diseases or conditions involving the deposition or accumulation of beta amyloid peptide, and formation of plaque, on the brain.

The compounds provided by the invention, including stereoisomers, tautomers, solvates, pharmaceutically acceptable salts, derivatives or prodrugs thereof, are generally defined by Formula I

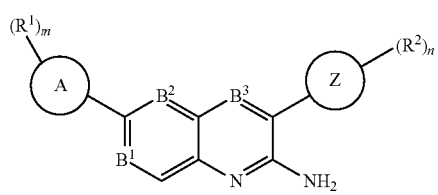

wherein ring A, $B^1$, $B^2$, $B^3$, L, $R^1$, $R^2$, ring Z, m and n of Formula I are defined herein below. The invention also provides compounds of sub-formulas of Formula I, as well as procedures for making compounds of Formula I and intermediates useful in such procedures.

The invention further provides pharmaceutical compositions, which comprise one or more compounds of the invention, methods for the treatment of beta secretase mediated diseases, such as AD, using the compounds and compositions of the invention. For example, and in one embodiment, the invention provides a pharmaceutical composition comprising an effective dosage amount of a compound of Formula I in association with at least one pharmaceutically acceptable excipient.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In one embodiment of the invention, the compounds, including stereoisomers, tautomers or pharmaceutically acceptable salts thereof, are generally defined by Formula I

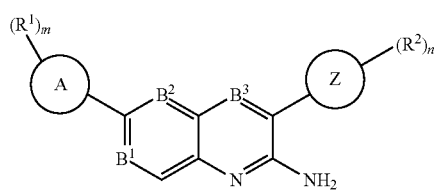

wherein
A is a 5- or 6-membered aryl or heteraryl ring;
each of $B^1$, $B^2$ and $B^3$, independently, is N, —CF, —CCH$_3$ or CH;
each $R^1$, independently, is halo, haloalkyl, CN, OH, NO$_2$, NH$_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-di-alkylamino-, $C_{1-10}$-alkoxyl, $C_{1-10}$-thioalkoxyl, —C(O)C$_{1-6}$-alkyl, —C(O)-cycloalkyl, —C(=N—OH)—$R^3$, —C(=N—OCH$_3$)—$R^3$, —C(O)OR$^3$ or C(O)NR$^a$R$^b$ wherein R$^a$ is H or $C_{1-6}$alkyl and R$^b$ is R$^3$, alternatively, R$^a$ and R$^b$ taken together with the nitrogen atom to which they are attached form a 4-7 membered monocyclic heterocycle, optionally substituted with 1-3 substituents of R$^3$; or $R^1$ is a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^3$;

each $R^2$ independently, is halo, haloalkyl, haloalkoxyl, CN, $NO_2$, $NH_2$, OH, oxo, $C_{1-6}$-alkyl, $-OC_{1-6}$-alkyl, $-S(O)_n$ $C_{1-6}$-alkyl, $-NHC_{1-6}$-alkyl, aryl or $-C(O)NR^aR^b$ wherein $R^a$ is H or $C_{1-6}$alkyl and $R^b$ is H or $C_{1-6}$alkyl;

each $R^3$, independently, is halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

Z is a fully or partially saturated 5-, 6- or 7-membered monocyclic ring comprising carbon atoms and optionally comprising 1-3 heteroatoms selected from N, O and S, or Z is a fully or partially saturated 7-, 8-, 9- or 10-membered N-linked bicyclic heterocyclic ring optionally comprising 1-2 additional heteroatoms selected from N, O and S;

m is 0, 1, 2, 3, 4 or 5; and n is 0, 1, 2, 3, 4 or 5.

In another embodiment, the compounds of Formula I include compounds wherein ring A is an optionally substituted 5- or 6-membered aryl or heteroaryl, in conjunction with any of the above or below embodiments.

In another embodiment, the compounds of Formula I include compounds wherein ring A is an optionally substituted 5-membered heteroaryl, in conjunction with any of the above or below embodiments.

In another embodiment, the compounds of Formula I include compounds wherein ring A is an optionally substituted 6-membered heteroaryl, in conjunction with any of the above or below embodiments.

In another embodiment, the compounds of Formula I include compounds wherein ring A is an optionally substituted 6-membered aryl, in conjunction with any of the above or below embodiments.

In another embodiment, the compounds of Formula I include compounds wherein ring A is an optionally substituted phenyl, pyridine, pyrimidine, triazine, pyrazine, pyridazine, imidazole, pyrazole, triazole, tetrazole, thiazole, oxazole, isoxazole, isothiazole, pyrrole, furan or thiophene, in conjunction with any of the above or below embodiments.

In another embodiment, the compounds of Formula I include compounds wherein ring A is an optionally substituted phenyl, pyridine, pyrimidine, triazine, pyrazinyl, pyridazinyl or thiophene, in conjunction with any of the above or below embodiments.

In another embodiment, the compounds of Formula I include compounds wherein each of $B^1$, $B^2$ and $B^3$, independently, is N, $-CF$, $-CCH_3$ or CH, in conjunction with any of the above or below embodiments.

In another embodiment, the compounds of Formula I include compounds wherein each of $B^1$, $B^2$ and $B^3$, independently, is $-CF$, $-CCH_3$ or CH, in conjunction with any of the above or below embodiments.

In another embodiment, the compounds of Formula I include compounds wherein each of $B^1$, $B^2$ and $B^3$, independently, is CH, in conjunction with any of the above or below embodiments.

In another embodiment, the invention provides compounds, including stereoisomers, tautomers or pharmaceutically acceptable salts thereof, generally defined by Formula I-A

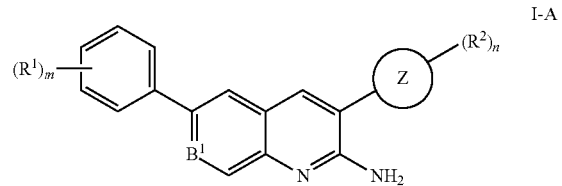

wherein $B^1$ is $-CF$, $-CCH_3$ or CH;

each $R^1$, independently, is halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $-C(O)C_{1-6}$-alkyl, $-C(O)$-cycloalkyl, $-C(=N-OH)-R^3$, $-C(=N-OCH3)-R^3$ or $-C(O)NR^aR^b$ wherein $R^a$ is H or $C_{1-6}$alkyl and $R^b$ is $R^3$, alternatively, $R^a$ and $R^b$ taken together with the nitrogen atom to which they are attached form a 4-7 membered monocyclic heterocycle, optionally substituted with 1-3 substituents of $R^3$; or $R^1$ is a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^3$;

each $R^2$ independently, is F, Cl, $CF_3$, $OCF_3$, $C_{1-6}$-alkyl, CN, OH, $-OC_{1-6}$-alkyl, $-OCF_3$, $-NH_2$, $NHCH_3$ or $-C(O)CH_3$;

each $R^3$, independently, is halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-16}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

Z is a fully or partially saturated 5-, 6- or 7-membered monocyclic ring comprising carbon atoms and optionally comprising 1-3 heteroatoms selected from N, O and S, or Z is a fully or partially saturated 7-, 8-, 9- or 10-membered N-linked bicyclic heterocyclic ring optionally comprising 1-2 additional heteroatoms selected from N, O and S;

m is 1, 2 or 3; and n is 0, 1 or 2.

In another embodiment, the invention provides compounds, including stereoisomers, tautomers or pharmaceutically acceptable salts thereof, generally defined by Formula I-A-I

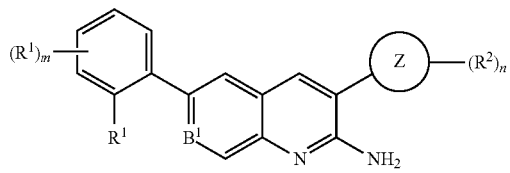

I-A-I wherein $B^1$ is —CF, —$CCH_3$ or CH;

each $R^1$, independently, is halo, haloalkyl, CN, OH, $NO_2$, $NH_2$, acetyl, $C_{1-6}$-alkyl, $C_{2-6}$-alkenyl, $C_{2-6}$-alkynyl, $C_{3-7}$-cycloalkyl, $C_{4-7}$-cycloalkenyl, $C_{1-6}$-alkylamino-, $C_{1-6}$-dialkylamino-, $C_{1-6}$-alkoxyl, $C_{1-6}$-thioalkoxyl, —C(O)—$R^3$, —C(O)$NHR^3$, —C(O)$OR^3$ or —C(O)$NR^aR^b$ wherein $R^a$ is H or $C_{1-6}$alkyl and $R^b$ is $R^3$, alternatively, $R^a$ and $R^b$ taken together with the nitrogen atom to which they are attached form a 4-7 membered monocyclic heterocycle, optionally substituted with 1-3 substituents of $R^3$; or $R^1$ is a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino $C_{1-10}$-alkoxyl, $C_{1-10}$-thioalkoxyl and ring of said ring system is optionally substituted independently with 1-5 substituents of $R^3$;

each $R^2$ independently, is F, Cl, $CF_3$, $OCF_3$, $C_{1-6}$-alkyl, CN, OH, —$OC_{1-6}$-alkyl, —$OCF_3$, —$NH_2$, $NHCH_3$ or —C(O)$CH_3$;

m is 0 or 1; and n is 0 or 1.

In one embodiment, the compounds of Formulas I, I-A and I-A-I include compounds wherein ring Z is

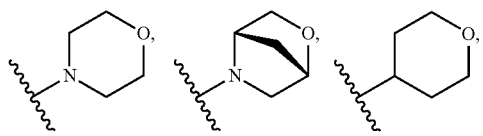

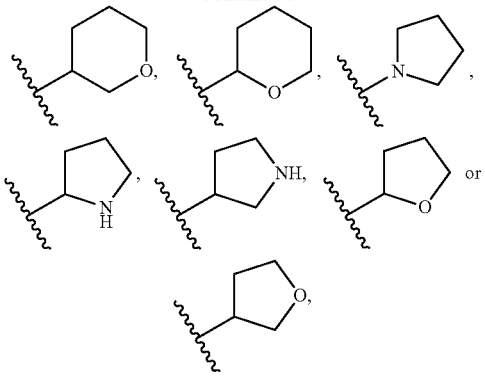

each ring of which is optionally substituted independently with 1-5 substituents of $R^2$, in conjunction with any of the above or below embodiments.

In one embodiment, the compounds of Formulas I, I-A and I-A-I include compounds wherein Z is

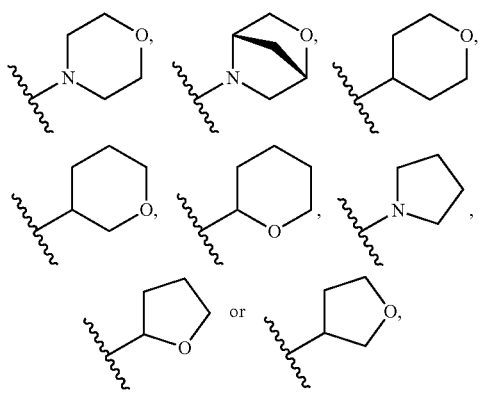

each ring of which is optionally substituted independently with 1-5 substituents of $R^2$, in conjunction with any of the above or below embodiments.

In one embodiment, the compounds of Formulas I, I-A and I-A-I include compounds wherein Z is a fully or partially saturated 5-, 6- or 7-membered monocyclic ring comprising carbon atoms and optionally comprising 1-3 heteroatoms selected from N, O and S, or Z is a fully or partially saturated 7-, 8-, 9- or 10-membered N-linked bicyclic heterocyclic ring optionally comprising 1-2 additional heteroatoms selected from N, O and S, in conjunction with any of the above or below embodiments.

In another embodiment, the compounds of Formulas I, I-A and I-A-I include compounds wherein Z is a fully or partially saturated 5-, 6- or 7-membered monocyclic ring comprising carbon atoms and optionally comprising 1-3 heteroatoms selected from N, O and S. In this embodiment, Z may be an N-linked fully or partially saturated 5-, 6- or 7-membered monocyclic ring, such as an optionally substituted morpholine or piperidine ring.

In one embodiment, the compounds of Formulas I, I-A and I-A-I include compounds wherein ring Z is morpholinyl, pyrrolidinyl, tetrahydropyranyl, tetrahydrofuranyl, oxa-azabicyclo[2.2.1]heptanyl or cyclopentenyl, wherein ring Z is optionally substituted, independently, with 1-5 substituents of $R^2$, in conjunction with any of the above or below embodiments.

In one embodiment, the compounds of Formulas I, I-A and I-A-I include compounds wherein ring Z is a morpholinyl, pyrrolidinyl, tetrahydropyranyl, tetrahydrofuranyl, piperidinyl, piperazinyl, oxa-aza-bicyclo[2.2.1]heptanyl, cyclopentyl, cyclohexyl, cyclopentenyl or pyranyl, each of which is optionally substituted with 1-3 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl or phenyl, in conjunction with any of the above or below embodiments.

In one embodiment, the compounds of Formulas I, I-A and I-A-I include compounds wherein each $R^1$, independently, is halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, —C(O)$C_{1-6}$-alkyl, —C(O)-cycloalkyl, —C(=N—OH)—$R^3$, —C(=N—OCH$_3$)—$R^3$, —C(O)O$R^3$ or C(O)N$R^aR^b$ wherein $R^a$ is H or $C_{1-6}$alkyl and $R^b$ is $R^3$, alternatively, $R^a$ and $R^b$ taken together with the nitrogen atom to which they are attached form a 4-7 membered monocyclic heterocycle, optionally substituted with 1-3 substituents of $R^3$; or $R^1$ is a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino, $C_{1-10}$-dialkylamino-, $C_{1-10}$-alkoxyl, $C_{1-10}$-thioalkoxyl and ring of said ring system is optionally substituted independently with 1-5 substituents of $R^3$, in conjunction with any of the above or below embodiments.

In one embodiment, the compounds of Formulas I, I-A and I-A-I include compounds wherein each $R^1$, independently, is halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, —C(O)$C_{1-6}$-alkyl, —C(O)-cycloalkyl, —C(=N—OH)—$R^3$, —C(=N—OCH$_3$)—$R^3$, —C(O)O$R^3$ or —C(O)N$R^aR^b$ wherein $R^a$ is H or $C_{1-6}$alkyl and $R^b$ is $R^3$, alternatively, $R^a$ and $R^b$ taken together with the nitrogen atom to which they are attached form a 4-7 membered monocyclic heterocycle, optionally substituted with 1-3 substituents of $R^3$, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl and $C_{1-10}$-thioalkoxyl is optionally substituted independently with 1-5 substituents of $R^3$, in conjunction with any of the above or below embodiments.

In one embodiment, the compounds of Formulas I, I-A and I-A-I include compounds wherein each $R^1$, independently, is a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each ring of said ring system is optionally substituted independently with 1-5 substituents of $R^3$, in conjunction with any of the above or below embodiments.

In one embodiment, the compounds of Formulas I, I-A and I-A-I include compounds wherein each $R^1$, independently, is F, Cl, Br, I, $CF_3$, $C_2F_5$, $CH_3$, $C_2H_5$, propyl, butyl, isopropyl, isobutyl, pentyl, —O$C_{1-6}$alkyl, OH, $NH_2$, —NH$C_{1-6}$alkyl, —N-di-$C_{1-6}$alkyl, —C(O)NH$C_{1-6}$alkyl, —C(O)$C_{1-6}$alkyl, —C(O)cycloalkyl, —C(O)-aryl, —C(O)-heteroaryl, —C(O)NH-aryl, —C(O)NH-heteroaryl, —C(O)NH-cycloalkyl, —C(=N—OH)—$R^3$, —C(=N—OCH$_3$)—$R^3$, —C(O)O$R^3$, $C_{3-8}$cycloalkyl, aryl, heteroaryl or heterocyclyl, in conjunction with any of the above or below embodiments.

In another embodiment, Formulas I, I-A and I-A-I include compounds wherein each of $R^1$ is F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment, Formulas I, I-A and I-A-I include compounds wherein each $R^1$ independently, is F, Cl, Br, $CF_3$, $OCF_3$, $C_{1-6}$-alkyl, CN, OH, —O$C_{1-6}$-alkyl, —S(O)—$C_{1-6}$-alkyl, —$NH_2$, CN, —NH$C_{1-6}$-alkyl, —C(O)$C_{1-6}$-alkyl, —C(O)$C_{1-6}$cycloalkyl, —C(O)-tetrahydropyrrole, in conjunction with any of the above or below embodiments.

In another embodiment, Formulas I, I-A and I-A-I include compounds wherein each $R^2$, independently, is H, $C_{1-3}$alkyl or halo, in conjunction with any of the above or below embodiments.

In another embodiment, Formulas I, I-A and I-A-I include compounds wherein each $R^2$, independently, is H, $CH_3$, $CH_2CH_3$, F or Cl, in conjunction with any of the above or below embodiments.

In one embodiment, the compounds of Formulas I, I-A and I-A-I include compounds wherein each $R^2$, independently, is halo, haloalkyl, haloalkoxyl, CN, $NO_2$, $NH_2$, OH, oxo, $C_{1-6}$-alkyl, —O$C_{1-6}$-alkyl, —S(O)—$C_{1-6}$-alkyl, —NH$C_{1-6}$-alkyl, aryl or —C(O)N$R^aR^b$ wherein $R^a$ is H or $C_{1-6}$alkyl and $R^b$ is H or $C_{1-6}$alkyl, in conjunction with any of the above or below embodiments.

In one embodiment, the compounds of Formulas I, I-A and I-A-I include compounds wherein each $R^2$ independently, is F, Cl, $CF_3$, $OCF_3$, $C_{1-6}$-alkyl, CN, OH, —O$C_{1-6}$-alkyl, —$OCF_3$, —$NH_2$, $NHCH_3$ or —$C(O)CH_3$, in conjunction with any of the above or below embodiments.

In another embodiment, the invention provides compounds, including stereoisomers, tautomers or pharmaceutically acceptable salts thereof, generally defined by Formula I-B-I

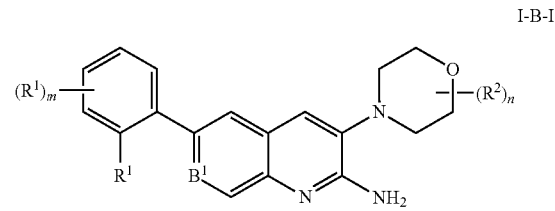

I-B-I wherein $B^1$ is —CF, —CCH$_3$ or CH;

each $R^1$, independently, is halo, haloalkyl, CN, OH, $NO_2$, $NH_2$, acetyl, $C_{1-6}$-alkyl, $C_{2-6}$-alkenyl, $C_{2-6}$-alkynyl, $C_{3-7}$-cycloalkyl, $C_{4-7}$-cycloalkenyl, $C_{1-6}$-alkylamino-, $C_{1-6}$-dialkylamino-, $C_{1-6}$-alkoxyl, $C_{1-6}$-thioalkoxyl, —C(O)—$R^3$, —C(O)NH$R^3$, —C(O)O$R^3$ or C(O)N$R^aR^b$ wherein $R^a$ is H or $C_{1-6}$alkyl and $R^b$ is $R^3$, alternatively, $R^a$ and $R^b$ taken together with the nitrogen atom to which they are attached form a 4-7 membered monocyclic heterocycle, optionally substituted with 1-3 substituents of $R^3$; or $R^1$ is a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^3$;

each $R^2$ independently, is F, Cl, $CF_3$, $OCF_3$, $C_{1-6}$-alkyl, CN, OH, —$OC_{1-6}$-alkyl, —$OCF_3$, —$NH_2$, $NHCH_3$ or —$C(O)CH_3$;

m is 0 or 1; and n is 0 or 1.

In one embodiment, the compounds of Formulas I, I-A, I-A-I and I-B-I include compounds wherein m is 0, 1, 2, 3, 4 or 5, in conjunction with any of the above or below embodiments.

In one embodiment, the compounds of Formulas I, I-A, I-A-I and I-B-I include compounds wherein m is 0, 1, 2 or 3, in conjunction with any of the above or below embodiments.

In one embodiment, the compounds of Formulas I, I-A, I-A-I and I-B-I include compounds wherein m is 0, 1 or 2, in conjunction with any of the above or below embodiments.

In one embodiment, the compounds of Formulas I, I-A, I-A-I and I-B-I include compounds wherein m is 0 or 1, in conjunction with any of the above or below embodiments.

In one embodiment, the compounds of Formulas I, I-A, I-A-I and I-B-I include compounds wherein n is 0, 1, 2, 3, 4 or 5, in conjunction with any of the above or below embodiments.

In one embodiment, the compounds of Formulas I, I-A, I-A-I and I-B-I include compounds wherein n is 0, 1, 2 or 3, in conjunction with any of the above or below embodiments.

In one embodiment, the compounds of Formulas I, I-A, I-A-I and I-B-I include compounds wherein n is 0, 1 or 2, in conjunction with any of the above or below embodiments.

In one embodiment, the compounds of Formulas I, I-A, I-A-I and I-B-I include compounds wherein n is 0 or 1, in conjunction with any of the above or below embodiments.

In one embodiment, the compounds of Formulas I, I-A, I-A-I and I-B-I include compounds wherein n is 0, in conjunction with any of the above or below embodiments.

In another embodiment, Formulas I, I-A, I-A-I and I-B-I include compounds wherein $R^3$ is a fully saturated or partially or fully unsaturated 5- or 6-membered monocyclic or bicyclic ring formed of carbon atoms, said ring optionally including 1-4 heteroatoms selected from O, N, or S, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl, in conjunction with any of the above or below embodiments.

In another embodiment, Formulas I, I-A, I-A-I and I-B-I include compounds wherein $R^3$ is a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, said ring optionally substituted, independently, with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl, in conjunction with any of the above or below embodiments.

In another embodiment, Formulas II, I-A, I-A-I and I-B-I include compounds wherein $R^3$ is halo, haloalkyl, haloalkoxyl, $C_{1-6}$-alkyl, $C_{2-6}$alkenyl, $C_{2-6}$-alkynyl, $C_{3-8}$-cycloalkyl, $C_{4-8}$-cycloalkenyl, or a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, said ring optionally substituted, independently, with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl, in conjunction with any of the above or below embodiments.

In another embodiment, Formulas I, I-A, I-A-I and I-B-I include compounds wherein $R^3$ is $C_{1-4}$alkyl substituted with 1-3 substituents of F, Cl, Br, I, $CF_3$, $C_2F_5$ and haloalkoxyl, or $R^4$ is F, Cl, Br, I, $CF_3$, $C_2F_5$, haloalkoxyl, CN, OH, $OC_{1-6}$-alkyl, $SC_{1-6}$-alkyl, $SC_{1-6}$-alkyl, $S(O)_oC_{1-6}$-alkyl, cycloalkyl, aryl, heteroaryl or heterocyclyl wherein the cycloalkyl, aryl, heteroaryl or heterocyclyl is optionally substituted independently with 1-5 substituents of F, Cl, Br, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-4}$-alkylamino-, $C_{1-4}$-dialkylamino- or $C_{1-4}$-thioalkoxyl, in conjunction with any of the above or below embodiments.

In another embodiment, Formulas I, I-A, I-A-I and I-B-I include compounds wherein $R^3$ is F, Cl, Br, I, $CF_3$, $C_2F_5$, haloalkoxyl, CN, OH, $OC_{1-6}$-alkyl, $SC_{1-6}$-alkyl, $SC_{1-6}$-alkyl, $S(O)_oC_{1-6}$-alkyl wherein o is 0, 1 or 2, $NHC_{1-6}$-alkyl or $C(O)C_{1-6}$-alkyl, in conjunction with any of the above or below embodiments.

In another embodiment, the invention provides the compound of Formula I, I-A, I-A-I or I-B-I, or a stereoisomer or pharmaceutically acceptable salt thereof, selected from any of the compound examples 1-221, presented hereinbelow in Table 1.

In another embodiment, the invention provides each of the Examplary compounds, and stereoisomers, tautomers, solvates, pharmaceutically acceptable salts, derivatives or prodrugs thereof, and related intermediates, described herein.

In another embodiment, the invention provides the exemplified compounds described herein, and stereoisomers and pharmaceutically acceptable salt forms of each thereof.

Definitions

The following definitions should assist in understanding the invention described herein.

The term "comprising" is meant to be open-ended, i.e., all encompassing, all inclusive and non-limiting. It may be used herein synonymously with "having" or "including." "Comprising" is intended to include each and every indicated or recited component or element(s) while not excluding any other components or elements.

The term "$C_{\alpha\text{-}\beta}$alkyl", when used either alone or within other terms such as "haloalkyl" and "alkylamino", embraces linear or branched radicals having α to β number of carbon atoms (such as $C_1$-$C_{10}$; $C_1$-$C_6$; or $C_1$-$C_4$). Unless otherwise specified, one or more carbon atoms of the "alkyl" radical may be substituted, such as with a cycloalkyl moiety. Examples of "alkyl" radicals include methyl, cyclopropylmethyl, cyclobutylmethyl, cyclopentylmethyl, ethyl, cyclopropylethyl, cyclobutylethyl, cyclopentylethyl, n-propyl, isopropyl, n-butyl, cyclopropylbutyl, isobutyl, sec-butyl, tert-butyl, pentyl, isoamyl, hexyl and the like.

The term "$C_{\alpha\text{-}\beta}$alkenyl", when used alone or in combination, embraces linear or branched radicals having at least one carbon-carbon double bond in a moiety having a number of carbon atoms in the range from α and β. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "$C_{\alpha\text{-}\beta}$alkynyl", when used alone or in combination, denotes linear or branched radicals having at least one carbon-carbon triple bond in a moiety having a number of carbon atoms in the range from α and β. Examples of alkynyl radicals include "lower alkynyl" radicals having two to about six carbon atoms and, for example, lower alkynyl radicals having two to about four carbon atoms. Examples of such radicals include, without limitation, ethynyl, propynyl (propargyl), butynyl, and the like.

The term "$C_{\alpha\text{-}\beta}$-alkyl", "$C_{\alpha\text{-}\beta}$-alkenyl" and "$C_{\alpha\text{-}\beta}$-alkynyl", when used with other terms such as "wherein 1, 2 or 3 carbon atoms of said $C_{\alpha\text{-}\beta}$-alkyl, $C_{\alpha\text{-}\beta}$-alkenyl or $C_{2\alpha\text{-}\beta}$-alkynyl is optionally replaced with a heteroatom selected from O, S, S(O), S(O)$_2$ and N" embraces linear or branched radicals wherein one or more of the carbon atoms may be replaced with a heteroatom. Examples of such "alkyl" radicals include —O-methyl, —O-ethyl, —CH$_2$—O—CH$_3$, —CH$_2$CH$_2$—O—CH$_3$, —NH—CH$_2$, —CH$_2$CH$_2$—N(CH$_3$)—CH$_3$, —S—(CH$_2$)$_3$CH$_2$, —CH$_2$CH$_2$—S—CH$_3$ and the like. Accordingly, such radicals also include radicals encompassed by —OR$^7$ where R$^7$ may be defined as a $C_{\alpha\text{-}\beta}$-alkyl. Examples of such "alkenyl" radicals include —NH—CH$_2$CH=CH$_2$, —S—CH$_2$CH$_2$CH=CHCH$_3$ and the like. Similar examples exist for such "alkynyl" radicals, as appreciated by those skilled in the art.

The term "$C_{\alpha\text{-}\beta}$alkoxyl" when used alone or in combination, embraces linear or branched oxygen-containing alkyl radicals each having α to β number of carbon atoms (such as $C_1$-$C_{10}$). The terms "alkoxy" and "alkoxyl", when used alone or in combination, embraces linear or branched oxygen-containing radicals each having alkyl and substituted alkyl portions of one or more carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals or with other substitution. Examples of such radicals include fluoromethoxy, chloromethoxy, trifluoromethoxy, trifluoroethoxy, fluoroethoxy, fluoropropoxy and cyclopropylmethoxy.

The term "aryl", when used alone or in combination, means a carbocyclic aromatic moiety containing one, two or even three rings wherein such rings may be attached together in a fused manner. Every ring of an "aryl" multi-ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substituents including lower alkyl, hydroxyl, halo, haloalkyl, nitro, cyano, alkoxy and lower alkylamino, and the like. Phenyl substituted at two carbons with —O—CH$_2$—O— or —O—CH$_2$—CH$_2$—O— form an aryl benzodioxolyl substituent.

The term "cycloalkyl", also referred to herein as "carbocyclic" or "carbocyclyl", when used alone or in combination, means a partially or fully saturated ring moiety formed of carbon atoms and comprising one ("monocyclic"), two ("bicyclic") or even three ("tricyclic") rings wherein such rings may be attached together in a fused manner. Examples of saturated cycloalkyl radicals include saturated 3 to 6-membered monocyclic groups such as cyclopropane, cyclobutane, cyclopentane and cyclohexane.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 3-8 for a monocyclic and 6-12 for a bicyclic ring. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The term "cycloalkenyl", when used alone or in combination, means a partially or fully saturated cycloalkyl containing one, two or even three rings in a structure having at least one carbon-carbon double bond in the structure. Examples of cycloalkenyl groups include $C_3$-$C_6$ rings, such as compounds including, without limitation, cyclopropene, cyclobutene, cyclopentene and cyclohexene. The term also includes carbocyclic groups having two or more carbon-carbon double bonds such as "cycloalkyldienyl" compounds. Examples of cycloalkyldienyl groups include, without limitation, cyclopentadiene and cycloheptadiene.

The term "halo", when used alone or in combination, means halogens such as fluorine (F), chlorine (Cl), bromine (Br) or iodine (I) atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl (CF$_3$), chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, azaquinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The term "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and fully saturated heterocyclyls include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1$\lambda$'-benzo[d]isothiazol-6-yl, dihydropyranyl, dihydrofuryl and dihydrothiazolyl, and the like.

The phrase "a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S" as used herein is intended to encompass all monocyclic and bicyclic rings as small as three atoms to as large as 12 atoms in size, including both carbocyclic rings and heterocyclic, aromatic and non-aromatic rings. The non-aromatic rings may be partially or fully saturated in nature.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N,N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The term "carbonyl", whether used alone or with other terms, such as "aminocarbonyl", denotes —(C=O)—. "Carbonyl" is also used herein synonymously with the term "oxo".

The term "aminocarbonyl" denotes an amide group of the formula —C(=O)NH$_2$.

The term "alkylthio" or "thioalkoxy" embraces radicals containing a linear or branched alkyl radical, of one to ten carbon atoms, attached to a divalent sulfur atom. An example of "alkylthio" or "thioalkoxy" is methylthio, (CH$_3$S—).

The term "Formula I" includes any sub formulas, such as Formulas I-A, I-A-I and Formulas I-B-I.

The term "pharmaceutically-acceptable" when used with reference to a compound of Formulas I, I-A, I-A-I and I-B-I is intended to refer to a form of the compound that is safe for administration. For example, a salt form, a solvate, a hydrate, a prodrug or derivative form of a compound of Formulas I, I-A, I-A-I and I-B-, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I, I-A, I-A-I and I-B-I are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I, I-A, I-A-I and I-B-I may be prepared from an inorganic acid or from an organic acid. Examples of such inorganic acids are hydrochloric, hydrobromic, hydroiodic, hydrofluoric, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I, I-A and I-B include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I, I-A, I-A-I and I-B-I.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Additional examples of such salts can be found in Berge et al., J. Pharm. Sci., 66:1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "derivative" is intended to encompass any salt of a compound of this invention, any ester of a compound of this invention, or any other compound, which upon administration to a patient is capable of providing (directly or indirectly) a compound of this invention, or a metabolite or residue thereof, characterized by the ability of the derivative to modulate an enzyme.

The term "pharmaceutically-acceptable derivative" as used herein, denotes a derivative which is pharmaceutically acceptable.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formulas I, I-A and I-B. A "pharmaceutically-acceptable prodrug" as used herein, denotes a prodrug which is pharmaceutically acceptable. Pharmaceutically acceptable modifications to the compounds of Formula I, I-A, I-A-I and I-B-I are readily appreciated by those of ordinary skill in the art.

The compound(s) of Formulas I, I-A, I-A-I and I-B-I may be used to treat a subject by administering the compound(s) as a pharmaceutical composition. To this end, the compound(s) can be combined with one or more excipients, including without limitation, carriers, diluents or adjuvants to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. Accordingly, this term is not limited to a single dose, but may comprise multiple dosages required to bring about a therapeutic or prophylactic response in the subject. For example, "effective dosage amount" is not limited to a single capsule or tablet, but may include more than one capsule or tablet, which is the dose prescribed by a qualified physician or medical care giver to the subject.

The term "leaving group" (also denoted as "LG") generally refers to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

General Synthetic Procedures

The present invention further comprises procedures for the preparation of compounds of Formulas I, I-A, I-A-I and I-B-I. The compounds of Formulas I, I-A, I-A-I and I-B-I can be synthesized according to the procedure described in Scheme 1, wherein the substituents are as defined for Formulas I, I-A, I-A-I and I-B-I above, except where further noted. The compounds of the present invention may also be prepared according to one or more of the methods, and/or steps described therein, as described in examples 1-57 herein. To this end, the synthetic methods described below are merely exemplary, and the compounds of the invention may further be synthesized by alternate routes utilizing alternative synthetic strategies, as appreciated by persons of ordinary skill in the art.

The following list of abbreviations, used throughout the specification, represent the following, and should assist in understanding the invention:

| | |
|---|---|
| ACN, MeCN | acetonitrile |
| Aq., aq. | aqueous |
| Ar | argon (gas) |
| BOP | benzotriazol-1-yl-oxy Hexafluorophosphate |
| BuLi | Butyllithium |
| $Cs_2CO_3$ | cesium carbonate |
| $CHCl_3$ | chloroform |
| $CH_2Cl_2$, DCM | dichloromethane, methylene chloride |
| Cu(1)I | copper(1) iodide |
| DCC | N,N-dicyclohexylcarbodiimide |
| DIC | 1,3-diisopropylcarbodiimide |
| DIEA, DIPEA | N,N-diisopropylethylamine |
| DIPA | N,N-diisopropylamine |
| DME | dimethoxyethane |
| DMF | N,N-dimethylformamide |
| DMAP | 4-dimethylaminopyridine |
| DMS | dimethylsulfide |
| DMSO | dimethylsulfoxide |
| EDC, EDCI | 1-(3-dimethylaminopropyl)-3-ethylcarbodiimide |
| $Et_2O$ | diethyl ether |
| EtOAc | ethyl acetate |
| FBS | fetal bovine serum |
| G, gm | gram |
| h, hr | hour |
| $H_2$ | hydrogen (gas) |
| $H_2O$ | water |
| HATU | O-(7-azabenzotriazol-1-yl)-N,N,N',N'-tetramethyluroniumhexafluorophosphate |
| HBr | hydrobromic acid |
| HCl | hydrochloric acid |
| HOBt | 1-hydroxybenzotriazole hydrate |
| HOAc | acetic acid |
| HPLC | high pressure liquid chromatography |
| IPA, IpOH | isopropyl alcohol |
| $K_2CO_3$ | potassium carbonate |
| KI | potassium iodide |
| KOH | potassium hydroxide |
| LG | leaving group |
| LDA | Lithium diisopropylamide |
| LiOH | lithium hydroxide |
| $MgSO_4$ | magnesium sulfate |
| MS | mass spectrum |
| MeOH | methanol |
| $N_2$ | nitrogen (gas) |
| $NaCNBH_3$ | sodium cyanoborohydride |
| $Na_2CO_3$ | sodium carbonate |
| $NaHCO_3$ | sodium bicarbonate |
| NaH | sodium hydride |
| NaI | sodium iodide |
| $NaBH_4$ | sodium borohydride |
| NaOH | sodium hydroxide |
| $Na_2SO_4$ | sodium sulfate |
| $NH_4Cl$ | ammonium chloride |
| $NH_4OH$ | ammonium hydroxide |
| NMP | N-methyl pyrrolidine |
| $P(t-bu)_3$ | tri(tert-butyl)phosphine |
| PBS | phosphate buffered saline |
| Pd/C | palladium on carbon |
| $Pd(PPh_3)_4$ | palladium(0)triphenylphosphine tetrakis |
| $Pd(dppf)Cl_2$ | palladium(1,1 bisdiphenylphosphinoferrocene) II chloride |
| $Pd(PhCN)_2Cl_2$ | palladium di-cyanophenyl dichloride |
| $Pd(OAc)_2$ | palladium acetate |
| $Pd_2(dba)_3$ | tris(dibenzylideneacetone) dipalladium |
| PyBop | benzotriazol-1-yl-oxy-tripyrrolidino-phosphonium hexafluorophosphate |
| RT, rt | room temperature |
| RBF, rbf | round bottom flask |
| TLC, tlc | thin layer chromatography |
| TBAF | Tetrabutylammonium flouride |
| TBTU | O-benzotriazol-1-yl-N,N,N',N'-tetramethyluronium tetrafluoroborate |
| TEA, $Et_3N$ | triethylamine |
| TFA | trifluoroacetic acid |
| THF | tetrahydrofuran |
| UV | ultraviolet light |

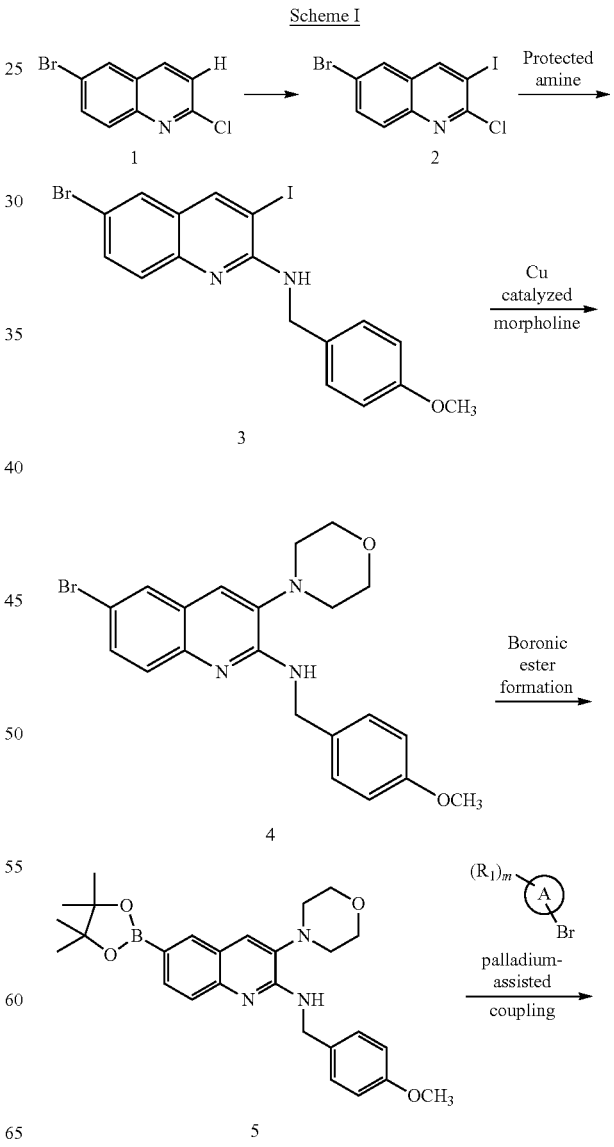

Scheme I

-continued

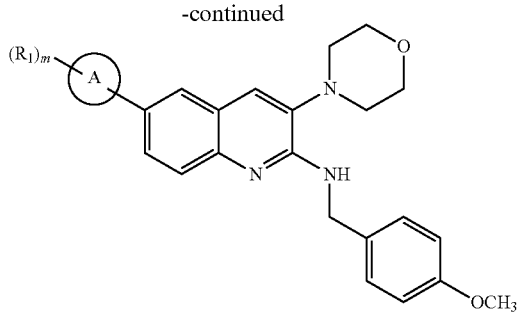

6

↓ deprotection

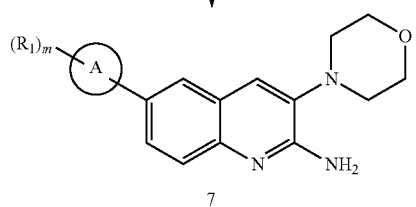

7

Compounds 7 of formulas I, I-A, I-A-I and I-B-I may be prepared by the method generally illustrated in scheme I and described step-by-step below. Ring Z of Formulas I, I-A and I-A-I as shown is an optionally substituted morpholine ring (Formula I-B-I).

6-Bromo-2-chloro quinoline 1 (may be purchased or made separated by known published methods, as discussed hereinbelow) may be converted to 6-bromo-3-iodo-2-chloro quinoline 2, using a suitable iodine source and reaction conditions, such as convention conditions. For example, Example 1 describes one method of preparing compound 2. The chloro group of compound 2 may be displaced with a suitably protected amine, such as shown above, by 4-methoxybenzylamine, under suitable conditions to afford the protected amino-quinoline 3.

The iodo group of compound 3 may then be displaced with morpholine under suitable conditions, such as those described in Example 1 below, which utilize a copper catalyst, to afford the 3-morpholino-quinoline intermediate 4, as shown above. Morpholine is merely an exemplary N-linked saturated or partially saturated, optionally substituted ring Z which may be installed at position 3 of the quinoline ring. Though scheme 1 illustrates a morpholine as ring Z, the present invention is not so limited, and other rings defined herein may be at this position on the amino-quinoline core ring of Formulas I, I-A and I-A-I. Intermediate 4 may then converted to a more active reagent via conversion of the bromide to a corresponding boronic acid derivative, such the doxolo-borane intermediate 5 shown above. One method of preparing compound 5 is described in Example 1 below.

The boronic acid, and/or ester, intermediates 5 may be prepared by methods described in the following references: (1) PCT Int. Patent Appl. No. WO 2005073189, titled "Preparation of fused heteroaryl derivatives as p38 kinase inhibitors" or (2) PCT Int. Patent Appl. No. WO 2006094187, titled "Preparation of phthalazine, aza- and diaza-phthalazine compounds as protein kinase, especially p38 kinase, inhibitors for treating inflammation and related conditions". Also, desired boronic acids may be commercially purchased or internally prepared as needed.

The boronate ester 5 can then be displaced by suitable aromatic bromides, such as bromo-phenyl compounds, to afford the corresponding desirable 6-substituted protected quinoline amines 6. Compound 6, for example, may be prepared using conventional Suzuki or Suzuki-like reaction conditions and reagents. Suzuki reactions are a known type of reaction involving a boronic acid reagent and a suitable aromatic bromide, such as the Br-aromatic ring A (Br is a suitable halogen leaving group "LG"). As appreciated to one of ordinary skill in the art, Suzuki and Suzuki-like reactions also utilize a palladium catalyst. Suitable palladium catalysts include, without limitation, Pd(PPh$_3$)$_4$, Pd(OAc)$_2$ or Pd(dppf)Cl$_2$. Where LG is a halide, the halide may be an iodide, a bromide or even a chloride. Chloro-pyridyl rings undergo Suzuki reactions in the presence of Pd(OAc)$_2$. Other LGs are also suitable. For example, Suzuki couplings are known to occur with a sulfonate, such as trifluoromethanesulfonate, as the leaving group.

The Suzuki reaction conditions may vary. For example, Suzuki reactions are run generally in the presence of a suitable base such as a carbonate base, bicarbonate or an acetate base, in a suitable solvent such as toluene, acetonitrile, DMF or an aqueous-organic solvent combination or a biphasic system of solvents. Alternatively, the reaction may simply require solvent and heat depending upon the particular bromide 3 and/or boronic acid or ester, as appreciated by those skilled in the art. Other methods of installing the boronate on a desired aromatic ring are known. For example metal coupling chemistry, such Stille, Kumada, Negishi coupling methods, and the like, may be employed to prepare desired products 6.

Compound 6 can then simply be deprotected to provide targeted compounds 7. Scheme 1 above exemplifies one general method of preparing desired compounds 7. However, the invention is not so limited, and other methods for preparing compounds 7 are within the scope of the present invention, including those described in the Examples hereinbelow.

EXAMPLES

The Examples, described herein below, represent various exemplary starting materials, intermediates and compounds of Formulas I, I-A, I-A-I and I-B-I, which should assist in a better understanding and appreciation of the scope of the present invention and of the various methods which may be used to synthesize compounds of Formulas I, I-A, I-A-I and I-B-I. It should be appreciated that the general methods above and specific examples below are illustrative only, for the purpose of assistance and of understanding the present invention, and should not be construed as limiting the scope of the present invention in any manner. The exemplary compounds disclosed herein have been named using either (1) the naming convention provided with Chem-Draw Ultra 8.0 software, available in Chem Office, or (2) by the ISIS database software (Advanced Chemistry Design Labs or ACD software).

Chromatography:

Unless otherwise indicated, crude product-containing residues were purified by passing the crude material or concentrate through an ISCO brand silica gel column (pre-packed or individually packed with SiO$_2$) and eluting the product off the column with a solvent gradient as indicated. For example a description of (330 g SiO$_2$, 0-40% EtOAc/Hexane) means the product was obtained by elution from the column packed with 330 gms of silica, with a solvent gradient of 0% to 40% EtOAc in Hexanes.

Preparative HPLC Method:

Unless otherwise indicated, the compounds described herein were purified via reverse phase HPLC using one of the following instruments: Shimadzu, varian, Gilson; utilizing one of the following two HPLC columns: (a) a Phenomenex Luna or (b) a Gemini column (5 micron or 10 micron, C18, 150×50 mm)

A typical run through the instrument included: eluting at 45 ml/min with a linear gradient of 10% (v/v) to 100% MeCN (0.1% v/v TFA) in water (0.1% TFA) over 10 minutes; conditions can be varied to achieve optimal separations.

Proton NMR Spectra:

Unless otherwise indicated, all $^1$H NMR spectra were run on a Bruker series 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS):

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method (commonly referred to as an ESI MS) utilizing a PE SCIEX API 150EX MS instrument or an Agilent 1100 series LC/MSD system. Compounds having an isotopic atom, such as bromine and the like, are generally reported according to the detected isotopic pattern, as appreciated by those skilled in the art.

Example 1

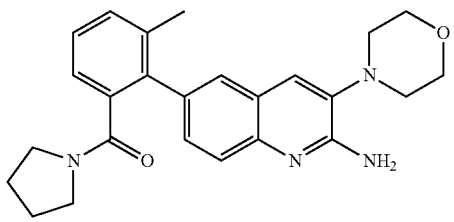 [SMILES: Cc1cccc(C(=O)N2CCCC2)c1-c1ccc2nc(N)c(N3CCOCC3)cc2c1]

Synthesis of (2-(2-amino-3-morpholinoquinolin-6-yl)-3-methylphenyl)(pyrrolidin-1-yl)methanone Step 1:

To a solution of THF (50 mL) and DIPA (1.8 mL, 12.37 mmol) at −70° C. was added n-BuLi (7.7 mL, 12.4 mmol). The mixture was allowed to stir at 0° C. for 1 h. Slow addition of 6-bromo-2-chloroquinoline (3.0 g, 12.4 mmol) in THF (50 mL) was achieved at −75° C. and the mixture was stirred at this temperature for 2 h. Iodine (3.1 g, 12.4 mmol) in 10 ml of THF was then slowly added and the reaction mixture was allowed to stir at −75° C. for 2 h before hydrolysis by THF/water (20% v/v). Water and diethyl ether were added at −10° C. and the reaction mixture was extracted with ether. The organic layer was washed with sodium thiosulfate and water, dried over MgSO$_4$ and concentrated in vacuo to give a yellow solid which was slurried with hexane and filtered to give 6-bromo-2-chloro-3-iodoquinoline as a tan solid.

Step 2:

6-Bromo-2-chloro-3-iodoquinoline (1.0 g, 2.7 mmol) and neat 4-methoxybenzylamine (3.6 mL, 27.1 mmol) was combined in a microwave vial and heated in a microwave at 130° C. for 15 min. The reaction mixture was purified by silica flash chromatography (0-30% EtOAc/Hex) to give 6-bromo-3-iodo-N-(4-methoxybenzyl)quinolin-2-amine as a yellow solid.

Step 3:

A mixture of 6-bromo-3-iodo-N-(4-methoxybenzyl)quinolin-2-amine (710 mg, 1.5 mmol), morpholine (1.9 mL, 22.7 mmol), Cu(I)(14.4 mg, 0.08 mmol), cesium carbonate (986 mg, 3.0 mmol), 2-isobutyrylcyclohexanone (50.9 mg, 0.30 mmol) and DMF (10 mL) was heated to 125° C. in a microwave unit for 20 min. The mixture was concentrated in vacuo then partioned the crude product between EtOAc and water. The organic layer was washed with water and brine 3× each, dried over MgSO$_4$ and concentrated in vacuo to give an orange colored oil. This material was purified by silica flash chromatography (0-5% MeOH/DCM) to give 6-bromo-N-(4-methoxybenzyl)-3-morpholinoquinolin-2-amine as a yellow colored oil.

Step 4:

A mixture of 6-bromo-N-(4-methoxybenzyl)-3-morpholinoquinolin-2-amine (430 mg, 1.0 mmol), 4,4,4',4',5,5,5',5'-octamethyl-2,2'-bi(1,3,2-dioxaborolane) (306 mg, 1.2 mmol), 1,1'-bis(diphenylphosphino)ferrocene-palladium (36.7 mg, 0.050 mmol), potassium acetate (493 mg, 5.0 mmol), and DMF (7 mL) was heated in a microwave at 125° C. for 15 min. The mixture was diluted with EtOAc, washed with water (3×), dried on MgSO$_4$ and concentrated in vacuo. This material was purified by silica flash chromatography (0-80% EtOAc/Hex, then 0-10% MeOH:DCM) to give N-(4-methoxybenzyl)-3-morpholino-6-(4,4,5,5-tetramethyl-1,3,2-dioxaborolan-2-yl)quinolin-2-amine.

Step 5:

2-Bromo-3-methylbenzoic acid (5.0 g, 23.3 mmol) was dissolved in THF (100 mL) and added N,N'-carbonyldiimidazole (4.52 g, 27.9 mmol). The reaction mixture was stirred at ambient temperature for 14 h. Pyrrolidine (6.8 mL, 81 mmol) was added in one portion. The mixture was stirred for 8 h and then partitioned between EtOAc and water. The organic layer was washed with water, diluted HCl, saturated bicarbonate, water and brine. The solution was then concentrated in vacuo to afford (2-bromo-3-methylphenyl)(pyrrolidin-1-yl)methanone as a white crystalline solid, upon standing overnight at RT.

Step 6:

A mixture of 2-dicyclohexylphosphino-2',4',6'-triisopropylbiphenyl (47.8 mg, 0.10 mmol), (2-bromo-3-methylphenyl)(pyrrolidin-1-yl)methanone (323 mg, 1.2 mmol), N-(4-methoxybenzyl)-3-morpholino-6-(4,4,5,5-tetramethyl-1,3,2-dioxaborolan-2-yl)quinolin-2-amine (477 mg, 1.0 mmol), Pd$_2$(dba)$_3$ (45.9 mg, 0.050 mmol), K$_3$PO$_4$ (0.25 mL, 3.0 mmol), and 1,4-dioxane (7 mL)/water (3.50 mL) was heated in a microwave at 140° C. for 12 min. The reaction mixture was filtered then concentrated in vacuo. The crude product was purified by silica flash chromatography (0-10% MeOH/DCM) to give (2-(2-(4-methoxybenzylamino)-3-morpholinoquinolin-6-yl)-3-methylphenyl)(pyrrolidin-1-yl)methanone as an orange oil.

Step 7:

A solution of (2-(2-(4-methoxybenzylamino)-3-morpholinoquinolin-6-yl)-3-methylphenyl)(pyrrolidin-1-yl)methanone (30 mg, 0.056 mmol) and TFA (2 mL) was heated at 90° C. After 3 h, the reaction mixture was concentrated in vacuo, diluted with DCM and concentrated again. The crude product was dissolved in MeOH and filtered through an SCX (1 g) column then eluted with a 2M ammonia methanol solution to release the product. This filtrate was concentrated in vacuo to give a light orange solid that was washed with ether and decanted to remove most of the remaining starting material. The remaining solid was dissolved in DCM and purified by preparative thin layer chromatography (5×20 cm, 1000 um, 10% MeOH:DCM) to give (2-(2-amino-3-morpholinoquinolin-6-yl)-3-methylphenyl)(pyrrolidin-1-yl)methanone as a white solid. MS (ESI, pos. ion) m/z: 417 (M+1).

Example 2

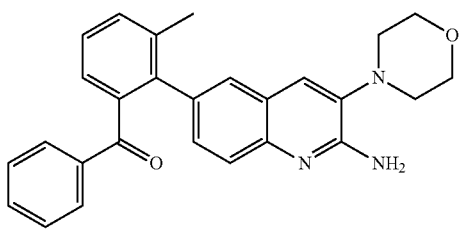 [SMILES: Cc1cccc(C(=O)c2ccccc2)c1-c1ccc2nc(N)c(N3CCOCC3)cc2c1]

Synthesis of (2-(2-amino-3-morpholinoquinolin-6-yl)-3 methylphenyl)(phenyl)methanone Step 1:
A solution of 2-morpholinoacetonitrile (6.4 g, 50.7 mmol) in DMSO (60 mL) was treated with concentrated aqueous KOH (1.37 mL, 15.99 mmol) and warmed to 80° C. A solution of 2-amino-5-bromobenzaldehyde (5.99 g, 29.9 mmol) in DMSO (68 mL) was added dropwise over 2 h. The reaction mixture was stirred for 2 h at this temperature, and after the addition was complete, it was allowed to cool to RT. The crude dark brown mixture was then added slowly to 600 mL $H_2O$ and ~25 mL saturated ammonium chloride. The aqueous mixture was then extracted with DCM 2×500 mL and the combined DCM layers were washed with 4×800 mL brine. The organics were dried over sodium sulfate and concentrated in vacuo. The residue was treated with ~50 mL of $Et_2O$ and sonicated for 2 min. The resulting suspension was filtered and air dried to afford ~1.7 g of a pale yellow solid. The mother liquor was concentrated to ~½ volume and filtered again to afford ~2.9 g of a tan solid, for a combined ~4.6 g of 6-bromo-3-morpholinoquinolin-2-amine.

Step 2:
A mixture of 6-bromo-3-morpholinoquinolin-2-amine (3.75 g, 12.17 mmol), 4,4,4',4',5,5,5',5'-octamethyl-2,2'-bi(1,3,2-dioxaborolane) (3.71 g, 14.60 mmol), dichloro 1,1'-bis(diphenylphosphino)ferrocene palladium (II) (0.497 g, 0.608 mmol), and potassium acetate (3.58 g, 36.5 mmol) under inert atmosphere in a 500 mL RBF was treated with dioxane (75 mL). The suspension was heated to 85° C. for 18 h. The reaction was concentrated in vacuo. The material was redissolved in EtOAc (300 mL) and filtered. The filtrate was concentrated in vacuo and the residue was suspended in 150 mL $Et_2O$. The precipitate was filtered to afford 2.75 g of a light brown solid. The filtrate was concentrated, suspended in 25 mL $Et_2O$ and filtered again to afford 0.78 g of an off-white solid. The solids were combined to give 3.53 g of 3-morpholino-6-(4,4,5,5-tetramethyl-1,3,2-dioxaborolan-2-yl)quinolin-2-amine.

Step 3:
A suspension of 2-(2-amino-3-morpholinoquinolin-6-yl)-3-methylbenzonitrile (0.038 g, 0.110 mmol) in THF (0.44 mL) was treated with a solution of phenylmagnesium chloride, 2M in THF (0.22 mL, 0.44 mmol) dropwise via syringe at ambient temperature. The mixture immediately formed an orange-brown solution which was warmed to 60° C. After 7 h at 60° C., reaction mixture was treated carefully with 1 mL 2N HCl (exothermic) and then allowed to cool to ambient temperature and stir overnight. The mixture was then concentrated in vacuo and taken up in 2.5 mL MeOH and purified by HPLC (10-90% $CH_3CN/H_2O$; TFA modifier). A single fraction was treated with $NH_4OH$, concentrated, filtered and air-dried to afford (2-(2-amino-3-morpholinoquinolin-6-yl)-3-ethylphenyl)(phenyl)methanone. MS (ESI, pos. ion) m/z: 424 (M+1).

Example 3

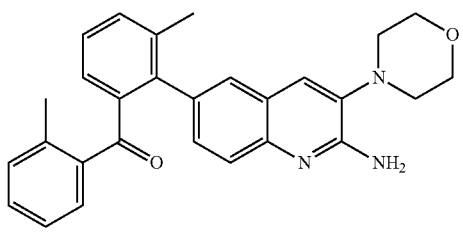 [SMILES: Cc1ccccc1C(=O)c1cccc(C)c1-c1ccc2nc(N)c(N3CCOCC3)cc2c1]

Synthesis of (2-(2-amino-3-morpholinoquinolin-6-yl)-3-methylphenyl)(o-tolyl)methanone Step 1:
A solution of 2-bromo-3-methylbenzonitrile (0.40 g, 2.04 mmol) in THF (2.04 mL) under inert atmosphere was cooled to 0° C. in an ice-water bath. A solution of o-tolylmagnesium bromide, ~2M in $Et_2O$ (1.22 mL, 2.45 mmol) was added dropwise via syringe. On completion of addition reaction mixture was allowed to warm to ambient temperature and then heated to 50° C. for 3 h. 2 mL of 2N aq. HCl was added carefully, the heating element was turned off and the reaction mixture allowed to be cooled to ambient temperature and stirred overnight. Then the reaction mixture was diluted with water (75 mL) and extracted with EtOAc (1×75 mL). The organic extract was washed with water (75 mL), saturated aqueous sodium bicarbonate (75 mL), and brine (75 mL) and dried over $MgSO_4$. The solution was filtered and concentrated in vacuo to give the crude material as a light-yellow oil. The crude material was purified by column chromatography eluting with a gradient of 5-50% $Et_2O$ in hexane, to provide (2-bromo-3-methylphenyl)(o-tolyl)methanone as a white solid.

Step 2:
A mixture of 2-dicyclohexylphosphino-2',4',6'-triisopropylbiphenyl (0.013 g, 0.028 mmol), (2-bromo-3-methylphenyl)(o-tolyl)methanone (0.16 g, 0.563 mmol), 3-morpholino-6-(4,4,5,5-tetramethyl-1,3,2-dioxaborolan-2-yl)quinolin-2-amine (0.050 g, 0.141 mmol), $Pd_2(dba)_3$ (6.44 mg, 7.04 µmol) were treated with dioxane (0.94 mL) and water (0.47 mL) in a medium-sized Smith synthesizer vial. The mixture was heated to 140° C. for 12 min in a microwave reactor. The reaction mixture was filtered then partitioned between EtOAc and water. The organic layer was washed with water and brine and then concentrated in vacuo. The crude product was purified first by column chromatography (1-10% MeOH:DCM) and then by HPLC (10-90% $CH_3CN/H_2O$; TFA modifier). A single fraction was treated with $NH_4OH$, concentrated, filtered and air-dried to afford (2-(2-amino-3-morpholinoquinolin-6-yl)-3-methylphenyl)(o-tolyl)methanone. MS (ESI, pos. ion) m/z: 438 (M+1).

Example 4

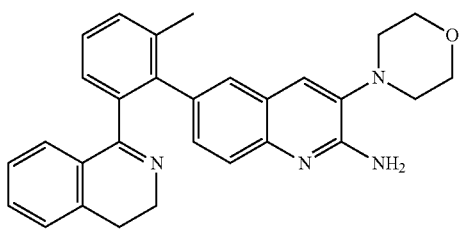 [SMILES: Cc1cccc(C2=NCCc3ccccc32)c1-c1ccc2nc(N)c(N3CCOCC3)cc2c1]

Synthesis of 6-(2-(3,4-dihydroisoquinolin-1-yl)-6-methylphenyl)-3-morpholinoquinolin-2-amine Step 1:
A suspension of 2-bromo-3-methylbenzoic acid (2.07 g, 9.63 mmol) in DCM (48.1 mL) was cooled to 0° C. Oxalyl chloride (0.9 mL, 10.14 mmol) was added dropwise via syringe. After addition, the cooling bath was removed and the reaction mixture stirred overnight. The mixture was concentrated in vacuo to remove solvent and excess reagent, affording 2-bromo-3-methylbenzoyl chloride as a cloudy white oil.

Step 2:
To a solution of 2-phenethylamine (0.28 mL, 2.195 mmol) in DCM (2.0 mL) was added 2-bromo-3-methylbenzoyl chloride (0.15 mL, 0.998 mmol) dropwise via syringe at ambient temperature. Mixture was allowed to stir overnight, then diluted with water (30 mL) and extracted with DCM (30 mL). The organic extract was washed with 1N HCl (2×25 mL) and 1N NaOH (2×25 mL) and dried over $MgSO_4$. The solution was filtered and concentrated in vacuo to give 2-bromo-3-methyl-N-phenethylbenzamide as a white solid.

Step 3:
Triflic anhydride (0.18 mL, 1.037 mmol) was added via syringe over 1 min to a stirred mixture of 2-bromo-3-methyl-N-phenethylbenzamide (0.30 g, 0.943 mmol) and 2-chloropyridine (0.11 mL, 1.131 mmol) in DCM (4.7 mL) at −78° C. The reaction mixture was stirred at −78° C. for 5 min, then placed in an ice-water bath and warmed to 0° C. After stirring another 5 min, the solution was allowed to warm to RT and then placed in a pre-heated block and stirred at 45° for 2 h. The reaction mixture was allowed to cool to RT, then it was diluted with 1N NaOH (3 mL) and extracted with DCM (15 mL). The organic extract was washed with saturated aqueous NaCl (2×15 mL) and dried over $Na_2SO_4$. The solution was filtered and concentrated in vacuo to give the crude material as a light-yellow oil. The crude material was absorbed onto a plug of silica gel and purified by column chromatography eluting with a gradient of 1-10% MeOH/DCM to provide 1-(2-bromo-3-methylphenyl)-3,4-dihydroisoquinoline as off-white glass.

Step 4:
A mixture of 3-morpholino-6-(4,4,5,5-tetramethyl-1,3,2-dioxaborolan-2-yl)quinolin-2-amine (0.18 g, 0.50 mmol), 1-(2-bromo-3-methylphenyl)-3,4-dihydroisoquinoline (0.10 g, 0.33 mmol), potassium phosphate (0.354 g, 1.67 mmol), 2-dicyclohexylphosphino-2',4',6'-triisopropylbiphenyl (0.032 g, 0.067 mmol) and $Pd_2$ $dba_3$ (0.015 g, 0.017 mmol) were treated with dioxane (2.22 mL) and Water (1.11 mL) in a medium-sized Smith synthesizer vial. The mixture was heated to 140° C. for 12 min in a microwave reactor. The reaction mixture was filtered then partitioned between EtOAc and water. The organic layers were washed with water and brine and then concentrated in vacuo. The crude product was purified by silica flash chromatography (1-10% MeOH:DCM) and then by HPLC (10-75% acetonitril/$H_2O$; TFA modifier). A single fraction was treated with $NH_4OH$, concentrated, filtered and air-dried to afford 6-(2-(3,4-dihydroisoquinolin-1-yl)-6-methylphenyl)-3-morpholinoquinolin-2-amine MS (ESI, pos. ion) m/z: 449 (M+1).

Example 5

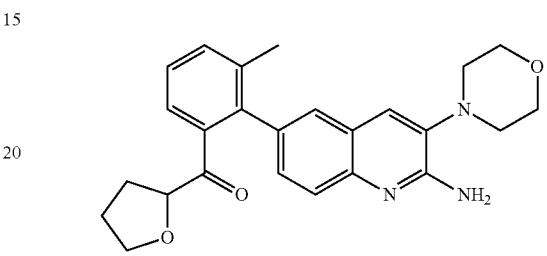

Synthesis of (2-(2-amino-3-morpholinoquinolin-6-yl)-3-methylphenyl) (tetrahydrofuran-2-yl)methanone Step 1:
A solution of 2-bromo-3-methylbenzoic acid (2.19 g, 10.18 mmol) in THF (20.37 mL) was treated with N,N'-carbonyldiimidazole (1.98 g, 12.2 mmol). The reaction mixture was stirred at ambient temperature overnight (14 h). Morpholine (3.11 mL, 35.6 mmol) was added in one portion. The resulting solution was stirred for 8 h and then partitioned between EtOAc and water. Organic layer washed with water, dilute HCl, saturated aqueous $Na_2CO_3$, water and brine. The solution was then concentrated in vacuo to afford (2-bromo-3-methylphenyl)(morpholino)methanone as a white crystalline solid.

Step 2:
A solution of 2,3-dihydrofuran (0.70 mL, 9.25 mmol) in THF (9.0 mL) under inert atmosphere was cooled to −78° C. A solution of n-butyllithium, 1.7 M in pentanes (5.98 mL, 10.17 mmol), was added dropwise over 10 min. The reaction was maintained at that temperature for 30 min, and allowed to warm to 0° C. for 30 min. It was cooled back down to −78° C. and then added via cannula to a solution of (2-bromo-3-methylphenyl)(morpholino)methanone (2.02 g, 7.12 mmol) in $Et_2O$ (17.92 mL), also at −78° C. The solution was stirred at that temperature for 10 min and then allowed to warm to 0° C. The mixture was partitioned between $Et_2O$ and water and the organics were washed with water and brine. The solution was dried over $Na_2SO_4$ and concentrated. The crude material was absorbed onto a plug of silica gel and purified by column chromatography eluting with a gradient of $Et_2O$ in hexane, to provide (2-bromo-3-methylphenyl)(4,5-dihydrofuran-2-yl) methanone as a colorless oil. This oil was immediately re-dissolved in $Et_2O$ and placed under nitrogen before storing in the freezer for further use.

Step 3:
A solution of (2-bromo-3-methylphenyl)(4,5-dihydrofuran-2-yl)methanone (0.80 g, 2.99 mmol) (mass approximate, based on ~8 mg/mL $Et_2O$ solution) was treated with 500 mL EtOAc and concentrated to ~100 mL twice. The resulting solution was placed under N$_2$ atmosphere, treated with 5% Pt/C, and then placed under a balloon of H$_2$. Reaction mixture was allowed to stir overnight, then filtered through plug of celite and the filter agent was further washed with 100 mL EtOAc. The solution was concentrated in vacuo and the crude material was absorbed onto a plug of silica gel and purified by column chromatography eluting with a gradient of 20-100% Et$_2$O in hexane to afford (2-bromo-3-methylphenyl)(tetrahydrofuran-2-yl)methanone.

Step 4:

A mixture of 3-morpholino-6-(4,4,5,5-tetramethyl-1,3,2-dioxaborolan-2-yl)quinolin-2-amine (0.099 g, 0.279 mmol), (2-bromo-3-methylphenyl)(tetrahydrofuran-2-yl)methanone (0.050 g, 0.186 mmol), potassium phosphate tribasic (0.077 mL, 0.929 mmol), 2-dicyclohexylphosphino-2',4',6'-triisopropylbiphenyl (0.018 g, 0.037 mmol), and Pd$_2$(dba)$_3$ (8.51 mg, 9.29 μmol) were treated with dioxane (1.2 mL) and water (0.62 mL) in a medium-sized Smith synthesizer vial. The mixture was heated to 140° C. for 12 min in a microwave reactor. The reaction mixture was filtered then partitioned between EtOAc and water, organics were washed with water and brine and then concentrated in vacuo. The crude product was purified by silica flash chromatography (1-10% MeOH/DCM) and then by HPLC (10-75% acetonitril/H$_2$O; TFA modifier). A single fraction was treated with NH$_4$OH, concentrated, filtered and air-dried to afford (2-(2-amino-3-morpholinoquinolin-6-yl)-3-methylphenyl)(tetrahydrofuran-2-yl)methanone. MS (ESI, pos. ion) m/z: 418 (M+1).

Example 6

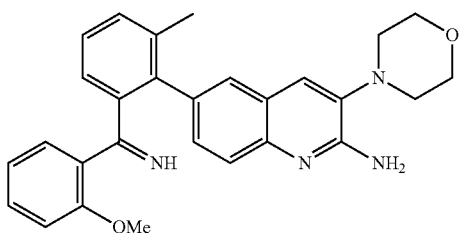 [SMILES: COc1ccccc1C(=N)c1cccc(C)c1-c1ccc2nc(N)c(N3CCOCC3)cc2c1]

Synthesis of 6-(2-(imino(2-methoxyphenyl)methyl)-6-methylphenyl)-3-morpholinoquinolin-2-amine To a solution of isopropylmagnesium chloride, 2.0 M in THF (0.46 mL, 0.92 mmol) under inert atmosphere in a dry conical Smith synthesizer vial was added 2-iodoanisole (0.10 mL, 0.77 mmol) dropwise. A portion of this solution (0.25 mL) was taken up in a syringe and added to a sealed vessel containing 2-(2-amino-3-morpholinoquinolin-6-yl)-3-methylbenzonitrile (0.038 g, 0.11 mmol) under inert atmosphere at ambient temperature. The mixture was sonicated until all solids were in solution and then the vessel was warmed to 60° C. After 5 h at 60° C., the reaction mixture was treated carefully with 1 mL 2N HCl (exotherm!) and then stirred for 4 h at this temperature and allowed to cool to ambient temperature and stir overnight. Mixture was then concentrated in vacuo and taken up in 2.5 mL MeOH and purified by HPLC (10-90% acetonitrile/H$_2$O; TFA modifier). The clean fractions were combined and concentrated in vacuo then eluted on a SCX column. The basic fraction was concentrated to afford: 6-(2-(imino(2-methoxyphenyl)methyl)-6-methylphenyl)-3-morpholinoquinolin-2-amine. MS (ESI, pos. ion) m/z: 453 (M+1).

Example 7

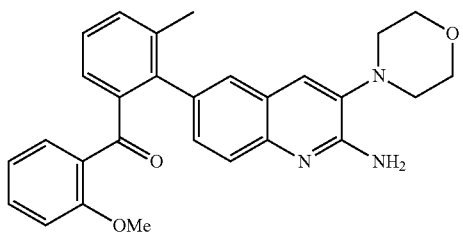 [SMILES: COc1ccccc1C(=O)c1cccc(C)c1-c1ccc2nc(N)c(N3CCOCC3)cc2c1]

Synthesis of (2-(2-amino-3-morpholinoquinolin-6-yl)-3-methylphenyl)(2-methoxyphenyl)methanone A solution of 6-(2-(imino(2-methoxyphenyl)methyl)-6-methylphenyl)-3-morpholinoquinolin-2-amine (0.022 g, 0.049 mmol) in 5N aq. HCl (2 mL) was heated to 100° C. in a sealed tube for 16 h, then allowed to cool to 50° C. and heated for another 70 h at that temperature. The mixture was neutralized with 10N NaOH and filtered. The precipitate was redissolved in MeOH and purified by reverse-phase HPLC (10-90% acetonitrile/H$_2$O, TFA modifier). A single fraction was treated with NH$_4$OH and the acetonitrile was removed in vacuo. The resulting suspension was filtered and air-dried to afford (2-(2-amino-3-morpholinoquinolin-6-yl)-3-methylphenyl)(2-methoxyphenyl)methanone. MS (ESI, pos. ion) m/z: 454 (M+1).

Example 8

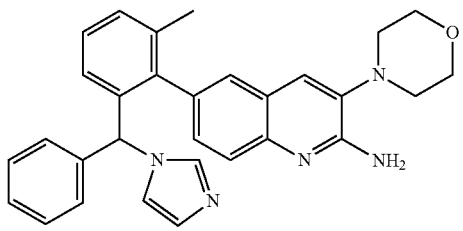 [SMILES: Cc1cccc(C(c2ccccc2)n2ccnc2)c1-c1ccc2nc(N)c(N3CCOCC3)cc2c1]

Synthesis of 6-(2-((1H-imidazol-1-yl)(phenyl)methyl)-6-methylphenyl)-3-morpholinoquinolin-2-amine Step 1:

(2-(2-Amino-3-morpholinoquinolin-6-yl)-3-methylphenyl)(phenyl)methanone (0.152 g, 0.359 mmol) was dissolved in a mixture of DCM (4.0 mL) and MeOH (5.0 mL). Sodium borohydride (0.041 g, 1.077 mmol) was added to the mixture in three portions (each portion added at 3 h intervals) and the mixture was stirred at ambient temperature. The mixture was treated with DCM (10 mL) and saturated aqueous bicarbonate (10 mL) and stirred for 20 min. The phases were separated and the organic layer was concentrated to afford a yellow solid (2-(2-amino-3-morpholinoquinolin-6-yl)-3-methylphenyl)(phenyl)methanol which was used without further purification.

Step 2:

A solution of (2-(2-amino-3-morpholinoquinolin-6-yl)-3-methylphenyl)(phenyl)methanol (0.155 g, 0.364 mmol) in DCM was treated with 0.4 mL of 5N HCl in iPrOH. The mixture was concentrated in vacuo and azeotroped 3× with DCM. The resulting yellow solid was treated again with DCM (1.21 mL) and thionyl chloride (0.80 mL, 10.93 mmol) was added dropwise, and the reaction mixture was stirred for 30 min at ambient temperature for 1 h and concentrated in vacuo. The residue was azeotroped 2× with DCM and dried under vacuum to afford crude 6-(2-(chloro(phenyl)methyl)-6-methylphenyl)-3-morpholinoquinolin-2-amine hydrochloride which was used without further purification.

Step 3:

In a small, sealed Smith synthesizer vial, 6-(2-(chloro(phenyl)methyl)-6-methylphenyl)-3-morpholinoquinolin-2-amine hydrochloride (0.030 g, 0.062 mmol) and imidazole (0.021 g, 0.312 mmol) were treated with ACN (0.416 mL). The solution was stirred at ambient temperature for 1 h. The reaction mixture was warmed to 100° C. for 1 h and then allowed to cool to ambient temperature. The mixture was purified by HPLC (1-70% acetonitrile/H₂O, TFA modifier). A single clean fraction was treated with NH₄OH and concentrated to ¼ volume. The resulting precipitate was collected and dried under a stream of N₂ to afford 6-(2-((1H-imidazol-1-yl)(phenyl)methyl)-6-methylphenyl)-3-morpholinoquinolin-2-amine. MS (ESI, pos. ion) m/z: 476 (M+1).

Example 9

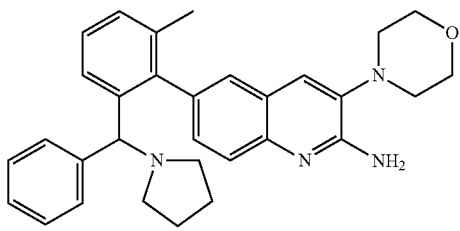 [SMILES: Cc1cccc(C(c2ccccc2)N2CCCC2)c1-c1ccc2nc(N)c(N3CCOCC3)cc2c1]

Synthesis of 6-(2-methyl-6-(phenyl(pyrrolidin-1-yl)methyl)phenyl)-3-morpholinoquinolin-2-amine A Smith synthesizer vial containing 6-(2-(chloro(phenyl)methyl)-6-methylphenyl)-3-morpholinoquinolin-2-amine hydrochloride (0.050 g, 0.104 mmol) and ACN (0.42 mL) was treated with pyrrolidine (0.052 mL, 0.624 mmol). The reaction mixture was warmed to 100° C. for 1 h and then allowed to cool to RT. The mixture was purified by HPLC (1-70% ACN/H₂O, TFA modifier). A single clean fraction was treated with NH₄OH and concentrated to ¼ volume. The resulting precipitate was collected and dried under a stream of N₂ to afford 6-(2-methyl-6-(phenyl(pyrrolidin-1-yl)methyl)phenyl)-3-morpholinoquinolin-2-amine. MS (ESI, pos. ion) m/z: 479 (M+1).

Example 10

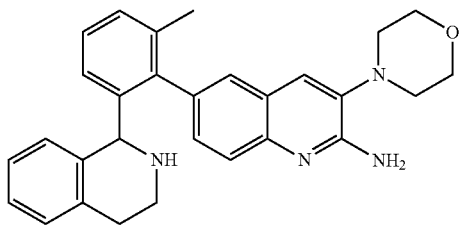 [SMILES: Cc1cccc(C2NCCc3ccccc32)c1-c1ccc2nc(N)c(N3CCOCC3)cc2c1]

Synthesis of 6-(2-methyl-6-(1,2,3,4-tetrahydroisoquinolin-1-yl)phenyl)-3-morpholinoquinolin-2-amine A suspension of 6-(2-(3,4-dihydroisoquinolin-1-yl)-6-methylphenyl)-3-morpholinoquinolin-2-amine (0.0075 g, 0.017 mmol) in MeOH (0.50 mL) was treated with NaBH₄ (25.0 mg, 0.661 mmol) and stirred at ambient temperature overnight. On following day, reaction mixture treated with 2N HCl and stirred for 2 h. The mixture was filtered and the filtrate was purified directly by reverse phase HPLC (1-90% acetonitrile/H₂O, TFA modifier, 20 min). Single fraction freeze-dried to afford 6-(2-methyl-6-(1,2,3,4-tetrahydroisoquinolin-1-yl)phenyl)-3-morpholinoquinolin-2-amine (2,2,2-trifluoroacetate salt). MS (ESI, pos. ion) m/z: 451 (M+1).

Example 11

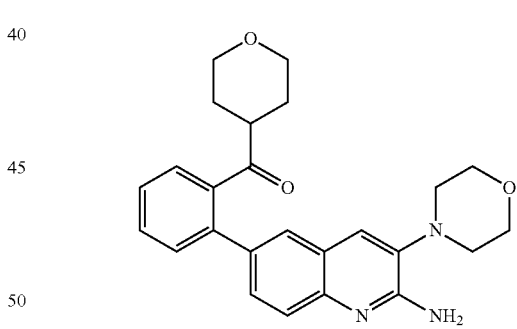

Synthesis of (2-(2-amino-3-morpholinoquinolin-6-yl)phenyl)(tetrahydro-2H-pyran-4-yl)methanone Step 1:

Lithium chloride (0.16 mL, 7.8 mmol) and copper cyanide (0.12 mL, 3.9 mmol) were dissolved in dry THF (4 mL) under nitrogen. This was added dropwise to pentamethylenebis(magnesium bromide) (0.5 M in THF, 7.79 mL, 3.9 mmol) in a dry ice bath under nitrogen and the mixture stirred for 30 min. I-Bromo-2-iodobenzene (0.50 mL, 3.9 mmol) was added and the flask was removed from the cold bath. After 30 min additional dry THF (5 mL) was added and stirred for another 40 min. Then tetrahydro-2H-pyran-4-carbonyl chloride (0.58 mL, 3.9 mmol) was added in one portion, and the mixture was stirred for 15 min. The reaction was quenched by addition of saturated ammonium chloride (10 mL). Ethyl acetate (100 mL) and water (100 mL) were added and the phases were mixed and separated. The organic layer was separated, dried with magnesium sulfate and evaporated to dryness under reduced pressure. Purification using silica column chromatography (hexane to ethyl acetate gradient) gave (2-bromophenyl)(tetrahydro-2H-pyran-4-yl)methanone as a thick oil.

Step 2:

(2-Bromophenyl)(tetrahydro-2H-pyran-4-yl)methanone (0.46 g, 1.69 mmol), 3-morpholino-6-(4,4,5,5-tetramethyl-1,3,2-dioxaborolan-2-yl)quinolin-2-amine (0.50 g, 1.13 mmol, prepared as in Example 2, Step 1-2), potassium phosphate tribasic (0.37 mL, 4.50 mmol), 2-dicyclohexylphosphino-2',4',6',-triisopropylbiphenyl (0.054 g, 0.113 mmol), and tris(dibenzylideneacetone)dipalladium (0) chloroform adduct (0.029 g, 0.028 mmol) were suspended in a mixture of dioxane (3 mL) and water (0.5 mL) and heated in the microwave to 120° C. for 30 min. The crude material was partitioned between water (100 mL) and ethyl acetate (200 mL). The organic layer was separated, dried with magnesium sulfate and evaporated to dryness under reduced pressure before purification using silica column chromatography (0-5% MeOH in DCM). The isolated material was further purified using silica column chromatography (60-100% ethyl acetate in hexane) to give (2-(2-amino-3-morpholinoquinolin-6-yl)phenyl)(tetrahydro-2H-pyran-4-yl)methanone. MS (ESI, pos. ion) m/z: 418 (M+1).

Example 12

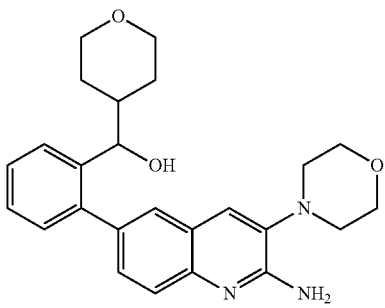 [SMILES: Nc1nc2ccc(-c3ccccc3C(O)C3CCOCC3)cc2cc1N1CCOCC1]

Synthesis of (2-(2-amino-3-morpholinoquinolin-6-yl)phenyl)(tetrahydro-2H-pyran-4-yl)methanol (2-(2-Amino-3-morpholinoquinolin-6-yl)phenyl)(tetrahydro-2H-pyran-4-yl)methanone (0.164 g, 0.393 mmol, see Example 11) was dissolved in MeOH (20 mL) and treated with sodium borohydride (0.021 mL, 0.589 mmol). After 10 min, the solution was heated to 40° C. for an additional 15 minutes, then evaporated to dryness under reduced pressure. The crude material was partitioned between water (20 mL), saturated sodium bicarbonate (20 mL), and ethyl acetate (40 mL). The organic layer was dried with magnesium sulfate and evaporated to dryness under reduced pressure and the crude material was purified by silica chromatography (10-100% hexane in ethyl acetate gradient. The product peak which eluted was concentrated to give (2-(2-amino-3-morpholino-quinolin-6-yl)phenyl)(tetrahydro-2H-pyran-4-yl)methanol. MS (ESI, pos. ion) m/z: 420 (M+1).

Example 13

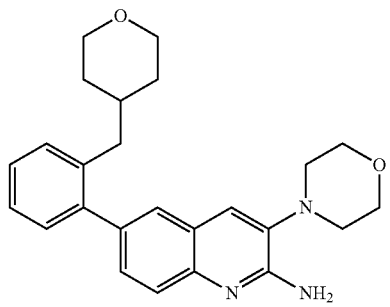 [SMILES: Nc1nc2ccc(-c3ccccc3CC3CCOCC3)cc2cc1N1CCOCC1]

Synthesis of 3-morpholino-6-(2-((tetrahydro-2H-pyran-4-yl)methyl)phenyl)quinolin-2-amine (2-(2-Amino-3-morpholinoquinolin-6-yl)phenyl)(tetrahydro-2H-pyran-4-yl)methanol (0.085 g, 0.203 mmol, see Example 12) was dissolved in DCM (20 mL) and treated with triethylsilane (1.0 mL, 6.26 mmol) and TFA (2.0 mL, 26.9 mmol). The mixture was heated to 70° C. for 30 min after which analysis showed the reduction was complete. The solution was evaporated to dryness under reduced pressure. The crude was partitioned between water (10 mL), saturated sodium bicarbonate (10 mL) and DCM (20 mL). The organic layer was dried with magnesium sulfate and evaporated to dryness under reduced pressure. Purification using silica chromatography (0-10% methanol in DCM gradient) gave the desired 3-morpholino-6-(2-((tetrahydro-2H-pyran-4-yl)methyl)phenyl)quinolin-2-amine. MS (ESI, pos. ion) m/z: 404 (M+1).

Example 14

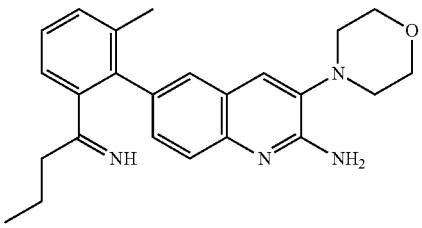 [SMILES: CCCC(=N)c1cccc(C)c1-c1ccc2nc(N)c(N3CCOCC3)cc2c1]

Synthesis of 6-(2-(1-iminobutyl)-6-methylphenyl)-3-morpholinoquinolin-2-amine

Step 1:

To a mixture of potassium phosphate (5.98 g, 28.2 mmol), dicyclohexyl(2',4',6'-triisopropylbiphenyl-2-yl)phosphine (0.54 g, 1.13 mmol), Pd$_2$(dba)$_3$ (0.26 g, 0.28 mmol), 2-bromo-3-methylbenzonitrile (2.21 g, 11.26 mmol) and 3-morpholino-6-(4,4,5,5-tetramethyl-1,3,2-dioxaborolan-2-yl)quinolin-2-amine (2.00 g, 5.63 mmol, prepared as in Example 2, Step 1-2) was added dioxane (50.0 mL) and water (25.0 mL). The mixture was heated to 140° C. for 10 min. The reaction mixture was allowed to cool to RT, filtered and then partitioned between EtOAc and water. The organic layer was washed with water and brine, and concentrated. The residue was diluted with EtOAc and then filtered. The solid was dried in air to afford 2-(2-amino-3-morpholinoquinolin-6-yl)-3-methylbenzonitrile as a light brown solid.

Step 2:

To a sealed vessel containing 2-(2-amino-3-morpholinoquinolin-6-yl)-3-methylbenzonitrile (0.040 g, 0.116 mmol) under $N_2$ atmosphere was added a solution of propylmagnesium bromide, 2.0M in THF (0.232 mL, 0.465 mmol) via syringe at ambient temperature. The mixture was sonicated until all solids were in solution and then warmed vessel to 60° C. for 7 h. The mixture was concentrated, diluted with MeOH and purified on HPLC (10-100% MeCN/$H_2O$ with 0.1% TFA modifier) to afford 6-(2-(1-iminobutyl)-6-methylphenyl)-3-morpholinoquinolin-2-amine as white solid. MS (ESI, pos. ion) m/z: 389 (M+1).

Example 15

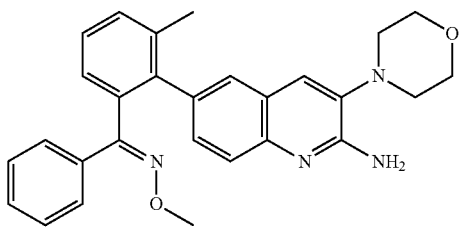 [SMILES: CO/N=C(\c1ccccc1)c1cccc(C)c1-c1ccc2nc(N)c(N3CCOCC3)cc2c1]

Synthesis of (2-(2-amino-3-morpholinoquinolin-6-yl)-3-methylphenyl)(phenyl)methanone O-methyl oxime Step 1:

To a sealed tube containing 2-(2-amino-3-morpholinoquinolin-6-yl)-3-methylbenzonitrile (0.20 g, 0.581 mmol, prepared as in Example 14, Step 1) was added phenylmagnesium chloride, 2.0M solution in THF (1.16 mL, 2.323 mmol) under $N_2$ atmosphere. The mixture was heated at 60° C. overnight and the conversion was completed, determined by LCMS. The mixture was allowed to cool to RT and treated with aqueous 2N HCl (1 ml) carefully. The resulted mixture was heated at 60° C. for 7 h until the imine was consumed. The product mixture was concentrated and then diluted with MeOH and purified on HPLC (10-100% MeCN/$H_2O$ with 0.1% TFA modifier) to afford (2-(2-amino-3-morpholinoquinolin-6-yl)-3-methylphenyl)(phenyl)methanone (TFA salt).

Step 2:

To a solution of (2-(2-amino-3-morpholinoquinolin-6-yl)-3-methylphenyl)(phenyl)methanone (0.090 g, 0.213 mmol) in MeOH (4.0 mL) was added methoxylamine hydrochloride, 98% (0.089 g, 1.063 mmol) followed by 3 drops of pyridine. The reaction mixture was brought up to reflux for 41 h until the conversion was completed, as determined by LCMS. The reaction mixture was cooled to RT and purified on HPLC (10-100% MeCN/$H_2O$ with 0.1% TFA) to afford (2-(2-amino-3-morpholinoquinolin-6-yl)-3-methylphenyl)(phe-nyl)methanone O-methyl oxime as a off-white solid. MS (ESI, pos. ion) m/z: 453 (M+1).

Example 16

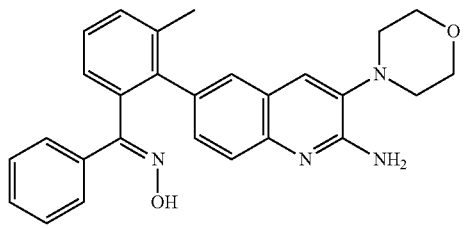 [SMILES: Cc1cccc(/C(=N/O)c2ccccc2)c1-c1ccc2nc(N)c(N3CCOCC3)cc2c1]

Synthesis of (2-(2-amino-3-morpholinoquinolin-6-yl)-3-methylphenyl)(phenyl)methanone oxime To a solution of (2-(2-amino-3-morpholinoquinolin-6-yl)-3-methylphenyl)(phenyl)methanone (0.090 g, 0.213 mmol, prepared as Example 15, Step 1) in MeOH (4.0 mL) was added hydroxyammonium chloride (0.044 mL, 1.063 mmol) followed by 3 drops of pyridine. The reaction mixture was brought up to reflux for 41 h until the conversion was completed, determined by LCMS. The reaction mixture was cooled to RT and purified on HPLC (10-100% MeCN/$H_2O$ with 0.1% TFA) to afford (2-(2-amino-3-morpholinoquinolin-6-yl)-3-methylphenyl)(phenyl)methanone oxime as a off-white solid. MS (ESI, pos. ion) m/z: 439 (M+1).

Example 17

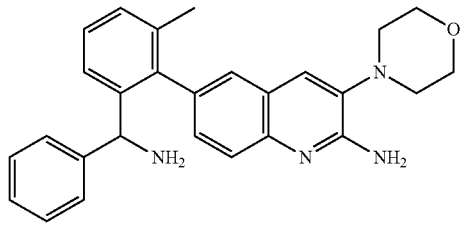 [SMILES: Cc1cccc(C(N)c2ccccc2)c1-c1ccc2nc(N)c(N3CCOCC3)cc2c1]

Synthesis of 6-(2-(amino(phenyl)methyl)-6-methylphenyl)-3-morpholinoquinolin-2-amine Step 1:

To a sealed vessel containing 2-(2-amino-3-morpholinoquinolin-6-yl)-3-methylbenzonitrile (0.10 g, 0.290 mmol, prepared as in Example 14, Step 1) was added phenylmagnesium chloride, 2.0M solution in THF (0.58 mL, 1.161 mmol). The mixture was sonicated until all solids were in solution and then warmed vessel to 60° C. for 15 h. The reaction mixture was cooled to RT and divided into two portions. The imine solution was concentrated in vacuo. The residue was taken up in 2.5 mL MeOH and purified by HPLC (10-100% MeCN/$H_2O$ with 0.1% TFA modifier) to afford 6-(2-(imino(phenyl)methyl)-6-methylphenyl)-3-morpholinoquinolin-2-amine.

Step 2:

To a cooled (ice bath) solution of 6-(2-(imino(phenyl)methyl)-6-methylphenyl)-3-morpholinoquinolin-2-amine (0.058 g, 0.137 mmol) in MeOH (5.0 mL) was added sodium borohydride, 99% (0.033 mL, 0.925 mmol). The mixture was then warmed to RT and stirred for 1 h. The excess NaBH$_4$ was then treated with acetone. The resulted solution was concentrated and purified on HPLC (10-100% MeCN/H$_2$O with 0.1% TFA modifier) to afford 6-(2-(amino(phenyl)methyl)-6-methylphenyl)-3-morpholinoquinolin-2-amine as white solid. MS (ESI, pos. ion) m/z: 425 (M+1).

Example 18

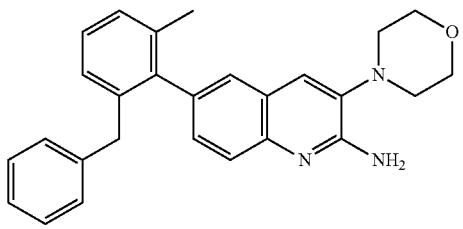 [SMILES: Cc1cccc(Cc2ccccc2)c1-c1ccc2nc(N)c(N3CCOCC3)cc2c1]

Synthesis of 6-(2-benzyl-6-methylphenyl)-3-morpholinoquinolin-2-amine

Step 1:
To a cooled (ice bath) solution of (2-(2-amino-3-morpholinoquinolin-6-yl)-3-methylphenyl)(phenyl)methanone (0.246 g, 0.581 mmol, prepared as in Example 15, Step 1) in MeOH (10.0 mL) was added sodium tetrahydroborate (0.044 g, 1.162 mmol) in one portion. The reaction mixture was then allowed to warm to RT and stirred for 17 h (overnight). Additional 4 eq of NaBH$_4$ was added and stirred for 7 h until the conversion was completed, determined by LCMS. Acetone was added to quench the excess NaBH$_4$. The resulted solution was concentrated and dried in vacuum to afford crude (2-(2-amino-3-morpholinoquinolin-6-yl)-3-methylphenyl) (phenyl)methanol as light yellow solid which was used without further purification.

Step 2:
A mixture of (2-(2-amino-3-morpholinoquinolin-6-yl)-3-methylphenyl)(phenyl)methanol (0.245 g, 0.576 mmol) and palladium hydroxide, 20 wt % Pd (dry basis) on carbon, wet (0.380 g, 2.71 mmol) in ethanol (15 mL) and ethyl acetate (5.0 mL) was stirred under H$_2$ balloon overnight. 400 mg more Pd(OH)$_2$ was added and stirred for 72 h. The product mixture was filtered through a pad of celite. The filtrate was concentrated and purified on HPLC (10-100% MeCN/H$_2$O with 0.1% TFA) to afford 6-(2-benzyl-6-methylphenyl)-3-morpholinoquinolin-2-amine as white solid. MS (ESI, pos. ion) m/z: 410 (M+1).

Example 19

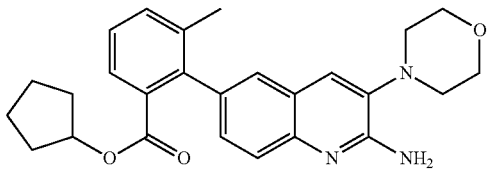 [SMILES: Cc1cccc(C(=O)OC2CCCC2)c1-c1ccc2nc(N)c(N3CCOCC3)cc2c1]

Synthesis of cyclopentyl 2-(2-amino-3-morpholinoquinolin-6-yl)-3-methylbenzoate

Step 1:
2-Bromo-3-methylbenzoic acid (1.48 g, 6.88 mmol) was dissolved in thionyl chloride (20 mL, 274 mmol) and heated to reflux for 30 min. The solution was evaporated to dryness under reduced pressure and further dried under high vacuum to give the acid chloride as a clear oil. It was dissolved in DCM (10 mL) and slowly added to a solution of cyclopentanol (1.00 mL, 11.02 mmol) and DIEA (2.0 mL, 11.50 mmol) in dry THF (40 mL) in an ice bath. The reaction was stirred for 30 min then evaporated to dryness under reduced pressure. The crude was redissolved in DCM (60 mL) and washed with water (100 mL) followed by 1N HCl (70 mL) and 1N NaOH (60 mL). The organic layer was dried on magnesium sulfate and evaporated to dryness. The crude material was purified using silica chromatography (hexane to DCM gradient) to give cyclopentyl 2-bromo-3-methylbenzoate as a clear oil.

Step 2:
3-Morpholino-6-(4,4,5,5-tetramethyl-1,3,2-dioxaborolan-2-yl)quinolin-2-amine (0.15 g, 0.422 mmol, prepared as Example 2, Step 1-2), cyclopentyl 2-bromo-3-methylbenzoate (0.133 g, 0.470 mmol), potassium acetate (0.079 mL, 1.267 mmol), 2-dicyclohexylphosphino-2',4',6',-triisopropylbiphenyl (0.020 g, 0.042 mmol), palladium(II) acetate (4.74 mg, 0.021 mmol), water (0.3 mL) and ethanol (2 mL) were combined in a microwave vial and heated to 145° C. for 30 min. The crude material was partitioned between water (40 mL) and DCM (50 mL). The organic layer was dried on magnesium sulfate, filtered and concentrated. The crude material was purified by silica chromatography (0-10% methanol in DCM gradient) to give cyclopentyl 2-(2-amino-3-morpholinoquinolin-6-yl)-3-methylbenzoate. MS (ESI, pos. ion) m/z: 432 (M+1).

Example 20

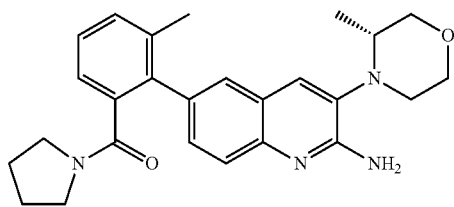 [SMILES: Cc1cccc(C(=O)N2CCCC2)c1-c1ccc2nc(N)c(N3CCOC[C@H]3C)cc2c1]

Synthesis of (R)-(2-(2-amino-3-(3-methylmorpholino)quinolin-6-yl)-3-methylphenyl)(pyrrolidin-1-yl)methanone Step 1:
To a solution of (R)-2-amino-1-propanol (5.18 mL, 66.6 mmol) in THF (20 mL) was added Hunig's base (11.63 mL, 66.6 mmol) and chloroacetyl chloride (5.87 mL, 73.2 mmol) and the mixture was stirred at RT until the starting material was consumed (~1.5 h). The mixture was washed with sat NH$_4$Cl (3×). The aqueous phase was extracted with 3:1 CH$_3$Cl/iPrOH and the combined organics were dried over Na$_2$SO$_4$, filtered, and concentrated to afford a yellow oil. This oil was dissolved in THF (20 mL) followed by the slowly addition of NaH (3.20 g, 80 mmol) and stirred for 3 h. The mixture was quenched with a few drops of water, concentrated, and chromatographed on silica gel to afford (R)-5-methylmorpholin-3-one as a light brown oil.

Step 2:

A mixture of 6-bromo-3-iodo-N-(4-methoxybenzyl) quinolin-2-amine (0.25 g, 0.533 mmol, prepared as in Example 1, Step 1-2), 2-isobutyrylcyclohexanone (0.018 g, 0.107 mmol), (R)-5-methylmorpholin-3-one (0.92 g, 7.99 mmol), copper(I) iodide (5.07 mg, 0.027 mmol), and cesium carbonate (0.35 g, 1.066 mmol) in DMF (5 mL) was heated at 125° C. for 10 min. Some product was observed but mostly starting material. The mixture was heated again at 125° C. for 10 min more. This process was repeated 7× until the starting material was completely consumed. The reaction was brought to RT, poured into water (20 mL) and extracted with EtOAc. The combined organics were dried over $Na_2SO_4$, filtered, concentrated, and chromatographed on silica gel using gradient 2:1 hexanes/EtOAc to afford a light yellow solid as (R)-4-(6-bromo-2-(4-methoxybenzylamino)quinolin-3-yl)-5-methylmorpholin-3-one.

Step 3:

To a solution of (R)-4-(6-bromo-2-(4-methoxybenzylamino)-quinolin-3-yl)-5-methylmorpholin-3-one (0.11 g, 0.241 mmol) in THF (5 mL) was added borane tetrahydrofuran complex, 1.0M in THF (0.482 mL, 0.482 mmol) and the resulting mixture was refluxed for 1 h. Some of the borane-amine complex was observed. The mixture was brought at RT, concentrated and dissolved in MeOH. The mixture was purged with $N_2$ followed by the addition of Pd/C and stirred at RT for 20 min until no more complex was observed. The mixture was filtered through celite and concentrated to give (R)-6-bromo-N-(4-methoxybenzyl)-3-(3-methylmorpholino)quinolin-2-amine that was used without purification.

Step 3:

A mixture of (R)-6-bromo-N-(4-methoxybenzyl)-3-(3-methylmorpholino) quinolin-2-amine (0.064 g, 0.145 mmol), $PdCl_2(dppf)\text{-}CH_2Cl_2$ adduct (5.91 mg, 7.23 μmol), bis(pinacolato)diboron (0.044 g, 0.174 mmol), and potassium acetate (0.027 mL, 0.434 mmol) was purged with $N_2$ for 10 min followed by the addition of dioxane (degassed with $N_2$, 2 mL). The resulting mixture was heated at 85° C. for 16 h. The reaction went to completion, concentrated and then diluted with EtOAc and filtered. The solvent was removed to afford (R)—N-(4-methoxybenzyl)-3-(3-methylmorpholino)-6-(4,4,5,5-tetramethyl-1,3,2-dioxaborolan-2-yl)quinolin-2-amine that was used without purification.

Step 4:

A mixture of (2-bromo-3-methylphenyl)(pyrrolidin-1-yl)methanone (0.115 g, 0.429 mmol), (R)—N-(4-methoxybenzyl)-3-(3-methylmorpholino)-6-(4,4,5,5-tetramethyl-1,3,2-dioxaborolan-2-yl)quinolin-2-amine (0.07 g, 0.143 mmol), potassium phosphate, anhydrous (0.121 g, 0.572 mmol), 2-(dicyclohexylphosphino)-2',4',6',-tri-1-propyl-1,1'-biphenyl (0.014 g, 0.029 mmol), and $Pd_2(dba)_3$ (0.013 g, 0.014 mmol) was purged with $N_2$ followed by the addition of degassed dioxane (1 mL) and degassed water (0.5 mL). The resulting mixture was heated in microwave at 140° C. for 12 min. The reaction went to completion and it was filtered, concentrated, and chromatographed on silica gel using 0-5% MeOH/DCM to afford a yellow oil. To the product was added TFA (10 mL, 130 mmol) and the solution was heated at 60° C. for 18 h until the starting material was consumed. The mixture was concentrated and chromatographed on silica gel using 0-5% 2 M $NH_3$ in MeOH/DCM to afford a yellow solid as (R)-(2-(2-amino-3-(3-methylmorpholino)quinolin-6-yl)-3-methylphenyl)(pyrrolidin-1-yl)methanone. MS (ESI, pos. ion) m/z: 431 (M+1).

Example 21

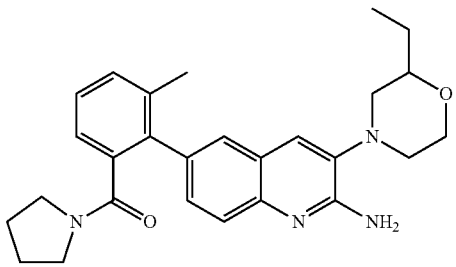 [SMILES: CCC1CN(c2cc3cc(-c4c(C)cccc4C(=O)N4CCCC4)ccc3nc2N)CCO1]

Synthesis of (2-(2-amino-3-(2-ethylmorpholino)quinolin-6-yl)-3-methylphenyl)(pyrrolidin-1-yl)methanone Step 1:

To 1-(benzyl(2-hydroxyethyl)amino)butan-2-ol (2.9 g, 12.99 mmol) was added 70% $H_2SO_4$ (15 mL) and the resulting solution was heated at 140° C. for 17 h. The mixture was brough to RT, cooled to 0° C. and made alkaline with 50% NaOH. The resulting solution was diluted in water and extracted with DCM. The combined organics were dried over $Na_2SO_4$, filtered and concentrated to afford 4-benzyl-2-ethylmorpholine as a light orange oil that was used without further purification.

Step 2:

Through suspension of 4-benzyl-2-ethylmorpholine (5 g, 24.36 mmol) and palladium hydroxide on carbon (3.42 g, 24.36 mmol) in EtOH (50 mL) was bubbled $H_2$ through a balloon for 17 h. Some starting material was observed. The mixture was filtered through celite and the solvent was removed by distillation to afford a light yellow oil as 2-ethylmorpholine that was used without purification.

Step 3:

A mixture of 6-bromo-3-iodo-N-(4-methoxybenzyl) quinolin-2-amine (0.30 g, 0.640 mmol, prepared as in Example 1, Step 1-2), 2-ethylmorpholine (1.105 g, 9.59 mmol), copper(I) iodide (6.09 mg, 0.032 mmol), cesium carbonate (0.417 g, 1.279 mmol), and 2-isobutyrylcyclohexanone (0.021 mL, 0.128 mmol) in DMF (3 mL) was heated at 125° C. for 10 min. Some product was observed but mostly starting material. The mixture was heated again at 125° C. for 10 min more. This process was repeated 3× until the starting material was completely consumed. The reaction was brought to RT, poured into water (20 mL) and extracted with EtOAc. The combined organics were dried over $Na_2SO_4$, filtered, concentrated, and chromatographed on silica gel using gradient 2:1 hexanes/EtOAc to afford a brown oil as 6-bromo-3-(2-ethylmorpholino)-N-(4-methoxybenzyl) quinolin-2-amine.

Step 4:

A mixture of 6-bromo-3-(2-ethylmorpholino)-N-(4-methoxybenzyl)quinolin-2-amine (0.16 g, 0.351 mmol), $PdCl_2$(dppf)-$CH_2Cl_2$adduct (0.014 g, 0.018 mmol), bis(pinacolato) diboron (0.107 g, 0.421 mmol), and potassium acetate (0.066 mL, 1.052 mmol) was purged with $N_2$ for 10 min followed by the addition of dioxane (degassed with $N_2$, 2 mL). The resulting mixture was heated at 85° C. for 16 h. The reaction went to completion, concentrated and then diluted with EtOAc and filtered. The solvent was removed to afford 3-(2-ethylmorpholino)-N-(4-methoxybenzyl)-6-(4,4,5,5-tetramethyl-1,3,2-dioxaborolan-2-yl)quinolin-2-amine that was used without further purification.

Step 5:
A mixture of (2-bromo-3-methylphenyl)(pyrrolidin-1-yl)methanone (0.256 g, 0.953 mmol), 3-(2-ethylmorpholino)-N-(4-methoxybenzyl)-6-(4,4,5,5-tetramethyl-1,3,2-dioxaborolan-2-yl)quinolin-2-amine (0.16 g, 0.318 mmol), 2-(dicyclohexylphosphino)-2',4',6',-tri-1-propyl-1,1'-biphenyl (0.030 g, 0.064 mmol), potassium phosphate, anhydrous (0.132 mL, 1.589 mmol), and Pd$_2$(dba)$_3$ (0.029 g, 0.032 mmol) was purged with N$_2$ followed by the addition of degassed dioxane (2 mL) and degassed water (1.0 mL). The resulting mixture was heated in microwave at 140° C. for 12 min. The reaction went to completion and it was filtered, concentrated, and chromatographed on silica gel using 0-5% MeOH/DCM to afford a light yellow oil. To this product was added TFA (15 mL, 195 mmol) and heated at 70° C. for 18 h until the starting material was consumed. The mixture was concentrated and chromatographed on silica gel using 0-5% 2M NH$_3$ in MeOH/DCM to afford a light yellow solid as (2-(2-amino-3-(2-ethylmorpholino)quinolin-6-yl)-3-methylphenyl)(pyrrolidin-1-yl)methanone. MS (ESI, pos. ion) m/z: 445 (M+1).

Example 22

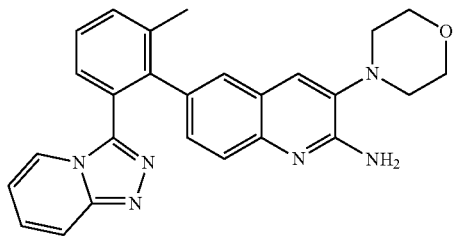 [SMILES: Cc1cccc(-c2nnc3ccccn23)c1-c1ccc2nc(N)c(N3CCOCC3)cc2c1]

Synthesis of 6-(2-([1,2,4]triazolo[4,3-a]pyridine-3-yl)-6-methylphenyl)-3-morpholinoquinolin-2-amine Step 1:
A solution of 2-hydrazinopyridine, 97% (0.254 g, 2.325 mmol), 2-bromo-3-methylbenzoic acid (0.50 g, 2.325 mmol), benzotriazol-1-yl-oxytripyrrolidinophosphonium hexafluorophosphate (PyBOP, 1.452 g, 2.79 mmol), and DIEA (0.812 mL, 4.65 mmol) in DCM (6 mL) was stirred at RT until starting material was completely consumed (~3 h). The mixture was concentrated and chromatographed on silica gel using 0-5% MeOH/DCM to afford a light yellow foam which was dissolved in CH$_3$CN followed by the addition of Lawesson's reagent (0.470 g, 1.163 mmol) and heated at 80° C. for 17 h. The mixture was concentrated and chromatographed on silica gel using 25% EtOAc/hexanes and 0-5% MeOH/DCM to afford a yellow oil as 3-(2-bromo-3-methylphenyl)-[1,2,4]triazolo[4,3-a]pyridine.

Step 2:
A mixture of 3-(2-bromo-3-methylphenyl)-[1,2,4]triazolo[4,3-a]pyridine (0.32 g, 1.111 mmol), 3-morpholino-6-(4,4,5,5-tetramethyl-1,3,2-dioxaborolan-2-yl)quinolin-2-amine (0.17 g, 0.479 mmol, prepared as in Example 2, Step 1-2), 2-(dicyclohexylphosphino)-2',4',6',-tri-1-propyl-1,1'-biphenyl (0.046 g, 0.096 mmol), potassium phosphate, anhydrous (0.198 mL, 2.393 mmol), and Pd$_2$(dba)$_3$ (0.044 g, 0.048 mmol) was purged with N$_2$ followed by the addition of degassed dioxane (2 mL) and water (1.0 mL). The resulting mixture was heated in microwave at 140° C. for 12 min. The reaction was filtered, concentrated, and the resulting crude material was chromatographed on silica gel using gradient 2:1 hexanes/EtOAc and 0-5% 2M NH$_3$ in MeOH/DCM to afford a light yellow solid. It was repurified by HPLC to afford 6-(2-([1,2,4]triazolo[4,3-a]pyridin-3-yl)-6-methylphenyl)-3-morpholinoquinolin-2-amine as a white solid. MS (ESI, pos. ion) m/z: 437 (M+1).

Example 23

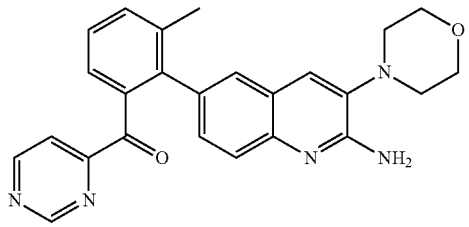 [SMILES: Cc1cccc(C(=O)c2ccncn2)c1-c1ccc2nc(N)c(N3CCOCC3)cc2c1]

Synthesis of (2-(2-amino-3-morpholinoquinolin-6-yl)-3-methylphenyl)(pyrimidin-4-yl)methanone Step 1:
To a mixture of 4-chloro-2-(methylthio)pyrimidine (0.36 mL, 3.11 mmol), 2-bromo-3-methylbenzaldehyde (0.744 g, 3.74 mmol), and 1,3-dimethyl-1H-imidazol-3-ium iodide (0.697 g, 3.11 mmol) in THF (3 mL) was added NaH (0.149 g, 3.74 mmol) and the resulting mixture was refluxed for 30 min. Product was observed and the reaction went to completion. The mixture was brought to RT and poured into ice-water, extracted with DCM and purified using hexanes to afford a light yellow solid as (2-bromo-3-methylphenyl)(2-(methylthio)pyrimidin-4-yl)methanone.

Step 2:
To a solution of (2-bromo-3-methylphenyl)(2-(methylthio)pyrimidin-4-yl)methanone (0.10 g, 0.309 mmol) in EtOH (10 mL) was added Raney 2800 nickel, slurry, in water (0.022 mL, 3.41 mmol) and the resulting mixture was reflux until starting material was consumed (2 h). The mixture was brought to RT and decanted. The remaining Ni was extracted with DCM/NH$_3$ (2M in MeOH). The combined organic layers were concentrated and the residue obtained was extracted with DCM and the extracts were combined and concentrated to afford a yellow oil as (2-bromo-3-methylphenyl)(pyrimidin-4-yl)methanol which was used without purification.

Step 3:
To a solution of (2-bromo-3-methylphenyl)(pyrimidin-4-yl)methanol (0.40 g, 1.433 mmol) in DCM (10 mL) were added sodium bicarbonate (0.223 mL, 5.73 mmol) and Dess-Martin periodinane (0.790 g, 1.863 mmol) in one portion. The resulting mixture was stirred at RT for 1 h then quenched with sat NaHCO$_3$ and sodium thio sulfate pentahydrate (1.778 g, 7.17 mmol). The quenched mixture was stirred for 1 h more and extracted with DCM. The combined organics were washed with brine, dried over Na$_2$SO$_4$, filtered and concentrated to afford (2-bromo-3-methylphenyl) (pyrimidin-4-yl) methanone which was used without purification.

Step 4:

A mixture of (2-bromo-3-methylphenyl)(pyrimidin-4-yl)methanone (0.10 g, 0.361 mmol), 3-morpholino-6-(4,4,5,5-tetramethyl-1,3,2-dioxaborolan-2-yl)quinolin-2-amine (0.192 g, 0.541 mmol, prepared as in Example 2, Step 1-2), potassium phosphate tribasic (0.149 mL, 1.804 mmol), $Pd_2dba_3$ (0.033 g, 0.036 mmol), and 2-(dicyclohexylphosphino)-2',4',6',-tri-1-propyl-1,1'-biphenyl (0.034 g, 0.072 mmol) in dioxane/water (3/1.5 mL) was heated in mw for 12 min at 140° C. The mixture was concentrated and the resulting crude material was chromatographed on silica gel using 0-5% 2M $NH_3$ in MeOH/DCM to afford a brown oil which was further purified by HPLC to afford (2-(2-amino-3-morpholinoquinolin-6-yl)-3-methylphenyl)(pyrimidin-4-yl)methanone as a yellow solid. MS (ESI, pos. ion) m/z: 426 (M+1).

Example 24

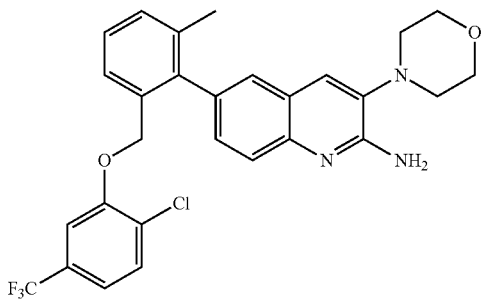 [SMILES: Cc1cccc(COc2cc(C(F)(F)F)ccc2Cl)c1-c1ccc2nc(N)c(N3CCOCC3)cc2c1]

Synthesis of 6-(2-((2-chloro-5-(trifluoromethyl)phenoxy)methyl)-6-methylphenyl)-3-morpholinoquinolin-2-amine Step 1:
A solution of 2-bromo-3-methylbenzoic acid (4.0 g, 18.60 mmol) in THF (93 mL) was cooled to 0° C. and LAH (1.41 g, 37.2 mmol) added by portion. After the reaction completed, aq. K/Na tartrate was added and the reaction stirred overnight. The aqueous layer was extracted with EtOAc and the organic layer was then washed with water and brine (3× ea.), dried over $Na_2SO_4$ and concentrated in vacuo to give (2-bromo-3-methylphenyl)methanol as a clear oil that was used without further purification.

Step 2:
To a solution of (2-bromo-3-methylphenyl)methanol (0.5 g, 2.49 mmol), triphenylphosphine (1.31 g, 4.97 mmol) and 2-chloro-5-(trifluoromethyl)phenol (0.37 mL, 2.74 mmol) in DCM (12.4 mL) at 0° C. was added diethyl azodicarboxylate (1.97 mL, 4.97 mmol) and the reaction warmed to RT for 30 min. The reaction was quenched with water and the aqueous layer was extracted with EtOAc. The organic layer was then washed with water and brine (3× ea.), dried over $Na_2SO_4$ and concentrated in vacuo. The crude material was purified by column chromatography (0-50% Hexene/EtOAc) to afford 2-bromo-1-((2-chloro-5-(trifluoromethyl)phenoxy)methyl)-3-methylbenzene as a clear oil.

Step 3:
A degassed solution of 2-bromo-1-((2-chloro-5-(trifluoromethyl)phenoxy)methyl)-3-methylbenzene (64.1 mg, 0.169 mmol), 3-morpholino-6-(4,4,5,5-tetramethyl-1,3,2-dioxaborolan-2-yl)quinolin-2-amine (50 mg, 0.141 mmol, prepared as in Example 2, Step 1-2), dicyclohexyl(2',4',6'-triisopropylbiphenyl-2-yl)phosphine (13.42 mg, 0.028 mmol), potassium phosphate (149 mg, 0.704 mmol) and $Pd_2(dba)_3$ (6.44 mg, 7.04 μmol) in dioxane (0.94 mL)/water (0.47 mL) was heated in a sealed tube in the microwave at 140° C. for 15 min. The reaction was then quenched with water and the aqueous layer was extracted with EtOAc. The organic layer was then washed with water and brine (3× ea.), dried over $Na_2SO_4$ and concentrated in vacuo to remove the solvent. The crude material was purified by column chromatography with 0-100% (10% $NH_3$ in MeOH/DCM)/DCM to afford 6-(2-((2-chloro-5-(trifluoromethyl)phenoxy)methyl)-6-methylphenyl)-3-morpholinoquinolin-2-amine. MS (ESI, pos. ion) m/z: 528 (M+1).

Example 25

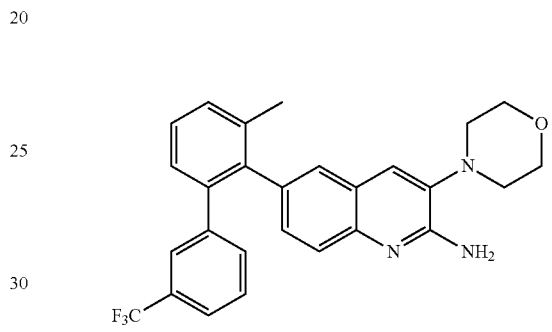

Synthesis of 6-(3-methyl-3'-(trifluoromethyl)biphenyl-2-yl)-3-morpholinoquinolin-2-amine Step 1:
A solution of 2-bromo-1-iodo-3-methylbenzene (200 mg, 0.67 mmol), 4,4,5,5-tetramethyl-2-(3-(trifluoromethyl)phenyl)-1,3,2-dioxaborolane (220 mg, 0.81 mmol), sodium carbonate (214 mg, 2.02 mmol) and tetrakis(triphenylphosphine)palladium (38.9 mg, 0.034 mmol) in toluene (2.0 mL)/EtOH (1.2 mL)/Water (0.2 mL) was heated in an oil bath at 80° C. overnight. The reaction was concentrated and the resultant residue purified by column chromatography (100% Hexanes) to yield 2-bromo-3-methyl-3'-(trifluoromethyl)biphenyl.

Step 2:
A solution of 3-morpholino-6-(4,4,5,5-tetramethyl-1,3,2-dioxaborolan-2-yl)quinolin-2-amine (50 mg, 0.141 mmol, prepared as in Example 2, Step 1-2), 2-bromo-3-methyl-3'-(trifluoromethyl)biphenyl (66.5 mg, 0.211 mmol), dicyclohexyl(2',4',6'-triisopropylbiphenyl-2-yl)phosphine (13.42 mg, 0.028 mmol), potassium phosphate (90 mg, 0.422 mmol) and $PdCl_2(dppf)$-$CH_2Cl_2$ adduct (5.15 mg, 7.04 mmol) in ethanol (1206 μL)/water (201 μL) was heated in a sealed tube in the microwave at 140° C. for 20 min. The reaction was then quenched with water and the aqueous layer was extracted with EtOAc. The organic layer was then washed with water and brine (3× ea.), dried over $Na_2SO_4$ and concentrated in vacuo to remove the solvent. The crude material was purified by column chromatography with 0-70% (10% MeOH/DCM)/

DCM to afford 6-(3-methyl-3'-(trifluoromethyl)biphenyl-2-yl)-3-morpholinoquinolin-2-amine MS (ESI, pos. ion) m/z: 464 (M+1).

Example 26

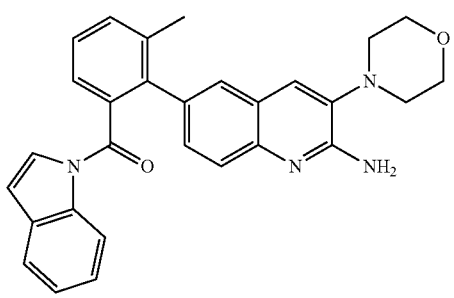 [SMILES: Cc1cccc(C(=O)n2ccc3ccccc32)c1-c1ccc2nc(N)c(N3CCOCC3)cc2c1]

Synthesis of (2-(2-amino-3-morpholinoquinolin-6-yl)-3-methylphenyl)(1H-indol-1-yl)methanone Step 1:

To a solution of 2-bromo-3-methylbenzoic acid (1.0 g, 4.65 mmol) and 1H-indole (0.60 g, 5.12 mmol) in DCM (23.3 mL) at RT was added DCC (1.15 g, 5.58 mmol) and 4-dimethylaminopyridine (0.11 g, 0.93 mmol). The reaction was stirred at RT overnight. The reaction was quenched with water and the aqueous layer was extracted with EtOAc. The organic layer was then washed with water and brine (3× ea.), dried over $Na_2SO_4$ and concentrated in vacuo. The crude material was purified by column chromatography (0-50% Hexene/EtOAC) to yield (2-bromo-3-methylphenyl)(1H-indol-1-yl) methanone as a clear oil.

Step 2:

The product from step 1 was carried on in a manner analogous to the procedure described in Example 24, Step 3, but using (2-bromo-3-methylphenyl)(1H-indol-1-yl)methanone, to give (2-(2-amino-3-morpholinoquinolin-6-yl)-3-methylphenyl)(1H-indol-1-yl)methanone. MS (ESI, pos. ion) m/z: 463 (M+1).

Example 27

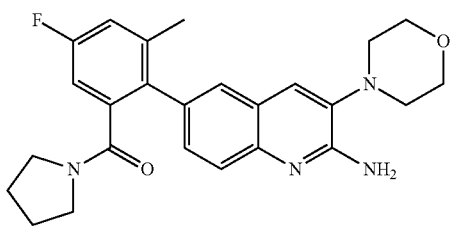 [SMILES: Cc1cc(F)cc(C(=O)N2CCCC2)c1-c1ccc2nc(N)c(N3CCOCC3)cc2c1]

Synthesis of (2-(2-amino-3-morpholinoquinolin-6-yl)-5-fluoro-3-methylphenyl)(pyrrolidin-1-yl)methanone Step 1:

To a solution of 4-fluoro-2-methylaniline (5.0 g, 40.0 mmol) in DCM (100 mL) at RT was added bromine (2.06 mL, 40.0 mmol). The reagent appeared to react instantly and a solid precipitate was formed. The reaction was filtered and washed with DCM to give 2-bromo-4-fluoro-6-methylaniline hydrobromide as a light tan solid.

Step 2:

A solution of 2-bromo-4-fluoro-6-methylaniline HCl (5.0 g, 17.6 mmol) in 25% aq. HBr (38.1 mL, 175 mmol) was cooled to 0° C. and an aq. solution of sodium nitrite (0.59 mL, 18.4 mmol) added, followed by a small amount of EtOH to aid solubility. The reaction was stirred at this temperature for 25 min before transferring by pipette to a solution of copper(I) bromide (2.64 g, 18.4 mmol) in 25% aq. HBr (20 ml) at 70° C. The reaction was stirred at this temperature for 3 h. The reaction was quenched with $NaHCO_3$ and the aqueous layer was extracted with EtOAc. The organic layer was then washed with water and brine (3× ea.), dried over $Na_2SO_4$ and concentrated in vacuo. The crude material was purified by column chromatography (0-10% Hexene/EtOAC) to yield 1,2-dibromo-5-fluoro-3-methylbenzene as a clear oil.

Step 3:

A solution of 1,2-dibromo-5-fluoro-3-methylbenzene (1.0 g, 3.73 mmol) in THF (37.3 mL) was cooled to −40° C. and isopropylmagnesium chloride (2.05 mL, 4.11 mmol) added. The reaction was stirred at this temp for 2 h before addition of small pellets of dry ice were added and the reaction was warmed to RT. The reaction was quenched with 1N NaOH and EtOAc was added. The aqeuous layer was then separated, acidified with 3N HCl and extracted with EtOAc. The organic layer was then washed with water and brine (3× ea.), dried over $Na_2SO_4$ and concentrated in vacuo. No evidence of more than one regioisomer was observed and 2-bromo-5-fluoro-3-methylbenzoic acid was used without further purification.

Step 4:

To a solution of 2-bromo-5-fluoro-3-methylbenzoic acid (140 mg, 0.60 mmol), pyrrolidine (99 μL, 1.20 mmol) and Hunig's base (210 μL, 1.20 mmol) in DMF (2 mL) at RT was added HATU (457 mg, 1.20 mmol) and the reaction stirred at this temp overnight. The reaction was quenched with water and the aqueous layer was extracted with EtOAc. The organic layer was then washed with water and brine (3× ea.), dried over $Na_2SO_4$ and concentrated in vacuo. The crude material was purified by column chromatography (0-60% Hex/EtOAC) to yield (2-bromo-5-fluoro-3-methylphenyl)(pyrrolidin-1-yl)methanone as a clear oil.

Step 5:

The product from step 4 was carried by a procedure analogous to that described in Example 24, Step 3, to give (2-(2-amino-3-morpholinoquinolin-6-yl)-5-fluoro-3-methylphenyl)(pyrrolidin-1-yl)methanone. MS (ESI, pos. ion) m/z: 435 (M+1).

Example 28

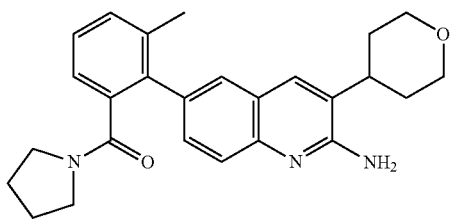 [SMILES: Cc1cccc(C(=O)N2CCCC2)c1-c1ccc2nc(N)c(C3CCOCC3)cc2c1]

Synthesis of (2-(2-amino-3-(tetrahydro-2H-pyran-4-yl)quinolin-6-yl)-3-methylphenyl)(pyrrolidin-1-yl)methanone Step 1:

A glass microwave reaction vessel was charged with 6-bromo-2-chloro-3-iodoquinoline (0.918 g, 2.492 mmol) and 4-methoxybenzylamine (2.279 mL, 17.44 mmol) in N-methyl-2-pyrrolidinone (3.56 mL). The reaction mixture was stirred and heated in a microwave reactor at 130° C. for 20 min. The solution was poured into water and extracted with diethyl ether. The combined organic extracts were washed with saturated ammonium chloride, water, saturated sodium chloride, and dried over magnesium sulfate. The solution was filtered and concentrated in vacuo to give the crude material 6-bromo-3-iodo-N-(4-methoxybenzyl)quinolin-2-amine as a tan solid which was used without further purification.

Step 2:

Isopropylmagnesium chloride, 2M THF (1.322 mL, 2.64 mmol) was added to a solution of 6-bromo-3-iodo-N-(4-methoxybenzyl)quinolin-2-amine (1.24 g, 2.64 mmol) in THF (25 mL) cooled to −20° C. After stirring for 5 min, an additional amount of iso-propylmagnesium chloride, 2M THF (1.322 mL, 2.64 mmol) was added and the solution was stirred 10 min at this temperature. Next, dihydro-2H-pyran-4(3H)-one (0.293 mL, 3.17 mmol) was added and the reaction was allowed to come to 0° C. After 20 min, the reaction mixture was diluted with saturated ammonium chloride and extracted with EtOAc. The combined organic extracts were washed with saturated ammonium chloride, water, saturated sodium chloride, and dried over sodium sulfate. The solution was filtered and concentrated in vacuo to give the crude material which was purified by silica gel chromatography by eluting with 1:3 to 1:1 EtOAc in hexane, to provide 4-(6-bromo-2-(4-methoxybenzylamino)quinolin-3-yl)tetrahydro-2H-pyran-4-ol as light-yellow oil.

Step 3:

4-(6-Bromo-2-(4-methoxybenzylamino)quinolin-3-yl)tetrahydro-2H-pyran-4-ol (0.250 g, 0.564 mmol) in a mixture of dioxane (4 mL), 5N HCl (4.00 mL, 20.00 mmol) and concentrated HCl (1.00 mL, 32.9 mmol) was heated at 90° C. for 5 h. The reaction was transferred to a microwave reaction vessel and heated in a microwave reactor at 130° C. for 40 min and was concentrated. The crude solid was partitioned between EtOAc and 10% sodium carbonate. The combined organic extracts were washed with water, saturated sodium chloride, and dried over sodium sulfate. The solution was filtered and concentrated in vacuo to give the crude material. The crude material was purified by silica gel chromatography by eluting with 1:30 2M $NH_3$ in MeOH/DCM to provide 6-bromo-3-(3,6-dihydro-2H-pyran-4-yl)quinolin-2-amine as white solid.

Step 4:

[1,1-bis(diphenylphosphino)ferrocene]dichloropalladium (0.013 g, 0.016 mmol) was added to a flask with 4,4,4',4',5,5,5',5'-octamethyl-2,2'-bi(1,3,2-dioxaborolane) (0.10 g, 0.393 mmol), potassium acetate (0.096 g, 0.983 mmol) and 6-bromo-3-(3,6-dihydro-2H-pyran-4-yl)quinolin-2-amine (0.100 g, 0.328 mmol). The flask was evacuated and flushed with $N_2$ gas 3× before dioxane (2 mL) (degassed by bubbling $N_2$ gas through the solution for 10 min) was added. The reaction was heated to 85° C. for 16 h. The reaction was concentrated and then taken up in EtOAc and filtered. The filtrate was concentrated to afford the crude product of 3-(3,6-dihydro-2H-pyran-4-yl)-6-(4,4,5,5-tetramethyl-1,3,2-dioxaborolan-2-yl)quinolin-2-amine which was used without purification.

Step 5:

A glass microwave reaction vessel was charged with 3-(3,6-dihydro-2H-pyran-4-yl)-6-(4,4,5,5-tetramethyl-1,3,2-dioxaborolan-2-yl)quinolin-2-amine (0.058 g, 0.165 mmol), potassium acetate (0.032 g, 0.329 mmol), bis(di-tert-butyl(4-dimethylaminophenyl)phosphine)dichloropalladium(II) (5.83 mg, 8.23 μmol), and (2-iodo-3-methylphenyl)(pyrrolidin-1-yl)methanone (0.078 g, 0.247 mmol). The vessel was evacuated and flushed with $N_2$ gas 3× before EtOH1 (1.6 mL) and water (0.23 mL) (each degassed by bubbling $N_2$ gas through the solution for 10 min prior to addition) was added. The reaction mixture was stirred and heated in a microwave reactor at 130° C. for 10 min. 2-(Dicyclohexylphosphino)-2',4',6',-tri-1-propyl-1,1'-biphenyl (0.012 g, 0.026 mmol), potassium phosphate tribasic (0.041 mL, 0.494 mmol), $Pd_2(dba)_3$ (7.54 mg, 8.23 μmol) were added and the reaction was degassed and heated in the Initiator microwave reactor again for 20 min at 130° C. The reaction mixture was diluted with 10:1 saturated ammonium chloride/ammonium hydroxide and extracted with EtOAc. The combined organic extracts were washed with 10:1 saturated ammonium chloride/ammonium hydroxide, water, saturated sodium chloride, and dried over sodium sulfate. The solution was filtered and concentrated in vacuo to give the crude material which was purified by silica gel chromatography by eluting with 1:20 2M $NH_3$ in MeOH/DCM, to provide (2-(2-amino-3-(3,6-dihydro-2H-pyran-4-yl)quinolin-6-yl)-3-methylphenyl)(pyrrolidin-1-yl)methanone.

Step 6:

Pd/C (10%) (0.051 g, 0.048 mmol) was added to a degassed ($N_2$) solution of (2-(2-amino-3-(3,6-dihydro-2H-pyran-4-yl)quinolin-6-yl)-3-methylphenyl)(pyrrolidin-1-yl)methanone (0.020 g, 0.048 mmol) in EtOH (1.00 mL). The solution was degassed with $H_2$ gas and then stirred under a balloon of $H_2$ gas for 12 h. The reaction was degassed with $N_2$ and then filtered through a pad of celite with EtOAc and concentrated. The crude material was purified by silica gel chromatography by eluting with 20:1 2M $NH_3$ in MeOH/DCM to provide (2-(2-amino-3-(tetrahydro-2H-pyran-4-yl)quinolin-6-yl)-3-methylphenyl)(pyrrolidin-1-yl)methanone. MS (ESI, pos. ion) m/z: 416 (M+1).

Example 29

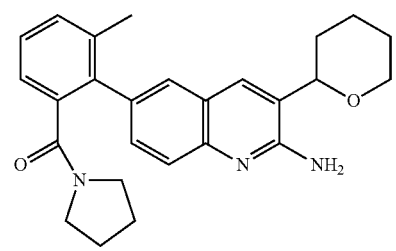 [SMILES: Cc1cccc(C(=O)N2CCCC2)c1-c1ccc2nc(N)c(C3CCCCO3)cc2c1]

Synthesis of ((2-(2-amino-3-(tetrahydro-2H-pyran-2-yl)quinolin-6-yl)-3-methylphenyl)(pyrrolidin-1-yl)methanone Step 1:

6-Bomo-2-chloroquinoline-3-carbaldehyde (10 g, 37.0 mmol) was dissolved in NMP 200 mL in a 350 mL sealable flask. 2-Methylpropan-2-amine (23 mL, 217 mmol) was added and the reaction mixture was sealed to heated at 130° C. for 24 h. After cooling, the mixture was poured into 1N HCl 200 mL and stirred for 1.5 h. The reaction was completed. The precipitate was isolated by filtration and washed with water. The solid was collected and dried on vacuum pump overnight to give 6-bromo-2-(tert-butylamino)quinoline-3-carbaldehyde as a yellow solid.

Step 2:

[1,1-Bis(diphenylphosphino)ferrocene]dichloropalladium (0.33 g, 0.407 mmol) was added to a flask with 6-bromo-2-(tert-butylamino)quinoline-3-carbaldehyde (2.50 g, 8.14 mmol), potassium acetate (2.40 g, 24.42 mmol) and bis(pinacolato)diboron (2.48 g, 9.77 mmol). The flask was evacuated and flushed with $N_2$ gas 3× before dioxane (49.3 mL) (degassed by bubbling $N_2$ gas through the solution for 10 min) was added. The reaction was heated to 85° C. for 12 h. The reaction was concentrated and then taken up in EtOAc and filtered. The filtrate was concentrated to afford the crude product 2-(tert-butylamino)-6-(4,4,5,5-tetramethyl-1,3,2-dioxaborolan-2-yl)quinoline-3-carbaldehyde used without further purification.

Step 3:

A 20 mL glass microwave reaction vessel was charged with 2-(tert-butylamino)-6-(2-methyl-6-(pyrrolidine-1-carbonyl)phenyl)quinoline-3-carbaldehyde, potassium phosphate (1.20 g, 5.65 mmol), dicyclohexyl(2',4',6'-triisopropylbiphenyl-2-yl)phosphine (0.135 g, 0.282 mmol), $Pd_2(dba)_3$ (0.065 g, 0.071 mmol), and (2-iodo-3-methylphenyl)(pyrrolidin-1-yl)methanone (0.578 g, 1.835 mmol). The vessel was evacuated and flushed with $N_2$ 3× before dioxane (9.41 mL) and water (4.70 mL) (each degassed by bubbling $N_2$ gas through the solution for 10 min prior to addition) were added. The reaction mixture was stirred and heated in a microwave reactor at 140° C. for 15 min. The reaction mixture was diluted with water and extracted with EtOAc. The combined organic extracts were washed with 10:1 saturated ammonium chloride/ammonium hydroxide, water, saturated sodium chloride, and dried over sodium sulfate. The solution was filtered and concentrated in vacuo to give the crude material which was purified by silica gel chromatography by eluting with 1:2 to 2:1 EtOAc in hexane (DCM load) to provide 2-(tert-butylamino)-6-(2-methyl-6-(pyrrolidine-1-carbonyl)phenyl)quinoline-3-carbaldehyde.

Step 4:

n-Butyllithium (2.5 M) (0.624 mL, 1.559 mmol) was added to a solution of 2-(3-butynyloxy)tetrahydro-2H-pyran (0.244 mL, 1.559 mmol) in THF (10 mL) at −78° C. The solution was stirred 1 h at this temperature before warming to 0° C. for 30 min at which time it was slowly added by syringe to a solution of 2-(tert-butylamino)-6-(2-methyl-6-(pyrrolidine-1-carbonyl)phenyl)quinoline-3-carbaldehyde (0.324 g, 0.780 mmol) in THF (10 mL) cooled to −78° C. The resulting dark solution was stirred 10 min at this temperature before warming to 0° C. for 20 min. The reaction mixture was diluted with saturated ammonium chloride and extracted with EtOAc. The combined organic extracts were washed with water, saturated sodium chloride, and dried over sodium sulfate. The solution was filtered and concentrated in vacuo to give (2-(2-(tert-butylamino)-3-(1-hydroxy-5-(tetrahydro-2H-pyran-2-yloxy)pent-2-ynyl)quinolin-6-yl)-3-methylphenyl)(pyrrolidin-1-yl)methanone as an orange oil.

Step 5:

10% Pd/C (0.332 g, 0.312 mmol) was added to a solution of (2-(2-(tert-butylamino)-3-(1-hydroxy-5-(tetrahydro-2H-pyran-2-yloxy)pent-2-ynyl)quinolin-6-yl)-3-methylphenyl)(pyrrolidin-1-yl)methanone (0.444 g, 0.779 mmol) in MeOH (8 mL) which had been degassed with $N_2$. The flask was purged with $H_2$ gas and stirred under a balloon of $H_2$ gas while being carefully monitored until all the stating material had been consumed. The reaction was degassed with $N_2$ and poured through a pad of celite with methanol. The filtrate was reduced in volume to about 10 mL and 4-methylbenzenesulfonic acid hydrate (0.178 g, 0.935 mmol) was added and the solution was stirred at RT until complete removal of the THP group was observed. Solid sodium bicarbonate was added and the mixture was concentrated and portioned between water and EtOAc. The combined organic extracts were washed with water, saturated sodium chloride, and dried over sodium sulfate. The solution was filtered and concentrated in vacuo to give the crude material which was purified by filtering through a plug of silica and eluting with EtOAc and then 1:10 2M $NH_3$ in MeOH/dichloromethane to elute the product (2-(2-(tert-butylamino)-3-(1,5-dihydroxypentyl)quinolin-6-yl)-3-methylphenyl)(pyrrolidin-1-yl)methanone.

Step 6:

TsOH (0.109 g, 0.572 mmol) was added to a solution of (2-(2-(tert-butylamino)-3-(1,5-dihydroxypentyl)quinolin-6-yl)-3-methylphenyl)(pyrrolidin-1-yl)methanone (0.070 g, 0.143 mmol) in toluene (2.0 mL) and the reaction was refluxed for 1.5 h. The reaction was concentrated and diluted with 10% sodium carbonate and extracted with dichloromethane. The combined organic extracts were washed with saturated sodium chloride, and dried over sodium sulfate. The solution was filtered and concentrated in vacuo to give the crude material which was purified by silica gel chromatography by eluting with 100% EtOAc followed by 1:20 2M $NH_3$ in MeOH/dichloromethane, to provide (2-(2-amino-3-(tetrahydro-2H-pyran-2-yl)quinolin-6-yl)-3-methylphenyl)(pyrrolidin-1-yl)methanone. MS (ESI, pos. ion) m/z: 416 (M+1).

Example 30

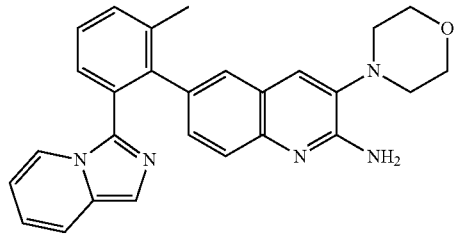 [SMILES: Cc1cccc(-c2ncc3ccccn23)c1-c1ccc2nc(N)c(N3CCOCC3)cc2c1]

Synthesis of 6-(2-(imidazo[1,5-a]pyridin-3-yl)-6-methylphenyl)-3-morpholinoquinolin-2-amine Step 1:

DMF (0.030 mL, 0.382 mmol) was added to a solution of 2-iodo-3-methylbenzoic acid (1.0 g, 3.82 mmol) and $SOCl_2$ (0.279 mL, 3.82 mmol) in DCM (20 mL) at 0° C. After stirring 1 h at RT the solution was cooled to 0° C. DIPEA (2.0 mL, 11.45 mmol) followed by 2-(aminomethyl)pyridine (0.390 mL, 3.82 mmol) were added by slow addition and the solution was stirred at 0° C. After 1 h, the reaction was diluted with saturated ammonium chloride and the organics were removed. The reaction mixture was diluted with water and extracted with EtOAc. The combined organic extracts were washed with saturated ammonium chloride, water, saturated sodium bicarbonate, and dried over sodium sulfate. The solution was filtered and concentrated in vacuo to give the crude material which was dissolved in toluene (20 mL). Lawesson's reagent (0.772 g, 1.908 mmol) was added and the reaction was refluxed for 12 h and then concentrated. The crude product was taken up in minimal DCM, and the product was precipitate out with diethyl ether to afford 2-iodo-3-methyl-N-(pyridin-2-ylmethyl)benzothioamide as a solid.

Step 2:

Iodine (0.827 g, 3.26 mmol) and pyridine (0.263 mL, 3.26 mmol) were added to 2-iodo-3-methyl-N-(pyridin-2-ylmethyl)benzothioamide (0.40 g, 1.086 mmol) in THF (2.2 mL) at 0° C. The solution was allowed to warm to RT and stirred 15 min. The reaction mixture was diluted with saturated sodium bicarbonate and aq. sodium sulfite and extracted with EtOAc. The combined organic extracts were washed with saturated sodium bicarbonate, water, saturated sodium chloride, and dried over sodium sulfate. The solution was filtered and concentrated in vacuo to give the crude material. The crude material was purified by silica gel chromatography by eluting with 1:1.5 EtOAc in hexane to provide 3-(2-iodo-3-methylphenyl)imidazo[1,5-a]pyridine.

Step 3:

A glass microwave reaction vessel was charged with 3-morpholino-6-(4,4,5,5-tetramethyl-1,3,2-dioxaborolan-2-yl)quinolin-2-amine (0.236 g, 0.664 mmol, prepared as in Example 2, Step 1-2), potassium phosphate (0.564 g, 2.66 mmol), dicyclohexyl(2',4',6'-triisopropylbiphenyl-2-yl)phosphine (0.063 g, 0.133 mmol), Pd$_2$(dba)$_3$ (0.030 g, 0.033 mmol), and 3-(2-iodo-3-methylphenyl)imidazo[1,5-a]pyridine (0.222 g, 0.664 mmol). The vessel was evacuated and flushed with nitrogen three times before dioxane (4.43 mL) and water (2.215 mL) (each degassed by bubbling nitrogen gas through the solution for 10 min prior to addition) were added. The reaction mixture was stirred and heated in a microwave reactor at 140° C. for 15 min. The reaction mixture was diluted with 10:1 saturated ammonium chloride/ammonium hydroxide and extracted with EtOAc. The combined organic extracts were washed with 10:1 saturated ammonium chloride/ammonium hydroxide, water, saturated sodium chloride, and dried over sodium sulfate. The solution was filtered and concentrated in vacuo to give the crude material. The crude material was purified by silica gel chromatography by eluting with 1:20 2M NH$_3$ in MeOH/DCM. The fractions containing the product (with some impurities) were combined and concentrated. The solid was dissolved in MeOH and filtered to remove some of the impurity. The remainder of the sample was purified by reverse-phase preparative HPLC with 0.1% TFA in CH$_3$CN/H$_2$O, gradient 5-70% over 20 min to provide 6-(2-(imidazo[1,5-a]pyridin-3-yl)-6-methylphenyl)-3-morpholinoquinolin-2-amine. The purified compound was partitioned between DCM and saturated sodium bicarbonate. The layers were separated and the aqueous layer was extracted with DCM. The combined organic extracts were washed with saturated sodium chloride and dried over sodium sulfate. The solution was filtered and concentrated in vacuo to give 6-(2-(imidazo[1,5-a]pyridin-3-yl)-6-methylphenyl)-3-morpholinoquinolin-2-amine as a white solid. MS (ESI, pos. ion) m/z: 436 (M+1).

Example 31

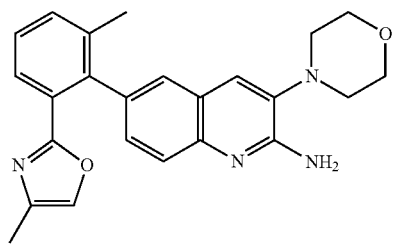 [SMILES: Cc1coc(-c2cccc(C)c2-c2ccc3nc(N)c(N4CCOCC4)cc3c2)n1]

Synthesis of 6-(2-methyl-6-(4-methyloxazol-2-yl)phenyl)-3-morpholinoquinolin-2-amine Step 1:

Thionyl chloride (0.570 mL, 7.81 mmol) was added to a solution of 2-bromo-3-methylbenzoic acid (1.60 g, 7.44 mmol) and DMF (0.058 mL, 0.744 mmol) in DCM (50 mL) at 0° C. The reaction mixture was allowed to warm to RT and stirred for 1 hr and then cooled to 0° C. before ammonia 2N i-PrOH (18.60 mL, 37.2 mmol) was added. The resulting cloudy solution was stirred for 30 min. The reaction mixture was diluted with water and extracted with EtOAc. The combined organic extracts were washed with 10% sodium carbonate, saturated ammonium chloride, saturated sodium chloride, and dried over sodium sulfate. The solution was filtered and concentrated in vacuo to give the crude material as a white solid. The solid was dissolved in EtOH (30 mL) and divided evenly into 2×20 mL microwave vials. 1-Chloro-2-propanone (0.574 mL, 7.44 mmol) was added into each vial and the reaction mixture was stirred and heated in a microwave reactor at 150° C. for 2 h. The reactions were concentrated and the crude material was purified by silica gel chromatography to provide 2-(2-bromo-3-methylphenyl)-4-methyloxazole.

Step 2:

A glass microwave reaction vessel was charged with 3-morpholino-6-(4,4,5,5-tetramethyl-1,3,2-dioxaborolan-2-yl)quinolin-2-amine (0.055 g, 0.155 mmol, prepared as in Example 2, Step 1-2), potassium phosphate (0.131 g, 0.619 mmol), dicyclohexyl(2',4',6'-triisopropylbiphenyl-2-yl)phosphine (0.015 g, 0.031 mmol), Pd$_2$(dba)$_3$ (7.09 mg, 7.74 µmol), and 2-(2-bromo-3-methylphenyl)-4-methyloxazole (0.078 g, 0.310 mmol). The vessel was evacuated and flushed with nitrogen three times before dioxane (1.0 mL) and water (0.50 mL) (each degassed by bubbling nitrogen gas through the solution for 10 min prior to addition) were added. The reaction mixture was stirred and heated in a microwave at 130° C. for 15 min. The reaction mixture was diluted with 10:1 saturated ammonium chloride/ammonium hydroxide and extracted with EtOAc. The combined organic extracts were washed with 10:1 saturated ammonium chloride/ammonium hydroxide, water, saturated sodium chloride, and dried over sodium sulfate. The solution was filtered and concentrated in vacuo to give the crude material which was purified by silica gel chromatography by eluting with 1:15:15 2M NH$_3$ in MeOH/DCM/diethyl ether to provide the desired product which after triturating with diethyl ether gave 6-(2- methyl-6-(4-methyloxazol-2-yl)phenyl)-3-morpholino-quinolin-2-amine as white solid. MS (ESI, pos. ion) m/z: 401 (M+1).

Example 32

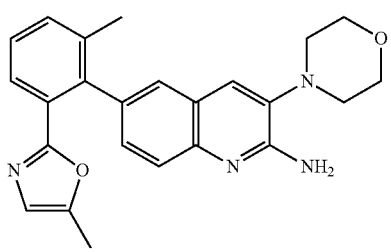 [SMILES: Cc1cnc(-c2cccc(C)c2-c2ccc3nc(N)c(N4CCOCC4)cc3c2)o1]

Synthesis of 6-(2-methyl-6-(5-methyloxazol-2-yl)phenyl)-3-morpholinoquinolin-2-amine Step 1:

Thionyl chloride (0.679 mL, 9.30 mmol) was added to a solution of 2-bromo-3-methylbenzoic acid (2.0 g, 9.30 mmol) and DMF (0.072 mL, 0.930 mmol) in DCM (100 mL) at 0° C. The reaction mixture was allowed to warm to RT and stirred for 1 h and then cooled to 0° C. before DIPEA (3.25 mL, 18.60 mmol) followed by 2-propynylamine (0.766 mL, 11.16 mmol) were added. The resulting solution was stirred for 45 min at 0° C. The reaction mixture was diluted with saturated ammonium chloride and water and then extracted with EtOAc. The combined organic extracts were washed with saturated ammonium chloride, water, saturated sodium bicarbonate, saturated sodium chloride and dried over sodium sulfate. The solution was filtered and concentrated in vacuo to give the crude material as a tan solid. The crude product was dissolved in dioxane (100 mL) and cooled to 0° C. Sodium hydride (0.409 g, 10.23 mmol) was added and the mixture was stirred at RT for 30 min before bringing to a reflux. After 5 h, the reaction is concentrated. The crude material was purified by silica gel chromatography to provide 2-(2-bromo-3-methylphenyl)-5-methyloxazole.

Step 2:

A glass microwave reaction vessel was charged with 3-morpholino-6-(4,4,5,5-tetramethyl-1,3,2-dioxaborolan-2-yl)quinolin-2-amine (0.055 g, 0.155 mmol, prepared as in Example 2, Step 1-2), potassium phosphate (0.131 g, 0.619 mmol), dicyclohexyl(2',4',6'-triisopropylbiphenyl-2-yl)phosphine (0.015 g, 0.031 mmol), Pd$_2$dba$_3$ (0.142 g, 0.155 mmol), and 2-(2-bromo-3-methylphenyl)-5-methyloxazole (0.078 g, 0.310 mmol). The vessel was evacuated and flushed with N$_2$ 3× before dioxane (1.00 mL) and water (0.500 mL) (each degassed by bubbling N$_2$ gas through the solution for 10 min prior to addition) were added. The reaction mixture was stirred and heated in a microwave reactor at 130° C. for 15 min. The reaction mixture was diluted with 10:1 saturated ammonium chloride/ammonium hydroxide and extracted with EtOAc. The combined organic extracts were washed with 10:1 saturated ammonium chloride/ammonium hydroxide, water, saturated sodium chloride, and dried over sodium sulfate. The solution was filtered and concentrated in vacuo to give the crude material. The crude material was purified by silica gel chromatography by eluting with 1:15:15 2M NH$_3$ in MeOH/dichloromethane/sdiethyl ether, to provide the desired product which after triturating with diethyl ether gave 6-(2-methyl-6-(5-methyloxazol-2-yl)phenyl)-3-morpholinoquinolin-2-amine. MS (ESI, pos. ion) m/z: 401 (M+1).

Example 33

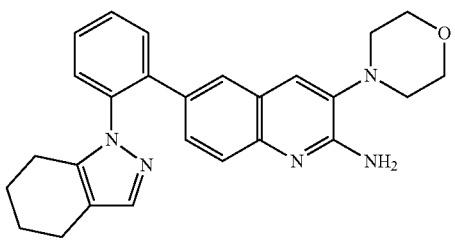 [SMILES: Nc1nc2ccc(-c3ccccc3-n3ncc4c3CCCC4)cc2cc1N1CCOCC1]

Synthesis of 3-morpholino-6-(2-(4,5,6,7-tetrahydro-1H-indazol-1-yl)phenyl)quinolin-2-amine Step 1:

2-Bromophenylhydrazine hydrochloride (1.00 g, 4.47 mmol) was added to a solution of 2-(hydroxymethylene)cyclohexanone (0.564 g, 4.47 mmol) in ethanol (20 mL) and the resulting solution was refluxed 3 h before being concentrated. The crude material was taken up in DCM and washed with saturated ammonium chloride, 1N NaOH, saturated sodium chloride, and dried over sodium sulfate. The solution was filtered and concentrated in vacuo to give 1-(2-bromophenyl)-4,5,6,7-tetrahydro-1H-indazole.

Step 2:

A glass microwave reaction vessel was charged with 3-morpholino-6-(4,4,5,5-tetramethyl-1,3,2-dioxaborolan-2-yl)quinolin-2-amine (0.128 g, 0.361 mmol, prepared as in Example 2, Step 1-2), potassium phosphate (0.306 g, 1.443 mmol), dicyclohexyl(2',4',6'-triisopropylbiphenyl-2-yl)phosphine (0.034 g, 0.072 mmol), Pd$_2$db$_3$ (0.017 g, 0.018 mmol), and 1-(2-bromophenyl)-4,5,6,7-tetrahydro-1H-indazole (0.200 g, 0.722 mmol). The vessel was evacuated and flushed with N$_2$ 3× before dioxane (2.4 mL) and water (1.2 mL) (each degassed by bubbling N$_2$ gas through the solution for 10 min prior to addition) were added. The reaction mixture was stirred and heated in a microwave reactor at 140° C. for 15 min. The reaction mixture was diluted with 10:1 saturated ammonium chloride/ammonium hydroxide and extracted with EtOAc. The combined organic extracts were washed with 10:1 saturated ammonium chloride/ammonium hydroxide, water, saturated sodium chloride, and dried over sodium sulfate. The solution was filtered and concentrated in vacuo to give the crude material. The crude material was purified by silica gel chromatography by eluting through a plug of silica with 1:1 EtOAc/Hexanes then 1:10 2M NH$_3$ in MeOH/DCM. The sample was further purified by reverse-phase preparative HPLC with 0.1% TFA in CH$_3$CN/H$_2$O, gradient 5-20% over 15 min to provide 3-morpholino-6-(2-(4,5,6,7-tetrahydro-1H-indazol-1-yl)phenyl)quinolin-2-amine. The purified compound was partitioned between DCM and saturated sodium bicarbonate. The layers were separated and the aqueous layer was extracted with dichloromethane. The combined organic extracts were washed with saturated sodium chloride and dried over sodium sulfate. The solution was filtered and concentrated in vacuo to give the pure material as a white solid. MS (ESI, pos. ion) m/z: 426 (M+1).

Example 34

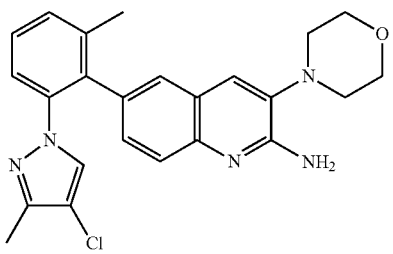 [SMILES: Cc1cccc(-n2cc(Cl)c(C)n2)c1-c1ccc2nc(N)c(N3CCOCC3)cc2c1]

Synthesis of 6-(2-(4-chloro-3-methyl-1H-pyrazol-1-yl)-6-methylphenyl)-3-morpholinoquinolin-2-amine Step 1:
2-Bromo-6-methylaniline (1.080 mL, 8.58 mmol), 4-chloro-3-methyl-1H-pyrazole (1.0 g, 8.58 mmol), potassium carbonate (2.49 g, 18.02 mmol), and copper(I) iodide (0.082 g, 0.429 mmol) were added to a RBF which was evacuated and flushed with $N_2$ 3×. Toluene (9 mL) (degassed by bubbling $N_2$ through solution for 10 minutes) and N1,N2-dimethylethane-1,2-diamine (0.185 mL, 1.716 mmol) were added and the mixture was heated in an oil bath at 110° C. After 18 h, the reaction was allowed to cool, diluted with EtOAc, and 10:1 saturated ammonium chloride/ammonium hydroxide. The layers were separated and the aqueous layer was extracted with EtOAc. The combined organic extracts were washed with water, saturated sodium chloride, and dried over sodium sulfate. The solution was filtered and concentrated in vacuo to give the crude material. The crude material was purified by silica gel column chromatography eluting with 1:2 EtOAc in hexanes to provide 2-(4-chloro-3-methyl-1H-pyrazol-1-yl)-6-methylaniline.

Step 2:
Sulfuric acid (7.77 mL, 146 mmol) was added to a solution of 2-(4-chloro-3-methyl-1H-pyrazol-1-yl)-6-methylaniline (1.9 g, 8.57 mmol) in concentrated hydrogen chloride (2.056 mL, 25.7 mmol) at 0° C. The solution was stirred and after cooling back to 0° C., sodium nitrite (0.591 g, 8.57 mmol) in water (3.5 mL) was added dropwise. The reaction was stirred 40 min at 0° C. before potassium iodide (2.85 g, 17.14 mmol) in water (3.5 mL) was added dropwise and then the solution was stirred at RT. After 1 h, the reaction is poured into ice with EtOAc and separated. The aqueous layer was extracted with EtOAc. The combined organic extracts were washed with 1N HCl, water, saturated sodium bicarbonate, 1N sodium sulfite, and dried over sodium sulfate. The solution was filtered and concentrated in vacuo to give the crude material. The crude material was purified by silica gel column chromatography by eluting with 1:4 EtOAc in hexane to provide 4-chloro-1-(2-iodo-3-methylphenyl)-3-methyl-1H-pyrazole.

Step 3:
A glass microwave reaction vessel was charged with 3-morpholino-6-(4,4,5,5-tetramethyl-1,3,2-dioxaborolan-2-yl)quinolin-2-amine (0.150 g, 0.422 mmol, prepared as in Example 2, Step 1-2) and 4-chloro-1-(2-iodo-3-methylphenyl)-3-methyl-1H-pyrazole (0.281 g, 0.845 mmol) in dioxane (3 mL) and 2 M aqueous sodium carbonate (1.0 mL, 2.0 mmol). The vessel was capped with a septum and the solution was degassed by bubbling nitrogen gas through the solution for 10 min. Next, Pd $(PPh_3)_4$ (0.049 g, 0.042 mmol) was added and the vessel was sealed. The reaction mixture was stirred and heated in a microwave reactor at 140° C. for 15 min. The reaction was poured into water and the mixture was extracted with EtOAc. The combined organic extracts were washed with water, saturated sodium chloride, and dried over sodium sulfate. The solution was filtered and concentrated in vacuo to give the crude material. The crude material was purified by reverse-phase preparative HPLC with 0.1% TFA in $CH_3CN/H_2O$, gradient 5-70% over 20 min to provide 6-(2-(4-chloro-3-methyl-1H-pyrazol-1-yl)-6-methylphenyl)-3-morpholinoquinolin-2-amine as a white solid. The purified compound was portioned between DCM and saturated sodium bicarbonate. The layers were separated and the aqueous layer was extracted with DCM. The combined organic extracts were washed with saturated sodium chloride and dried over sodium sulfate. The solution was filtered and concentrated in vacuo to give 6-(2-(4-chloro-3-methyl-1H-pyrazol-1-yl)-6-methylphenyl)-3-morpholinoquinolin-2-amine as a white solid. MS (ESI, pos. ion) m/z: 434 (M+1).

Example 35

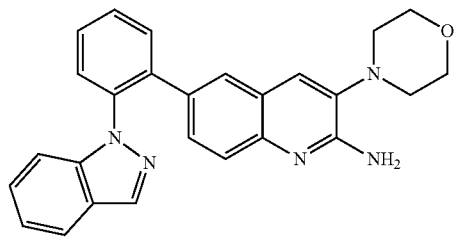 [SMILES: Nc1nc2ccc(-c3ccccc3-n3ncc4ccccc43)cc2cc1N1CCOCC1]

Synthesis of 6-(2-(1H-indazol-1-yl)phenyl)-3-morpholinoquinolin-2-amine

Step 1:
Sulfuric acid (7.67 mL, 144 mmol) was added to a solution of 2-(1H-indazol-1-yl)aniline (1.771 g, 8.46 mmol) in concentrated HCl (2.030 mL, 25.4 mmol) at 0° C. The solution was stirred and after cooling back to 0° C., sodium nitrite (0.584 g, 8.46 mmol) in water (3.5 mL) was added dropwise. The reaction was stirred 40 min at 0° C. before potassium iodide (2.81 g, 16.93 mmol) in water (3.5 mL) was added dropwise and the solution was stirred at RT. After 1 h, the reaction is poured into ice with ethyl acetate and separated. The aqueous layer was extracted with EtOAc. The combined organic extracts were washed with 1N HCl, water, saturated sodium bicarbonate, 1N sodium sulfite, and dried over sodium sulfate. The solution was filtered and concentrated in vacuo to give the crude material as an orange oil. The crude material was purified by silica gel chromatography by eluting with 1:4 EtOAc in hexane, to provide 1-(2-iodophenyl)-1H-indazole.

Step 2:
A mixture of 1-(2-iodophenyl)-1H-indazole (0.18 g, 0.563 mmol), 3-morpholino-6-(4,4,5,5-tetramethyl-1,3,2-dioxaborolan-2-yl)quinolin-2-amine (0.10 g, 0.282 mmol, prepared as in Example 2, Step 1-2), potassium phosphate tribasic (0.12 mL, 1.408 mmol), $Pd_2(dba)_3$ (0.026 g, 0.028 mmol), and 2-(dicyclohexylphosphino)-2',4',6',-tri-1-propyl-1,1'-biphenyl (0.027 g, 0.056 mmol) in dioxane/water (3/1.5 mL) was heated in mw for 12 min at 140° C. The mixture was concentrated and chromatographed on silica gel using 0-5% 2M $NH_3$ MeOH/DCM to afford a light yellow oil which was repurified by HPLC to afford a white solid as 6-(2-(1H-indazol-1-yl)phenyl)-3-morpholinoquinolin-2-amine. MS (ESI, pos. ion) m/z: 422 (M+1).

Example 36

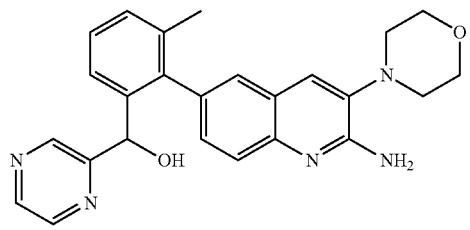 [SMILES: Cc1cccc(C(O)c2cnccn2)c1-c1ccc2nc(N)c(N3CCOCC3)cc2c1]

Synthesis of (2-(2-amino-3-morpholinoquinolin-6-yl)-3-methylphenyl)(pyrazin-2-yl)methanol Step 1:

A solution of 2-iodopyrazine (0.48 mL, 4.85 mmol) in dry THF (3 mL) was brought to 0° C. followed by the slowly addition of butylmagnesium chloride, 2.0M solution in THF (2.4 mL, 4.85 mmol). The resulting dark solution was stirred at 0° C. for 30 min then a solution of 2-bromo-3-methylbenzaldehyde (1.06 g, 5.34 mmol) in THF (2 mL) was slowly added and kept at 0° C. for 2 h. The mixture was quenched with saturated $NH_4Cl$ and extracted with DCM. The combined organics were washed with brine, dried over $Na_2SO_4$, filtered, concentrated and purified by silica gel column chromatography using gradient 1:1 hexanes/EtOAc to afford a yellow-orange oil as (2-bromo-3-methylphenyl)(pyrazin-2-yl)methanol.

Step 2:

A mixture of (2-bromo-3-methylphenyl)(pyrazin-2-yl)methanol (0.295 g, 1.056 mmol), 3-morpholino-6-(4,4,5,5-tetramethyl-1,3,2-dioxaborolan-2-yl)quinolin-2-amine (0.25 g, 0.704 mmol, prepared as Example 2, Step 1-2), potassium phosphate tribasic (0.291 mL, 3.52 mmol), $Pd_2(dba)_3$ (0.064 g, 0.070 mmol), and 2-(dicyclohexylphosphino)-2',4',6',-tri-1-propyl-1,1'-biphenyl (0.067 g, 0.141 mmol) in dioxane/water (3/1.5 mL) was heated in a microwave for 12 min at 140° C. The mixture was concentrated and chromatographed on silica gel using 0-5% 2M $NH_3$ in MeOH/DCM to afford a brown oil which was re-purified by HPLC to afford (2-(2-amino-3-morpholinoquinolin-6-yl)-3-methylphenyl)(pyrazin-2-yl)methanol as a yellow solid. MS (ESI, pos. ion) m/z: 428 (M+1).

Example 37

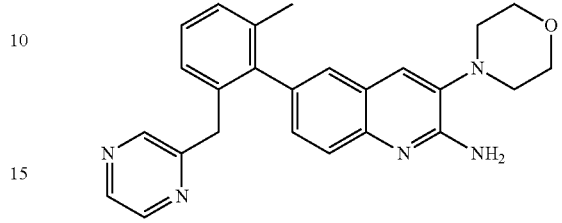

Synthesis of 6-(2-methyl-6-(pyrazin-2-ylmethyl)phenyl)-3-morpholinoquinolin-2-amine A solution of (2-(2-amino-3-morpholinoquinolin-6-yl)-3-methylphenyl)(pyrazin-2-yl)methanol (0.040 g, 0.094 mmol, prepared as Example 36 above) in i-PrOH and 5N HCl (15 mL) was refluxed for 15 h, or until starting material was consumed. The mixture was brought to RT, carefully washed with 5N NaOH and extracted with DCM. The combined organics were dried over $Na_2SO_4$, filtered, concentrated and purified by HPLC to afford a light brown solid as 6-(2-methyl-6-(pyrazin-2-ylmethyl)phenyl)-3-morpholinoquinolin-2-amine. MS (ESI, pos. ion) m/z: 412 (M+1).

Example 38

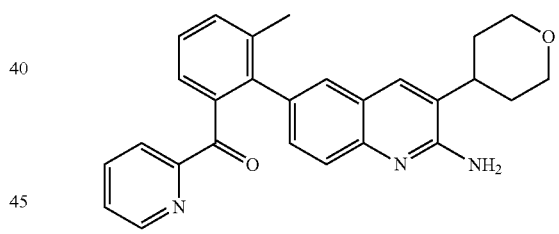

Synthesis of (2-(2-amino-3-(tetrahydro-2H-pyran-4-yl)quinolin-6-yl)-3-methylphenyl)(pyridin-2-yl)methanone Step 1:

N,N-dimethylformamide (0.27 mL, 3.47 mmol) was added to a solution of tetrahydropyranyl-4-acetic acid (5.0 g, 34.7 mmol) and thionyl chloride (2.53 mL, 34.7 mmol) in DCM (200 mL) at 0° C. After stirring 1 h at RT the solution was cooled to 0° C. N-Ethyl-N-isopropylpropan-2-amine (15.14 mL, 87 mmol) was added, followed by 4-bromoaniline (5.97 g, 34.7 mmol) in 20 mL DCM were added slowly and the solution was stirred at 0° C. After 1 h the reaction was diluted with saturated ammonium chloride and the organics were removed. Ethyl acetate was added and the layers were separated. The aqueous layer was extracted with EtOAc. The combined organic extracts were washed with water, saturated sodium chloride, and dried over sodium sulfate. The solution was filtered and concentrated in vacuo to give the crude material N-(4-bromophenyl)-2-(tetrahydro-2H-pyran-4-yl)acetamide as a tan solid.

Step 2:

N,N-dimethylformamide (1.0 mL, 13.41 mmol) was added slowly to phosphoryl trichloride (6.23 mL, 67.1 mmol) at 0° C. in a 20 mL microwave vessel under atmosphere of nitrogen gas. The solution was stirred 10 min at 0° C. and then ten minutes at RT before N-(4-bromophenyl)-2-(tetrahydro-2H-pyran-4-yl)acetamide (4.0 g, 13.4 mmol) was added in one portion. The vial was sealed and the mixture was stirred. The homogenous reaction mixture was stirred and heated in a microwave reactor at 100° C. for 22 min. After cooling, the reaction is poured into ice and extracted with EtOAc. The pH of the aqueous layer is adjusted to pH 2 with 5N NaOH and extracted with EtOAc. The combined organic extracts were washed with 1N NaOH, saturated sodium chloride, and dried over sodium sulfate. The solution was filtered and concentrated in vacuo to give the crude material. The crude material was purified by filtering through a plug of silica gel by eluting with 1:10 to 1:4 EtOAc in hexane, to provide 6-bromo-2-chloro-3-(tetrahydro-2H-pyran-4-yl) as white solid.

Step 3:

A glass microwave reaction vessel was charged with 6-bromo-2-chloro-3-(tetrahydro-2H-pyran-4-yl)quinoline (1.46 g, 4.47 mmol) and (4-methoxyphenyl)methanamine (5.80 mL, 44.7 mmol) in N-methyl-2-pyrrolidinone (5.80 mL). The reaction mixture was stirred and heated in a microwave reactor at 130° C. for 180 min. The reaction mixture was poured into water and extracted with EtOAc and DCM. The combined organic extracts were washed with saturated ammonium chloride, water, saturated sodium chloride, and dried over sodium sulfate. The solution was filtered and concentrated in vacuo to give the crude material as a yellow oil. The crude material was purified by silica gel chromatography by eluting with 1:4 to 1:1 EtOAc in hexane, to provide 6-bromo-N-(4-methoxybenzyl)-3-(tetrahydro-2H-pyran-4-yl)quinolin-2-amine as yellow solid.

Step 4:

The product of step 3 was carried forward using a procedure similar to that described in Example 28, Step 4, but using 6-bromo-N-(4-methoxybenzyl)-3-(tetrahydro-2H-pyran-4-yl)quinolin-2-amine to prepare N-(4-methoxybenzyl)-3-(tetrahydro-2H-pyran-4-yl)-6-(4,4,5,5-tetramethyl-1,3,2-dioxaborolan-2-yl)quinolin-2-amine from 6-bromo-N-(4-methoxybenzyl)-3-(tetrahydro-2H-pyran-4-yl)quinolin-2-amine.

Step 5:

A mixture of 2-bromo-3-methylbenzonitrile (0.744 g, 3.79 mmol), N-(4-methoxybenzyl)-3-(tetrahydro-2H-pyran-4-yl)-6-(4,4,5,5-tetramethyl-1,3,2-dioxaborolan-2-yl)quinolin-2-amine (0.60 g, 1.265 mmol), 2-(dicyclohexylphosphino)-2',4',6',-tri-1-propyl-1,1'-biphenyl (0.121 g, 0.253 mmol), potassium phosphate, anhydrous (0.524 mL, 6.32 mmol), and Pd$_2$(dba)$_3$ (0.116 g, 0.126 mmol) was purged with N$_2$ followed by the addition of degassed dioxane (2 mL) and degassed water (1.0 mL). The resulting mixture was heated in microwave at 140° C. for 12 min. The reaction went to completion and it was filtered, concentrated, and chromatographed on silica gel using gradient 2:1 hexanes/EtOAc to afford a yellow solid as (2-(2-(4-methoxybenzylamino)-3-(tetrahydro-2H-pyran-4-yl) quinolin-6-yl)-3-methylbenzonitrile.

Step 6:

To a dry flask was added isopropylmagnesium chloride (1.68 mL, 3.37 mmol) 2.0 M in THF followed by the addition of 2-iodopyridine (0.66 g, 3.24 mmol). After 2 h stirring at RT to this mixture was added 2-(2-(4-methoxybenzylamino)-3-(tetrahydro-2H-pyran-4-yl) quinolin-6-yl)-3-methylbenzonitrile (0.30 g, 0.647 mmol) and heated at 60° C. for 17 h. The mixture was brought RT and 5N HCl (3 mL) was slowly added. The resulting mixture was heated at 60° C. for 4 h until it went to completion. The mixture was concentrated, and purified by column chromatography on silica gel eluting with 0-5% 2M NH$_3$ in MeOH/DCM to afford a light yellow solid as (2-(2-amino-3-(tetrahydro-2H-pyran-4-yl)quinolin-6-yl)-3-methylphenyl)(pyridin-2-yl)methanone. MS (ESI, pos. ion) m/z: 424 (M+1).

Example 39

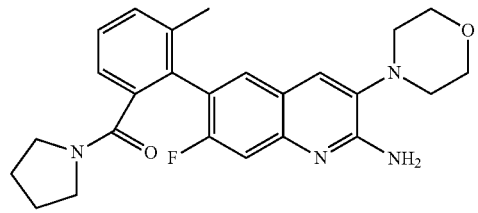 [SMILES: Cc1cccc(C(=O)N2CCCC2)c1-c1cc2cc(N3CCOCC3)c(N)nc2cc1F]

Synthesis of (2-(2-amino-7-fluoro-3-morpholinoquinolin-6-yl)-3-methylphenyl)(pyrrolidin-1-yl)methanone Step 1:

To a 0° C. solution of concentrated sulfuric acid (125 mL, 2340 mmol) and nitric acid (11.79 mL, 185 mmol) was added 3-bromo-4-fluorobenzaldehyde (25.0 g, 123 mmol). The reaction was warmed to ambient temperature, during which time the solids dissolved. After 2 h, the reaction mixture was poured into a mixture of ice (500 mL) and water (250 mL). The resulting suspension was filtered through a medium frit affording 5-bromo-4-fluoro-2-nitrobenzaldehyde as a yellow solid.

Step 2:

To a suspension of Pt/C (10%, 1.5 g, 0.77 mmol) in DCM (200 mL) and THF (50 mL) was added 5-bromo-4-fluoro-2-nitrobenzaldehyde (9.0 g, 36.3 mmol). The mixture was purged with H$_2$ gas, and was stirred under an atmosphere of H$_2$ gas at ambient temperature for 24 h. The reaction mixture was filtered through celite rinsing with DCM. The filtrate was concentrated and the residue was purified by column chromatography on silica gel (600 mL) eluting with 15% EtOAc/hexane to afford 2-amino-5-bromo-4-fluorobenzaldehyde.

Step 3:

To a solution of 2-morpholinoacetonitrile (1.29 g, 10.26 mmol) in DMSO (13 mL) was added aqueous KOH (11.7 M, 0.276 mL, 3.23 mmol). The reaction was heated at 80° C., and a solution of 2-amino-5-bromo-4-fluorobenzaldehyde (1.41 g, 6.45 mmol) in DMSO (13 mL) was added dropwise over 2.5 h. The reaction mixture was stirred at 80° C. for 14 h. It was then cooled to RT and diluted with water (200 mL) and saturated NH$_4$Cl (5 mL). The aqueous phase was extracted with DCM (2×200 mL). The organic fractions were combined, washed with half-saturated brine (4×300 mL), dried over sodium sulfate and concentrated. The residue was purified by column chromatography on silica gel (150 mL) which had been deactivated with TEA (15 mL) eluting with 75:25:1:0.5 EtOAc/hexane/MeOH/Et$_3$N to afford 6-bromo-7-fluoro-3-morpholinoquinolin-2-amine.

Step 4:

A microwave vessel was charged with potassium acetate (0.34 g, 3.46 mmol), [1,1'-bis(dppf)]dichloropalladium(II) complex with $CH_2Cl_2$ (0.038 g, 0.052 mmol), 4,4,4',4',5,5,5',5'-octamethyl-2,2'-bi(1,3,2-dioxaborolane) (0.211 g, 0.831 mmol), 6-bromo-7-fluoro-3-morpholinoquinolin-2-amine (0.226 g, 0.693 mmol), and DMF (2.2 mL). The vessel was purged with argon, sealed, and heated by microwave radiation for 30 min at 125° C. The reaction was diluted with EtOAc (10 mL), and the suspension was filtered through celite rinsing with EtOAc. The filtrate was concentrated. The residue was purified by column chromatography on silica gel (25 mL) which had been deactivated with $Et_3N$ (2.5 mL) using 3% MeOH/DCM to afford 2-amino-7-fluoro-3-morpholinoquinolin-6-ylboronic acid.

Step 5:

A microwave vessel was charged with (2-bromo-3-methylphenyl)(pyrrolidin-1-yl)methanone (0.081 g, 0.301 mmol), dicyclohexyl(2',4',6'-triisopropylbiphenyl-2-yl)phosphine (0.018 g, 0.038 mmol), $Pd_2(dba)_3$ (0.018 g, 0.020 mmol), potassium phosphate (0.106 g, 0.502 mmol), 2-amino-7-fluoro-3-morpholinoquinolin-6-ylboronic acid (0.073 g, 0.251 mmol), dioxane (1.6 mL) and water (0.8 mL). The vessel was purged with argon, sealed and heated by microwave radiation at 140° C. for 15 min. The mixture was concentrated, diluted with EtOAc (10 mL) and the suspension was filtered through celite rinsing with EtOAc. The filtrate was washed with saturated brine (5 mL), dried over sodium sulfate and concentrated. The material was purified by column chromatography on silica gel (33 mL) which had been deactivated with $Et_3N$ (3.3 mL) eluting with 1.5% MeOH/EtOAc to afford (2-(2-amino-7-fluoro-3-morpholinoquinolin-6-yl)-3-methylphenyl)(pyrrolidin-1-yl)methanone. MS (ESI, pos. ion) m/z: 435 (M+1).

Example 40

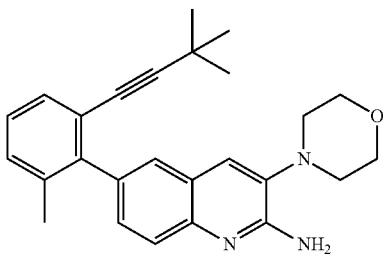 [SMILES: Cc1cccc(C#CC(C)(C)C)c1-c1ccc2nc(N)c(N3CCOCC3)cc2c1]

Synthesis of 6-(2-(3,3-dimethylbut-1-ynyl)-6-methylphenyl)-3-morpholinoquinolin-2-amine Step 1:

A flask was charged with bis(triphenylphosphine)palladium(II)chloride (0.042 g, 0.060 mmol) and copper(I) iodide (0.023 g, 0.120 mmol) under nitrogen atmosphere. THF (4.6 mL) was added, followed by 2-bromo-1-iodo-3-methylbenzene (0.594 g, 2 mmol), triethylamine (2.3 mL, 16.50 mmol) and 3,3-dimethylbutyne (0.251 mL, 2.040 mmol). The reaction mixture was allowed to stir at RT overnight. The reaction mixture was filtered through a plug of silica gel and the plug was rinsed with $Et_2O$. The solvent was removed under reduced pressure and the remaining residue was purified by flash chromatography (0-2% EtOAc/hexanes). 2-Bromo-1-(3,3-dimethylbut-1-ynyl)-3-methylbenzene was obtained as a light-yellow clear oil.

Step 2:

A microwave vial was charged with a mixture of 2-dicyclohexylphosphino-2',4',6'-triisopropylbiphenyl (0.040 g, 0.084 mmol), $Pd_2(dba)_3$ (0.019 g, 0.021 mmol), 3-morpholino-6-(4,4,5,5-tetramethyl-1,3,2-dioxaborolan-2-yl)quinolin-2-amine (0.15 g, 0.422 mmol, prepared as in Example 2, Step 1-2) and potassium phosphate (0.175 mL, 2.11 mmol). The vial was evacuated and backfilled with $N_2$. This procedure was repeated twice. Degassed dioxane (2.8 mL) and water (1.4 mL) was added. Then 2-bromo-1-(3,3-dimethylbut-1-ynyl)-3-methylbenzene (0.138 g, 0.549 mmol) was added and the reaction mixture was heated to 140° C. for 12 min in the microwave. The reaction mixture was cooled to RT and partitioned between EtOAc and water. The organic phase was washed with brine and dried over $MgSO_4$. The solvent was removed under reduced pressure and the remaining residue was purified by flash chromatography (50-100% EtOAc/hexanes). The obtained solid was dissolved in MeOH (4 mL) and treated with 1N HCl (1 mL). The solution was eluted on an SCX cartridge with MeOH followed by 2M $NH_3$/MeOH. The basic fraction was concentrated to afford the titled compound as a beige foam. MS (ESI, pos. ion) m/z: 400 (M+1).

Example 41

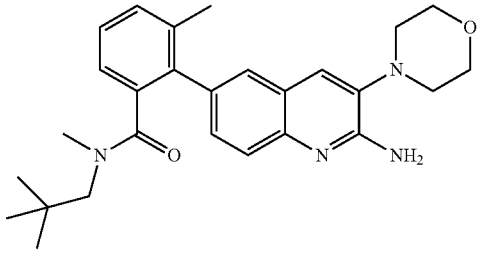 [SMILES: Cc1cccc(C(=O)N(C)CC(C)(C)C)c1-c1ccc2nc(N)c(N3CCOCC3)cc2c1]

Synthesis of 2-(2-amino-3-morpholinoquinolin-6-yl)-N,3-dimethyl-N-neopentylbenzamide Step 1:

A solution of 2-bromo-3-methylbenzoic acid (2.150 g, 10 mmol) and HATU (3.80 g, 10.00 mmol) in DMF (20 mL) was stirred for 10 min at RT. Neopentylamine (1.170 mL, 10.00 mmol) was slowly added and the reaction mixture was allowed to stir at RT overnight. The reaction was quenched with 1N HCl and the solution was partitioned between brine and EtOAc. The aqueous phase was extracted with EtOAc. The organic phases were combined and dried over $MgSO_4$. The solvent was removed under reduced pressure and the remaining residue was purified by flash chromatography (6-50% EtOAc/hexanes). 2-Bromo-3-methyl-N-neopentylbenzamide was isolated as a white solid.

Step 2:

To a slurry of NaH (60% in mineral oil) (0.122 mL, 2.81 mmol) in THF (5 ml) was added dropwise a solution of 2-bromo-3-methyl-N-neopentylbenzamide (400 mg, 1.407 mmol) in THF (1 ml) at RT. After 20 min, iodomethane (0.096 mL, 1.548 mmol) was added and the reaction was allowed to stir for 48 h. The reaction was quenched by the addition of water and EtOAc. The organic phase was separated and dried over MgSO₄. The solvent was removed under reduced pressure and the residue was purified by flash chromatography (6-48% EtOAc/hexanes). 2-Bromo-N,3-dimethyl-N-neopentylbenzamide was isolated as a clear colorless viscous oil.

Step 3:

The product of step 2 was carried forward in a manner analogous to the procedure described in Example 40, Step 2, but using 2-bromo-N,3-dimethyl-N-neopentylbenzamide as the starting material, to afford the titled compound as an off-white powder. MS (ESI, pos. ion) m/z: 447 (M+1).

Example 42

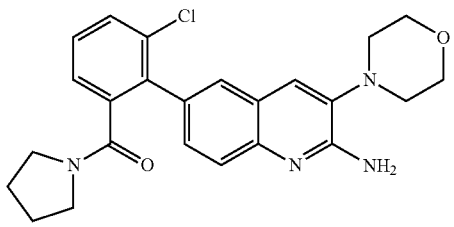 [SMILES: Nc1nc2ccc(-c3c(Cl)cccc3C(=O)N3CCCC3)cc2cc1N1CCOCC1]

Synthesis of (2-(2-amino-3-morpholinoquinolin-6-yl)-3-chlorophenyl)(pyrrolidin-1-yl)methanone Step 1:

(3-chloro-2-iodophenyl)(pyrrolidin-1-yl)methanone was prepared by a method analogous to the procedure described in Example 1, Step 5.

Step 2:

A vial was charged with 3-morpholino-6-(4,4,5,5-tetramethyl-1,3,2-dioxaborolan-2-yl)quinolin-2-amine (710 mg, 2.000 mmol, prepared as in Example 2, Step 1-2), (3-chloro-2-iodophenyl)(pyrrolidin-1-yl)methanone (671 mg, 2 mmol), Pd(OAc)₂ (22.45 mg, 0.100 mmol), triphenylphosphine (52.5 mg, 0.200 mmol) and potassium phosphate (0.331 mL, 4.00 mmol). The vial was evacuated and backfilled with nitrogen gas 3×. ACN (8 mL) and water (2 mL) were added and the reaction mixture was heated to 60° C. overnight in an oil bath. The product precipitated out of solution and was filtered off, dissolved in DCM/MeOH, washed with water and dried over MgSO₄. The solvent was removed and the solid was dried under vacuum at 50° C. This material was further purified by preparative HPLC (10-100%; water with 0.1% TFA/CH₃CN, 11 min). The obtained product was eluted on an SCX cartridge with MeOH followed by 2M NH₃ in MeOH. The basic fraction was concentrated to afford the titled compound as a light-yellow solid. MS (ESI, pos. ion) m/z: 437 (M+1).

Example 43

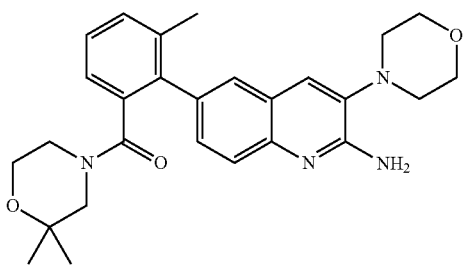 [SMILES: Cc1cccc(C(=O)N2CCOC(C)(C)C2)c1-c1ccc2nc(N)c(N3CCOCC3)cc2c1]

Synthesis of (2-(2-amino-3-morpholinoquinolin-6-yl)-3-methylphenyl)(2,2-dimethylmorpholino)methanone Step 1:

A solution of 2-bromo-3-methylbenzoic acid (344 mg, 1.6 mmol) and HATU (913 mg, 2.400 mmol) in DMF (10 mL) was stirred for 10 min at RT. 2,2-Dimethylmorpholine hydrochloride (364 mg, 2.400 mmol) and 1,1'-dimethyl triethylamine (2.23 mL, 12.80 mmol) were added and the reaction mixture was allowed to stir for 4 h at RT Ammonium chloride solution and EtOAc was added. The organic phase was separated and washed twice with brine. The organic phase was dried over MgSO₄ and the solvent was removed under reduced pressure. The remaining residue was purified by flash chromatography (40-100% EtOAc/hexanes). (2-Bromo-3-methylphenyl)(2,2-dimethylmorpholino)methanone was obtained as a yellow oil.

Step 2:

The product of step 1 was carried forward using a procedure similar to that described in Example 40, Step 2, but using (2-bromo-3-methylphenyl)(2,2-dimethylmorpholino)methanone, to afford the titled compound as a beige solid. MS (ESI, pos. ion) m/z: 461 (M+1).

Example 44

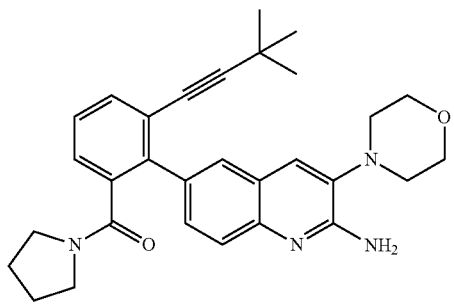 [SMILES: CC(C)(C)C#Cc1cccc(C(=O)N2CCCC2)c1-c1ccc2nc(N)c(N3CCOCC3)cc2c1]

Synthesis of (2-(2-amino-3-morpholinoquinolin-6-yl)-3-(3,3-dimethylbut-1-ynyl)phenyl)(pyrrolidin-1-yl)methanone A microwave vial was charged with (2-(2-amino-3-morpholinoquinolin-6-yl)-3-chlorophenyl)(pyrrolidin-1-yl)

methanone (273 mg, 0.625 mmol, see Example 42), dichlorobis(acetonitrile)-palladium(II) (24.31 mg, 0.094 mmol), 2-dicyclohexylphosphino-2',4',6'-triisopropylbiphenyl (134 mg, 0.281 mmol) and cesium carbonate (529 mg, 1.625 mmol). The vial was evacuated and backfilled with nitrogen gas 2×. ACN (2 mL) was added and the reaction mixture was allowed to stir RT for 25 min. 1-Hexyne (0.100 mL, 0.812 mmol) was added and the reaction mixture was heated to 105° C. for 2 h. The reaction mixture was cooled to RT, diluted with MeOH and filtered through a plug of celite. The solvent was removed under reduced pressure and the remaining residue was purified by preparative HPLC (10-100% water with 0.1% TFA/CH$_3$CN, 11 min). The product obtained was eluted on an SCX cartridge with MeOH followed by 2M NH$_3$/MeOH. The basic fraction was concentrated to afford the titled compound as a light-yellow solid. MS (ESI, pos. ion) m/z: 483 (M+1).

Example 45

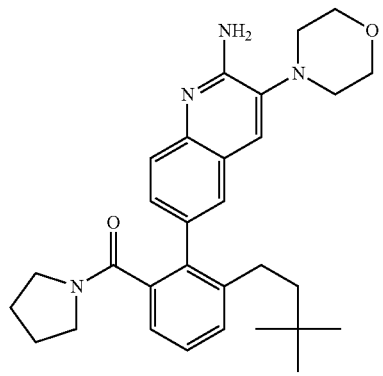 [SMILES: CC(C)(C)CCc1cccc(C(=O)N2CCCC2)c1-c1ccc2nc(N)c(N3CCOCC3)cc2c1]

Synthesis of (2-(2-amino-3-morpholinoquinolin-6-yl)-3-(3,3-dimethylbutyl)phenyl)(pyrrolidin-1-yl)methanone To a solution of (2-(2-amino-3-morpholinoquinolin-6-yl)-3-(3,3-dimethylbut-1-ynyl)phenyl)(pyrrolidin-1-yl)methanone (89 mg, 0.184 mmol, see Example 44) in ethanol (10 mL) was added palladium on activated carbon (10% wt; 150 mg). The reaction mixture was evacuated and backfilled with nitrogen gas. Then the reaction mixture was evacuated and backfilled with hydrogen gas. The reaction mixture was allowed to stir for 8 h at RT. The reaction mixture was filtered through a pad of celite. The solvent was removed under reduced pressure and the remaining residue was purified by column chromatography (10% MeOH in DCM). The titled compound was obtained as a light-yellow powder. MS (ESI, pos. ion) m/z: 487 (M+1).

Example 46

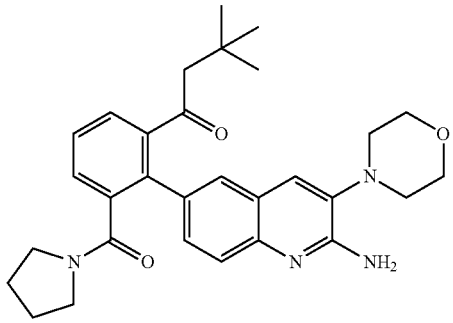 [SMILES: CC(C)(C)CC(=O)c1cccc(C(=O)N2CCCC2)c1-c1ccc2nc(N)c(N3CCOCC3)cc2c1]

Synthesis of 1-(2-(2-amino-3-morpholinoquinolin-6-yl)-3-(pyrrolidine-1-carbonyl)phenyl)-3,3-dimethylbutan-1-one A solution of (2-(2-amino-3-morpholinoquinolin-6-yl)-3-(3,3-dimethylbut-1-ynyl)phenyl)(pyrrolidin-1-yl)methanone (188 mg, 0.390 mmol, see Example 45) in formic acid (>96%) (10 mL, 265 mmol) was heated to 110° C. After 4 days CH$_2$Cl$_2$ was added and the solution was washed with water and sodium carbonate solution. The organic phase was separated and dried over MgSO$_4$. The solvent was removed under reduced pressure and the remaining residue was purified by preparative HPLC (10-100% water with 0.1% TFA/CH$_3$CN, 11 min). The obtained product was eluted on an SCX cartridge with MeOH followed by 2M NH$_3$/MeOH. The basic fraction was concentrated to afford the titled compound as a white powder. MS (ESI, pos. ion) m/z: 501 (M+1).

Example 47

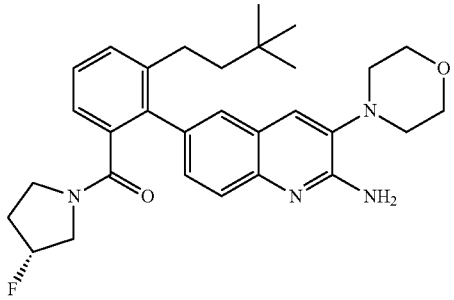 [SMILES: CC(C)(C)CCc1cccc(C(=O)N2CC[C@@H](F)C2)c1-c1ccc2nc(N)c(N3CCOCC3)cc2c1]

Synthesis of (R)-(2-(2-amino-3-morpholinoquinolin-6-yl)-3-(3,3-dimethylbutyl)phenyl)(3-fluoropyrrolidin-1-yl)methanone Step 1:
A vial was charged with 3-morpholino-6-(4,4,5,5-tetramethyl-1,3,2-dioxaborolan-2-yl)quinolin-2-amine (1.07 g, 3 mmol, prepared as in Example 2, Step 1-2), methyl 3-chloro-2-iodobenzoate (889 mg, 3.00 mmol), Pd(OAc)$_2$ (33.7 mg, 0.150 mmol), triphenylphosphine (79 mg, 0.300 mmol) and potassium phosphate (0.497 mL, 6.00 mmol). The vial was evacuated and backfilled with nitrogen gas 3×. Acetonitrile (8 mL) and Water (2 mL) were added and the reaction mixture was heated to 60° C. overnight in an oil bath. The reaction mixture was partitioned between water and ethyl acetate. The organic phase was separated and dried over MgSO₄. The solvent was removed under reduced pressure and the residue was purified by column chromatography (5% MeOH in DCM). Methyl 2-(2-amino-3-morpholinoquinolin-6-yl)-3-chlorobenzoate was obtained as a yellow powder.

Step 2:
A vial was charged with methyl 2-(2-amino-3-morpholinoquinolin-6-yl)-3-chlorobenzoate (841 mg, 2.114 mmol), dichlorobis(acetonitrile)palladium(II) (54.8 mg, 0.211 mmol), 2-dicyclohexylphosphino-2',4',6'-triisopropylbiphenyl (302 mg, 0.634 mmol) and cesium carbonate (1.79 g, 5.50 mmol). The vial was evacuated and backfilled with nitrogen gas 3×. ACN (9 mL) was added and the suspension was allowed to stir at RT for 20 min. 3,3-Dimethyl-1-butyne (0.521 mL, 4.23 mmol) was added and the reaction mixture was heated to 90° C. for 3.5 h. The reaction mixture was partitioned between water and EtOAc. The organic phase was separated and dried over MgSO₄. The solvent was removed under reduce pressure and the remaining residue was purified by column chromatography (10% MeOH in DCM). Methyl 2-(2-amino-3-morpholinoquinolin-6-yl)-3-(3,3-dimethyl-but-1-ynyl)benzoate was obtained as an orange-brown solid.

Step 3:
To a solution of methyl 2-(2-amino-3-morpholinoquinolin-6-yl)-3-(3,3-dimethylbut-1-ynyl)benzoate (655 mg, 1.477 mmol) in ethanol (30 mL) and EtOAc (5 mL) was added palladium on activated carbon (10% wt., 400 mg). The reaction mixture was evacuated and backfilled with nitrogen gas. The reaction mixture was evacuated and backfilled with hydrogen gas. The reaction mixture was allowed to stir overnight at RT. The reaction mixture was filtered through a pad of celite and the filtrate was concentrated. Ethanol (10 mL) and palladium on activated carbon (10% wt., 500 mg) were added. The reaction mixture was evacuated and backfilled with hydrogen and allowed to stir overnight at RT. The reaction mixture was filtered through a pad of celite. The solvent was removed under reduced pressure and methyl 2-(2-amino-3-morpholinoquinolin-6-yl)-3-(3,3-dimethylbutyl)benzoate was obtained as a yellow-tan residue and used in the next reaction without further purification.

Step 4:
A solution of methyl 2-(2-amino-3-morpholinoquinolin-6-yl)-3-(3,3-dimethylbutyl)benzoate (520 mg, 1.162 mmol) in MeOH (20 mL) and 5N NaOH (0.929 mL, 4.65 mmol) was heated to 80° C. for 7 h. The solution was cooled to RT and acidified with 5N HCl to pH of ~4. The solution was concentrated under reduced pressure. The residue was dissolved in MeOH and filtered. The filtrate was concentrated under reduced pressure to yield 2-(2-amino-3-morpholinoquinolin-6-yl)-3-(3,3-dimethylbutyl)benzoic acid hydrochloride as a brown solid which was used without further purification.

Step 5:
A solution of 2-(2-amino-3-morpholinoquinolin-6-yl)-3-(3,3-dimethylbutyl)benzoic acid hydrochloride (168 mg, 0.357 mmol) and HATU (204 mg, 0.536 mmol) in DMF (5 mL) was stirred for 10 min at RT. (R)-(−)-3-fluoropyrrolidine hydrochloride (224 mg, 1.787 mmol) and 1,1'-dimethyltriethylamine (0.622 mL, 3.57 mmol) were added and the reaction mixture was allowed to stir overnight at RT. The reaction mixture was partitioned between water and ethyl acetate. The organic phase was separated, dried over MgSO₄ and the solvent was removed under reduced pressure. The residue was purified by preparative HPLC (10-100% water with 0.1% TFA/CH₃CN, 11 min). The obtained product was eluted on an SCX cartridge with MeOH followed by 2M NH₃/MeOH. The basic fraction was concentrated to afford the titled compound as a white solid. MS (ESI, pos. ion) m/z: 505 (M+1).

Example 48

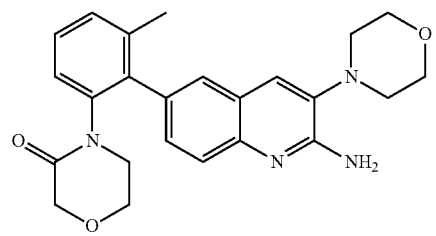 [SMILES: Cc1cccc(N2CCOCC2=O)c1-c1ccc2nc(N)c(N3CCOCC3)cc2c1]

Synthesis of 4-(2-(2-amino-3-morpholinoquinolin-6-yl)-3-methylphenyl)morpholin-3-one Step 1:
To a stirred slurry of NaH (60% in mineral oil) (0.435 mL, 10.00 mmol) in THF (5 ml) was added dropwise a solution of 2-bromo-3-methylaniline (0.625 mL, 5 mmol) in THF (1 ml). After 15 min, (2-bromoethoxy)-tert-butyldimethylsilane (1.07 mL, 5 mmol) was added and the reaction mixture was stirred for 48 h. The reaction was quenched with water, partitioned between EtOAc and aqueous saturated ammonium chloride. The aqueous layer was extracted with EtOAc and the combined organic layers were dried over MgSO₄. The solvent was removed under reduced pressure and the remaining residue was purified by flash chromatography (0-10% EtOAc/hexanes). 2-Bromo-N-(2-(tert-butyldimethylsilyloxy)ethyl)-3-methylaniline was isolated as a yellow oil.

Step 2:
To a 50-mL RBF was added 2-bromo-N-(2-(tert-butyldimethylsilyloxy)ethyl)-3-methylaniline (1.43 g, 4.15 mmol) and THF (10 mL). A solution of TBAF (1.0M in THF; 4.98 mL, 4.98 mmol) was added dropwise at RT. The reaction mixture was allowed to stir for 1.5 h at RT. The solvent was removed under reduced pressure. The remaining residue was purified by flash chromatography (5-60% EtOAc/hexanes). 2-(2-Bromo-3-methylphenylamino)ethanol was isolated as a clear yellow oil.

Step 3:
To a solution of THF were added successively potassium tert-butoxide (572 mg, 5.10 mmol), 2-(2-bromo-3-methylphenylamino)ethanol (1151 mg, 5 mmol) and ethyl 2-chloroacetate (0.565 mL, 5.30 mmol). The resulting suspension was stirred for 16 h at RT. Additional KOtBu (200 mg) and ethyl 2-chloroacetate (0.15 ml) were added and the reaction mixture was heated to 36° C. for additional 2 h. The reaction was quenched with water and 1M HCl, followed by addition of EtOAc. The organic phase was separated, washed with brine and dried over MgSO₄. The solvent was removed under reduced pressure and the remaining residue was purified by flash chromatography (5-70% EtOAc/hexanes). 4-(2-Bromo-3-methylphenyl)morpholin-3-one was obtained as a light-yellow powder.

Step 4:
The titled compound was obtained by a method similar to that described in Example 40, Step 2, but using 4-(2-bromo- 3-methylphenyl)morpholin-3-one. The titled compound was a white solid. (ESI, pos. ion) m/z: 419 (M+1).

Example 49

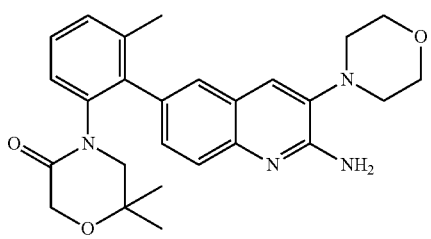 [SMILES: Cc1cccc(N2CC(C)(C)OCC2=O)c1-c1ccc2nc(N)c(N3CCOCC3)cc2c1]

Synthesis of 4-(2-(2-amino-3-morpholinoquinolin-6-yl)-3-methylphenyl)-6,6-dimethylmorpholin-3-one Step 1:
To a solution of lithium perchlorate (2.13 g, 20 mmol) in diethyl ether (4 mL) was added 1,2-epoxy-2-methylpropane (0.195 mL, 2.2 mmol), followed by 2-bromo-3-methylaniline (0.250 mL, 2 mmol) under an atmosphere of nitrogen gas. The reaction mixture was stirred overnight at RT. Water was added dropwise, and the product was extracted from the reaction mixture with DCM. The organic phase was dried over $MgSO_4$. The solvent was removed under reduced pressure and the remaining residue was purified by flash chromatography (10-40% hexanes/EtOAc). 1-(2-bromo-3-methylphenylamino)-2-methylpropan-2-ol was obtained as a clear colorless oil.

Step 2:
To a solution of potassium tert-butoxide (472 mg, 4.21 mmol) in THF (4 mL) was added a solution of 1-(2-bromo-3-methylphenylamino)-2-methylpropan-2-ol (724 mg, 2.80 mmol) in THF (10 mL), followed by ethyl 2-chloroacetate (0.45 mL, 4.21 mmol). After 1 h at RT an additional 1 eq of potassium t-butoxide (472 mg, 4.21 mmol) and ethyl 2-chloroacetate (0.450 mL, 4.21 mmol) were added. After 6 h water was added, followed by EtOAc. The organic phase was separated, dried over $MgSO_4$ and the solvent was removed under reduced pressure. The remaining residue was purified by flash chromatography (30-80% EtOAc/hexanes). 4-(2-Bromo-3-methylphenyl)-6,6-dimethylmorpholin-3-one was isolated as a light-yellow solid.

Step 3:
The titled compound was obtained by a method similar to that described in Example 40, Step 2, but using 4-(2-bromo-3-methylphenyl)-6,6-dimethylmorpholin-3-one. The titled compound was a yellow solid. MS (ESI, pos. ion) m/z: 447 (M+1).

Example 50

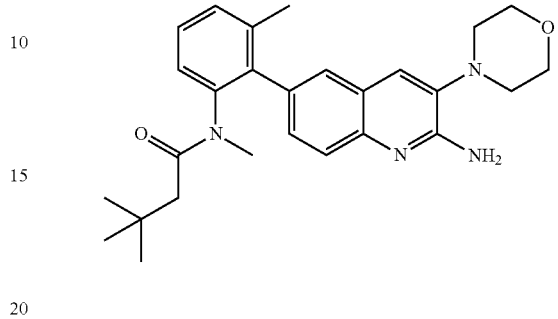

Synthesis of N-(2-(2-amino-3-morpholinoquinolin-6-yl)-3-methylphenyl)-N,3,3-trimethylbutanamide Step 1:
A solution of 2-bromo-3-methylaniline (0.93 mL, 7.4 mmol), DMAP (0.012 mg, 0.100 µmol) and 1,1'-dimethyl triethylamine (1.74 mL, 10.00 mmol) in DCM (15 mL) was cooled to 0° C. tert-Butylacetyl chloride (0.79 mL, 5.85 mmol) was added dropwise and the reaction mixture was allowed to stir at RT overnight. The reaction mixture was quenched with ammoniumchloride solution. The organic phase was separated and dried over $MgSO_4$. The solvent was removed under reduced pressure and the remaining residue containing N-(2-bromo-3-methylphenyl)-3,3-dimethylbutanamide was carried to step 2.

Step 2:
To a slurry of NaH in THF at 0° C. was added a solution of N-(2-bromo-3-methylphenyl)-3,3-dimethylbutanamide (1.42 g, 5.00 mmol) in THF. After 20 min at 0° C., methyl iodide (342 µL, 5.50 mmol) was added and the reaction mixture was allowed to stir at RT for 1 h. Additional 200 mg NaH and 0.34 ml MeI were added and the reaction was allowed to stir for 5 min. Water and EtOAc were added to the mixture, and the organic phase was separated and dried over $MgSO_4$. The solvent was removed under reduced pressure and the remaining residue was purified by flash column chromatography (0-20% EtOAc/hexanes). N-(2-bromo-3-methylphenyl)-N,3,3-trimethylbutanamide was isolated as a clear, colorless oil.

Step 3:
A vial was charged with 2-amino-5-bromobenzaldehyde (400 mg, 2 mmol), bis(pinacolato)diboron (609 mg, 2.400 mmol), 1,1'-bis(diphenylphosphino)ferrocene-palladium(II) dichloride dichloromethane complex (82 mg, 0.100 mmol) and potassium acetate (0.375 mL, 6.00 mmol). The vial was evacuated and backfilled with nitrogen gas three times. Dioxane (12 mL) was added and the reaction mixture was heated to 85° C. overnight in an oil bath. The reaction mixture was cooled to RT and the solution was filtered through a pad of celite. The material was absorbed onto a plug of silica gel and purified by flash chromatography (10-60% EtOAc/hexanes). 2-Amino-5-(4,4,5,5-tetramethyl-1,3,2-dioxaborolan-2-yl)benzaldehyde was obtained as a yellow solid.

Step 4:
A microwave vial was charged with N-(2-bromo-3-methylphenyl)-N,3,3-trimethylbutanamide (153 mg, 0.513 mmol), 12-amino-5-(4,4,5,5-tetramethyl-1,3,2-dioxaborolan-2-yl)benzaldehyde (121 mg, 0.490 mmol), Pd₂(dba)₃ (22.42 mg, 0.024 mmol), 2-dicyclohexylphosphino-2',4',6'-triisopropylbiphenyl (46.7 mg, 0.098 mmol) and potassium phosphate (0.203 mL, 2.448 mmol). The vial was evacuated and backfilled with nitrogen gas twice. The reaction mixture was heated to 140° C. for 12 min in the microwave. The reaction mixture was cooled to RT and partitioned between water and EtOAc. The organic phase was separated and dried over MgSO₄. The solvent was removed under reduced pressure and the remaining residue was purified by flash chromatography (5-50% EtOAc/hexanes). N-(4'-amino-3'-formyl-6-methylbiphenyl-2-yl)-N,3,3-trimethylbutanamide was isolated as a purple-grey foam.

Step 5:

A solution of 2-morpholinoacetonitrile (37.7 mg, 0.299 mmol) in DMSO (0.5 mL) was treated with concentrated aqueous KOH (11M; 8.08 µL, 0.095 mmol). The reaction mixture was heated to 80° C. and a solution of N-(4'-amino-3'-formyl-6-methylbiphenyl-2-yl)-N,3,3-trimethylbutanamide (64 mg, 0.189 mmol) in DMSO (1 mL) was added dropwise. After 10 min the reaction mixture was diluted with water and aqueous saturated ammonium chloride solution. The aqueous mixture was extracted with DCM. The organic phase was separated and dried over MgSO₄. The solvent was removed under reduced pressure and the remaining residue was purified by preparative HPLC (10-100% water with 0.1% TFA/CH₃CN, 11 min). The titled compound was isolated as a light-yellow foam. MS (ESI, pos. ion) m/z: 447 (M+1).

Example 51

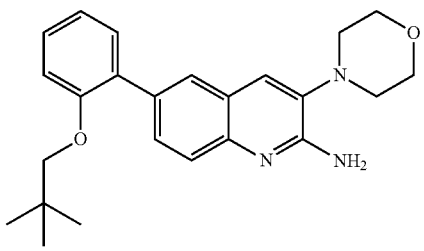 [SMILES: CC(C)(C)COc1ccccc1-c1ccc2nc(N)c(N3CCOCC3)cc2c1]

Synthesis of 3-morpholino-6-(2-(neopentyloxy)phenyl)quinolin-2-amine

Step 1:

A vial was charged with 1-bromo-2-iodobenzene (627 µL, 5 mmol), neopentyl alcohol (4.85 g, 55.0 mmol), copper(I) iodide (95 mg, 0.500 mmol), 1,10-phenanthroline (180 mg, 1.000 mmol) and cesium carbonate (2.28 g, 7.00 mmol). The vial was sealed under air atmosphere and heated to 100° C. for 12 h. The reaction mixture was cooled to RT and filtered through a pad of silica gel. The silica gel was washed with Et₂O. The filtrate was concentrated and the residue was purified by column chromatography (100% hexanes) to yield the 1-bromo-2-(neopentyloxy)benzene as a colorless oil.

Step 2:

The titled compound was obtained by a procedure similar to that described in Example 40, Step 2, but using 1-bromo-2-(neopentyloxy)benzene. The titled compound was obtained as a beige powder. (ESI, pos. ion) m/z: 392 (M+1).

Example 52

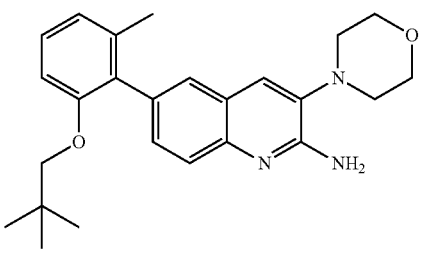 [SMILES: Cc1cccc(OCC(C)(C)C)c1-c1ccc2nc(N)c(N3CCOCC3)cc2c1]

Synthesis of 6-(2-methyl-6-(neopentyloxy)phenyl)-3-morpholinoquinolin-2-amine

Step 1:

A vial was charged with 2-bromo-1-iodo-3-methylbenzene (677 mg, 2.28 mmol), neopentyl alcohol (2.21 g, 25.08 mmol), copper(I) iodide (43.4 mg, 0.228 mmol), 1,10-phenanthroline (82 mg, 0.456 mmol) and cesium carbonate (1.04 mg, 3.19 mmol). The vial was sealed under air atmosphere and heated to 110° C. for 24 h. The reaction mixture was cooled to rt and diethyl ether was added. The suspension was filtered through a pad of silica gel. The solvent was removed under reduced pressure and the remaining residue was purified by flash chromatography (100% hexanes). 2-Bromo-1-methyl-3-(neopentyloxy)benzene was obtained as a colorless oil.

Step 2:

The titled compound was obtained by a procedure similar to that described in Example 40, Step 2, but using 2-bromo-1-methyl-3-(neopentyloxy)benzene. The titled compound was obtained as a light-yellow solid. MS (ESI, pos. ion) m/z: 406 (M+1).

Example 53

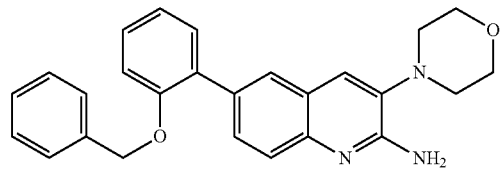 [SMILES: Nc1nc2ccc(-c3ccccc3OCc3ccccc3)cc2cc1N1CCOCC1]

Synthesis of 6-(2-(benzyloxy)phenyl)-3-morpholinoquinolin-2-amine

Step 1:

A vial was charged with 1-bromo-2-iodobenzene (0.642 mL, 5 mmol), phenylmethanol (1.036 mL, 10.00 mmol), copper(I) iodide (95 mg, 0.500 mmol), 1,10-phenanthroline (180 mg, 1.000 mmol), cesium carbonate (2281 mg, 7.00 mmol) and toluene (2.5 mL). The vial was sealed under air atmosphere and heated to 110° C. for 36 h. The reaction mixture was cooled to RT and diethyl ether was added. The suspension was filtered through a pad of silica gel. The solvent was removed under reduced pressure and the remaining residue was purified by flash chromatography (13% EtOAc/hexanes). 1-(Benzyloxy)-2-bromobenzene was obtained as a yellow oil.

Step 2:

The titled compound was obtained by a procedure similar to that described in Example 40, Step 2, but using 1-(benzyloxy)-2-bromobenzene. The titled compound was obtained as a light-yellow powder. MS (ESI, pos. ion) m/z: 412 (M+1).

Example 54

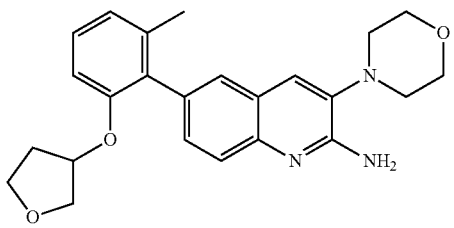 [SMILES: Cc1cccc(OC2CCOC2)c1-c1ccc2nc(N)c(N3CCOCC3)cc2c1]

Synthesis of 6-(2-methyl-6-(tetrahydrofuran-3-yloxy)phenyl)-3-morpholinoquinolin-2-amine Step 1:

A vial was charged with copper(I) iodide (38.5 mg, 0.202 mmol), 1,10-phenanthroline (72.8 mg, 0.404 mmol), cesium carbonate (1.32 g, 4.04 mmol), 2-bromo-1-iodo-3-methylbenzene (600 mg, 2.021 mmol) and tetrahydrofuran-3-ol (1.80 mL, 22.23 mmol). The vial was sealed and the reaction mixture was heated to 120° C. for 24 h. The reaction mixture was cooled to RT, EtOAc was added and the mixture was filtered through a pad of silica gel. The solvent was removed under reduced pressure and the remaining residue was purified by flash chromatography (25% EtOAc/hexanes). 3-(2-Bromo-3-methylphenoxy)tetrahydrofuran was isolated as a light-yellow oil (178 mg).

Step 2:

The titled compound was obtained by a procedure similar to that described in Example 40, Step 2 using 3-(2-bromo-3-methylphenoxy)tetrahydrofuran. The titled compound was obtained as a light-brown powder. MS (ESI, pos. ion) m/z: 406 (M+1).

Example 55

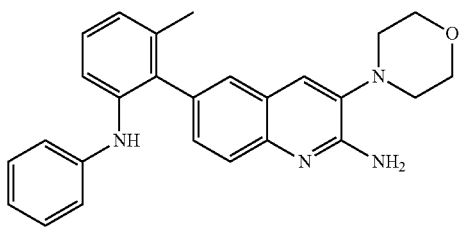 [SMILES: Cc1cccc(Nc2ccccc2)c1-c1ccc2nc(N)c(N3CCOCC3)cc2c1]

Synthesis of 6-(2-methyl-6-(phenylamino)phenyl)-3-morpholinoquinolin-2-amine

Step 1:

A vial was charged with Pd(OAc)$_2$ (22.56 mg, 0.101 mmol), 9,9-dimethyl-4,5-bis(diphenylphosphino)xanthene (83 mg, 0.144 mmol) and cesium carbonate (1124 mg, 3.45 mmol). The vial was evacuated and backfilled with nitrogen. This procedure was repeated three times. 2-Bromo-3-methylaniline (0.50 mL, 4.02 mmol), iodobenzene (0.37 mL, 3.35 mmol) and dioxane (10 mL) were added. The reaction mixture was allowed to stir at 110° C. overnight. The reaction mixture was cooled to room temperature and partitioned between water and EtOAc. The organic phase was separated and dried over MgSO$_4$. The remaining residue was purified by flash chromatography (5-15% EtOAc/hexanes). 2-Bromo-3-methyl-N-phenylaniline was obtained as a light-yellow, clear oil.

Step 2:

Following the procedure in Example 40, Step 2 using 2-bromo-3-methyl-N-phenylaniline, the titled compound was obtained as a yellow powder. MS (ESI, pos. ion) m/z: 411 (M+1).

Example 56

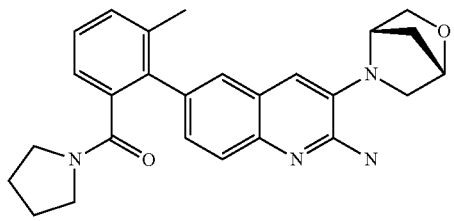 [SMILES: Cc1cccc(C(=O)N2CCCC2)c1-c1ccc2nc(N)c(N3C[C@@H]4C[C@H]3CO4)cc2c1]

Synthesis of (2-(2-amino-3-((1S,4S)-2-oxa-5-azabicyclo[2.2.1]heptan-5-yl)quinolin-6-yl)-3-methylphenyl)(pyrrolidin-1-yl)methanone Step 1:

Bromoacetonitrile (0.208 mL, 3.12 mmol) was added to a slurry of (1S,4S)-2-oxa-5-azabicyclo[2.2.1]heptane hydrochloride (0.353 g, 2.60 mmol), DMSO (13 mL) and MP-carbonate (3.17 mmol/g, 2.5×, 6.5 mmol, 2.05 g). After shaking overnight, 0.52 mmol trisamine (4.17 mmol/g, 125 mg) was added, and the slurry was shaken for an additional 2 h. The slurry was filtered and the resulting 2-((1S,4S)-2-oxa-5-azabicyclo[2.2.1]heptan-5-yl)acetonitrile/DMSO solution was used directly in the next step.

Step 2:

A mixture of methyl 2-amino-5-bromobenzoate (5.0 g, 21.7 mmol), 4,4,4',4',5,5,5',5'-octamethyl-2,2'-bi(1,3,2-dioxaborolane) (6.6 g, 26.1 mmol), dichloro 1,1'-bis(diphenylphosphino)ferrocene palladium (II) (0.89 g, 1.1 mmol), and potassium acetate (6.4 g, 65.2 mmol) under an inert atmosphere in a 500 mL RBF was treated with dioxane (130 mL). The suspension was heated to 85° C. for 18 h. The reaction mixture was concentrated in vacuo then diluted with EtOAc. The organic layer was washed with water and brine then dried over MgSO$_4$ and concentrated in vacuo to give a sticky tan solid which was used in the next step without further purification.

Step 3:

A mixture of 2-dicyclohexylphosphino-2',4',6'-triisopropylbiphenyl (0.172 g, 0.361 mmol), (2-bromo-3-methylphenyl)(pyrrolidin-1-yl)methanone (0.58 g, 2.2 mmol), methyl 2-amino-5-(4,4,5,5-tetramethyl-1,3,2-dioxaborolan-2-yl)benzoate (0.5 g, 1.8 mmol), Pd$_2$(dba)$_3$ (0.083 g, 0.090 mmol), anhydrous K$_3$PO$_4$ (0.448 mL, 5.41 mmol), and 1,4-dioxane (9 mL)/water (4.5 mL) was heated in a microwave unit at 140° C. for 12 min. The reaction mixture was filtered then concentrated in vacuo. The crude product was purified by silica flash chromatography (0-10% MeOH/DCM) to give the desired product as a yellow foam.

Step 4:

To a solution of methyl 4-amino-2'-methyl-6'-(pyrrolidine-1-carbonyl)biphenyl-3-carboxylate (164 mg, 0.49 mmol) and DCM (5 mL) cooled to −78° C. under $N_2$ was added a 1M solution of diisobutylaluminum hydride (2.5 mL, 2.5 mmol) in heptane. After 30 min the reaction mixture was quenched with water then allowed to warm to RT under $N_2$. The reaction mixture was diluted with DCM and washed with water. AcOH was added and the layers were separated. The organic layer was washed with water and brine then dried over $MgSO_4$ and concentrated in vacuo. The product was diluted with EtOAc and washed with 2M $Na_2CO_3$ (1×) then brine (1×) and concentrated in vacuo to give a yellow foam which was used as crude material in the next step.

Step 5:

To a solution of (4'-amino-3'-(hydroxymethyl)-6-methylbiphenyl-2-yl)(pyrrolidin-1-yl)methanone (150 mg, 0.48 mmol) and DCM (5 ml) was added manganese dioxide (210 mg, 2.4 mmol) and the reaction was stirred at RT. After 15 min, an additional amount of manganese dioxide (210 mg, 2.416 mmol) was added. After 5 min, the reaction mixture was filtered through celite then concentrated in vacuo to give the desired product as a yellow oil.

Step 6:

A solution of 4-amino-2'-methyl-6'-(pyrrolidine-1-carbonyl)biphenyl-3-carbaldehyde (0.100 g, 0.324 mmol) in DMSO (3.0 mL) was added to an 80° C. solution of 2-((1S,4S)-2-oxa-5-azabicyclo[2.2.1]heptan-5-yl)acetonitrile (0.067 g, 0.486 mmol) and potassium hydroxide (0.016 g, 0.28 mmol) (11 M aq., 44 uL) in DMSO (1.25 mL) in 4 portions at 15 min intervals. The resulting mixture was heated for 18 h, cooled, filtered and purified by prep HPLC (12-51% $CH_3CN$/water, 0.1% TFA) to give (2-(2-amino-3-((1S,4S)-2-oxa-5-azabicyclo[2.2.1]heptan-5-yl)quinolin-6-yl)-3-methylphenyl)(pyrrolidin-1-yl)methanone as a yellow solid. MS (ESI, pos. ion) m/z: 429 (M+1).

Example 57

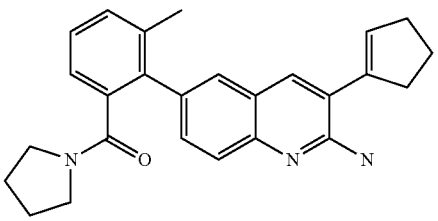 [SMILES: Cc1cccc(C(=O)N2CCCC2)c1-c1ccc2nc(N)c(C3=CCCC3)cc2c1]

Synthesis of (2-(2-amino-3-cyclopentenylquinolin-6-yl)-3-methylphenyl)(pyrrolidin-1-yl)methanone A solution of 4-amino-2'-methyl-6'-(pyrrolidine-1-carbonyl)biphenyl-3-carbaldehyde (0.040 g, 0.13 mmol, prepared as in Example 57, Steps 2-5), KOH (10.9 mg, 0.195 mmol) (11 M solution, 18 uL), 1-cyclopenteneacetonitrile (0.022 mL, 0.20 mmol) and DMSO (0.8 mL) was heated in a Biotage microwave at 140° C. for 5 min. LCMS indicated good conversion to desired product. The crude material was purified by prep HPLC (21-60% $CH_3CN$/water modified with 0.1% TFA), and again by prep HPLC (10-90% $CH_3CN$/water modified with 0.1% $NH_4OH$) to give (2-(2-amino-3-cyclopentenylquinolin-6-yl)-3-methylphenyl)(pyrrolidin-1-yl)methanone as a yellow solid. MS (ESI, pos. ion) m/z: 398 (M+1).

The following examples in Table I were prepared by methods analogous to those described in Examples 1-57 above. Provided also is the mass spectral data and BACE enzyme and cell-based assay data ($IC_{50}$'s in uM ranges) for each example, where available.

TABLE 1

| Ex. No. | Compound Name | Observed MS | BACE1 FRET assay (uM) | HEK cell assay (uM) |
|---|---|---|---|---|
| 1 | (2-(2-amino-3-morpholinoquinolin-6-yl)-3-methylphenyl)(pyrrolidin-1-yl)methanone | 417 | +++++ | ++++ |
| 58 | (2-(2-amino-3-morpholinoquinolin-6-yl)-3-methylphenyl)(piperidin-1-yl)methanone | 431 | +++++ | +++ |
| 59 | (2-(2-amino-3-morpholinoquinolin-6-yl)-3-methylphenyl)(morpholino)methanone | 433 | ++++ | ++ |
| 60 | (2-(2-amino-3-(pyrrolidin-1-yl)quinolin-6-yl)-3-methylphenyl)(pyrrolidin-1-yl)methanone | 401 | ++++ | ++ |
| 61 | (2-(2-amino-3-(piperidin-1-yl)quinolin-6-yl)-3-methylphenyl)(pyrrolidin-1-yl)methanone | 415 | +++ | ++ |
| 62 | ethyl 2-(2-amino-3-morpholinoquinolin-6-yl)-3-methylbenzoate | 392 | ++++ | ++ |
| 63 | (2-(2-amino-3-morpholinoquinolin-6-yl)-3-methylphenyl)(2-propylpyrrolidin-1-yl)methanone | 459 | ++++ | ++ |
| 64 | (2-(2-amino-3-morpholinoquinolin-6-yl)-3-methylphenyl)(2-tert-butylpyrrolidin-1-yl)methanone | 473 | +++++ | +++ |
| 65 | (2-(2-amino-3-morpholinoquinolin-6-yl)-3-methylphenyl)(2-ethylpyrrolidin-1-yl)methanone | 445 | +++++ | +++ |
| 66 | (2-(2-amino-3-morpholinoquinolin-6-yl)-3-methylphenyl)(2-isopropylpyrrolidin-1-yl)methanone | 459 | +++++ | ++++ |

TABLE 1-continued

| Ex. No. | Compound Name | Observed MS | BACE1 FRET assay (uM) | HEK cell assay (uM) |
|---|---|---|---|---|
| 67 | (2-(2-amino-3-morpholinoquinolin-6-yl)-3-methylphenyl)(2-methylpyrrolidin-1-yl)methanone | 431 | +++++ | ++++ |
| 68 | (2-(2-amino-3-morpholinoquinolin-6-yl)-3-methylphenyl)((1R,4S)-2-azabicyclo[2.2.1]heptan-2-yl)methanone | 443 | +++++ | ++++ |
| 69 | (R)-(2-(2-amino-3-morpholinoquinolin-6-yl)-3-methylphenyl)(3-fluoropyrrolidin-1-yl)methanone | 435 | +++++ | ++++ |
| 70 | (R)-(2-(2-amino-3-morpholinoquinolin-6-yl)-3-methylphenyl)(2-(methoxymethyl)pyrrolidin-1-yl)methanone | 461 | ++++ | ++ |
| 71 | 2-(2-amino-3-morpholinoquinolin-6-yl)-N-(2-methoxyethyl)-N,3-dimethylbenzamide | 435 | ++++ | ++ |
| 72 | (2-(2-amino-3-morpholinoquinolin-6-yl)-3-methylphenyl)(4-methoxypiperidin-1-yl)methanone | 461 | +++++ | ++ |
| 73 | (2-(2-amino-3-morpholinoquinolin-6-yl)-3-methylphenyl)(4-(methoxymethyl)piperidin-1-yl)methanone | 475 | ++++ | ++ |
| 74 | (2-(2-amino-3-morpholinoquinolin-6-yl)-3-methylphenyl)(4-(ethoxymethyl)piperidin-1-yl)methanone | 489 | +++++ | ++ |
| 75 | (2-(2-amino-3-morpholinoquinolin-6-yl)-3-methylphenyl)(4-(2-methoxyethyl)piperidin-1-yl)methanone | 489 | ++++ | ++ |
| 76 | (2-(2-amino-3-morpholinoquinolin-6-yl)-3-methylphenyl)(4-ethoxypiperidin-1-yl)methanone | 475 | +++++ | ++ |
| 77 | (R)-(2-(2-amino-3-morpholinoquinolin-6-yl)-3-methylphenyl)(3-methylpiperidin-1-yl)methanone | 445 | +++++ | ++ |
| 78 | (2-(2-amino-3-morpholinoquinolin-6-yl)-3-methylphenyl)(4-propylpiperidin-1-yl)methanone | 473 | +++++ | + |
| 79 | (2-(2-amino-3-morpholinoquinolin-6-yl)-3-methylphenyl)(2-propylpiperidin-1-yl)methanone | 473 | ++++ | ++ |
| 80 | (2-(2-amino-3-morpholinoquinolin-6-yl)-3-methylphenyl)(4-methylpiperidin-1-yl)methanone | 445 | +++++ | ++ |
| 81 | (2-(2-amino-3-morpholinoquinolin-6-yl)-3-methylphenyl)(2-ethylpiperidin-1-yl)methanone | 459 | +++++ | ++ |
| 82 | (2-(2-amino-3-morpholinoquinolin-6-yl)-3-methylphenyl)(3-methoxypiperidin-1-yl)methanone | 461 | ++++ | ++ |
| 83 | (2-(2-amino-3-morpholinoquinolin-6-yl)-3-methylphenyl)(2-(2-methoxyethyl)piperidin-1-yl)methanone | 489 | ++++ | ++ |
| 84 | (2-(2-amino-3-morpholinoquinolin-6-yl)-3-methylphenyl)((2S,6R)-2,6-dimethylpiperidin-1-yl)methanone | 459 | +++++ | +++ |
| 85 | (2-(2-amino-3-morpholinoquinolin-6-yl)-3-methylphenyl)(3-ethoxypiperidin-1-yl)methanone | 475 | ++++ | ++ |
| 86 | (2-(2-amino-3-morpholinoquinolin-6-yl)-3-methylphenyl)(3,3-dimethylpiperidin-1-yl)methanone | 459 | +++++ | ++++ |
| 87 | (2-(2-amino-3-morpholinoquinolin-6-yl)-3-methylphenyl)(2-methylpiperidin-1-yl)methanone | 445 | +++++ | +++ |
| 88 | (2-(2-amino-3-morpholinoquinolin-6-yl)-3-methylphenyl)(3,5-dimethylpiperidin-1-yl)methanone | 459 | ++++ | ++ |
| 89 | (2-(2-amino-3-morpholinoquinolin-6-yl)-3-methylphenyl)(thiazolidin-3-yl)methanone | 435 | +++++ | +++ |
| 90 | (2-(2-amino-3-morpholinoquinolin-6-yl)-3-methylphenyl)(2,5-dihydro-1H-pyrrol-1-yl)methanone | 415 | +++++ | +++ |
| 91 | (2-(2-amino-3-morpholinoquinolin-6-yl)-3-methylphenyl)(thiomorpholino)methanone | 449 | +++++ | ++ |
| 92 | 2-(2-amino-3-morpholinoquinolin-6-yl)-N-cyclopentyl-N,3-dimethylbenzamide | 445 | +++++ | +++ |

TABLE 1-continued

| Ex. No. | Compound Name | Observed MS | BACE1 FRET assay (uM) | HEK cell assay (uM) |
|---|---|---|---|---|
| 93 | (2-(2-amino-3-morpholinoquinolin-6-yl)-3-methylphenyl)(4-tert-butylpiperidin-1-yl)methanone | 487 | +++++ | +++ |
| 94 | (S)-(2-(2-amino-3-morpholinoquinolin-6-yl)-3-methylphenyl)(2-(trifluoromethyl)pyrrolidin-1-yl)methanone | 485 | ++++ | ++ |
| 95 | (2-(2-amino-3-morpholinoquinolin-6-yl)-3-methylphenyl)(4-fluoropiperidin-1-yl)methanone | 449 | +++++ | ++ |
| 96 | (2-(2-amino-3-morpholinoquinolin-6-yl)-3-methylphenyl)(3-(trifluoromethyl)pyrrolidin-1-yl)methanone | 485 | +++++ | ++ |
| 97 | (2-(2-amino-3-morpholinoquinolin-6-yl)-3-methylphenyl)(3,3-difluoropiperidin-1-yl)methanone | 467 | +++++ | +++ |
| 98 | (2-(2-amino-3-morpholinoquinolin-6-yl)-3-methylphenyl)(3,3-difluoropyrrolidin-1-yl)methanone | 453 | +++++ | ++++ |
| 99 | (2-(2-amino-3-morpholinoquinolin-6-yl)-3-methylphenyl)(3,3-difluoroazetidin-1-yl)methanone | 439 | ++++ | +++ |
| 100 | 2-(2-amino-3-morpholinoquinolin-6-yl)-N,3-dimethyl-N-(2,2,2-trifluoroethyl)benzamide | 459 | ++++ | ++ |
| 101 | (R)-(2-(2-amino-3-morpholinoquinolin-6-yl)-3-methylphenyl)(3-methylpyrrolidin-1-yl)methanone | 431 | +++++ | +++ |
| 102 | 2-(2-amino-3-morpholinoquinolin-6-yl)-N,N-diethyl-3-methylbenzamide | 419 | ++++ | ++ |
| 103 | (2-(2-amino-3-morpholinoquinolin-6-yl)-3-methylphenyl)(azetidin-1-yl)methanone | 403 | ++++ | +++ |
| 104 | 2-(2-amino-3-morpholinoquinolin-6-yl)-N-isobutyl-N,3-dimethylbenzamide | 433 | +++++ | +++ |
| 105 | 2-(2-amino-3-morpholinoquinolin-6-yl)-N-ethyl-3-methyl-N-propylbenzamide | 433 | +++ | ++ |
| 106 | 2-(2-amino-3-morpholinoquinolin-6-yl)-N-isopropyl-3-methyl-N-propylbenzamide | 447 | +++ | + |
| 107 | 2-(2-amino-3-morpholinoquinolin-6-yl)-N-cyclopropyl-N-ethyl-3-methylbenzamide | 431 | ++++ | ++ |
| 108 | 2-(2-amino-3-morpholinoquinolin-6-yl)-N,3-dimethyl-N-(prop-2-ynyl)benzamide | 415 | +++++ | +++ |
| 109 | (2-(2-amino-3-morpholinoquinolin-6-yl)-3-methylphenyl)(4,4-difluoropiperidin-1-yl)methanone | 467 | +++++ | +++ |
| 110 | 2-(2-amino-3-morpholinoquinolin-6-yl)-N,3-dimethyl-N-propylbenzamide | 419 | ++++ | ++ |
| 111 | 2-(2-amino-3-morpholinoquinolin-6-yl)-N-(cyclopropylmethyl)-3-methyl-N-propylbenzamide | 459 | 1.542 | + |
| 112 | 2-(2-amino-3-morpholinoquinolin-6-yl)-N-cyclohexyl-N,3-dimethylbenzamide | 459 | +++++ | ++ |
| 113 | 2-(2-amino-3-morpholinoquinolin-6-yl)-N-cyclohexyl-N-ethyl-3-methylbenzamide | 473 | ++++ | ++ |
| 114 | (2-(2-amino-3-morpholinoquinolin-6-yl)-3-methylphenyl)(2-(methylthio)-4,5-dihydro-1H-imidazol-1-yl)methanone | 462 | 1.139 | + |
| 115 | (2-(2-amino-3-morpholinoquinolin-6-yl)-3-methylphenyl)(3-methylpiperidin-1-yl)methanone | 445 | +++++ | +++ |
| 116 | N,N-diallyl-2-(2-amino-3-morpholinoquinolin-6-yl)-3-methylbenzamide | 443 | ++++ | ++ |
| 117 | 2-(2-amino-3-morpholinoquinolin-6-yl)-N-butyl-N,3-dimethylbenzamide | 433 | +++++ | ++ |
| 118 | 2-(2-amino-3-morpholinoquinolin-6-yl)-N-butyl-N-ethyl-3-methylbenzamide | 447 | +++ | ++ |
| 119 | 2-(2-amino-3-morpholinoquinolin-6-yl)-N-isopentyl-N,3-dimethylbenzamide | 447 | ++++ | ++ |
| 120 | 2-(2-amino-3-morpholinoquinolin-6-yl)-N,3-dimethyl-N-(pentan-2-yl)benzamide | 447 | +++++ | ++ |
| 121 | 2-(2-amino-3-morpholinoquinolin-6-yl)-N-ethyl-N,3-dimethylbenzamide | 405 | ++++ | ++ |
| 122 | 2-(2-amino-3-morpholinoquinolin-6-yl)-N,3-dimethyl-N-(4-methylcyclohexyl)benzamide | 473 | +++++ | +++ |
| 123 | 2-(2-amino-3-morpholinoquinolin-6-yl)-N-tert-butyl-N,3-dimethylbenzamide | 433 | +++++ | +++ |

TABLE 1-continued

| Ex. No. | Compound Name | Observed MS | BACE1 FRET assay (uM) | HEK cell assay (uM) |
|---|---|---|---|---|
| 124 | (2-(2-amino-3-morpholinoquinolin-6-yl)-3-methylphenyl)(2,6-dimethylpiperidin-1-yl)methanone | 459 | +++++ | ++ |
| 125 | (2-(2-amino-3-morpholinoquinolin-6-yl)-3-methylphenyl)(2,5-dimethyl-2,5-dihydro-1H-pyrrol-1-yl)methanone | 443 | +++++ | +++ |
| 126 | 2-(2-amino-3-morpholinoquinolin-6-yl)-N,3-dimethyl-N-phenylbenzamide | 453 | ++++ | ++ |
| 127 | 2-(2-amino-3-morpholinoquinolin-6-yl)-3-methyl-N-phenylbenzamide | 439 | ++ | + |
| 128 | (2-(2-amino-3-morpholinoquinolin-6-yl)-5-fluorophenyl)(azetidin-1-yl)methanone | 407 | ++ | + |
| 129 | ethyl 2-(2-amino-3-morpholinoquinolin-6-yl)-5-fluoro-3-methylbenzoate | 410 | ++++ | ++ |
| 130 | (R)-(2-(2-amino-3-morpholinoquinolin-6-yl)-5-fluoro-3-methylphenyl)(3-fluoropyrrolidin-1-yl)methanone | 453 | +++++ | ++++ |
| 131 | 2-(2-amino-3-morpholinoquinolin-6-yl)-N,3-dimethyl-N-p-tolylbenzamide | 467 | +++++ | ++ |
| 132 | 2-(2-amino-3-morpholinoquinolin-6-yl)-N-(4-methoxyphenyl)-N,3-dimethylbenzamide | 483 | +++++ | +++ |
| 133 | (R)-2-(2-amino-3-morpholinoquinolin-6-yl)-N,3-dimethyl-N-(1-phenylethyl)benzamide | 481 | +++++ | ++ |
| 134 | 2-(2-amino-3-morpholinoquinolin-6-yl)-N,N,3-trimethylbenzamide | 391 | ++++ | ++ |
| 135 | 2-(2-amino-3-morpholinoquinolin-6-yl)-N,3-dimethyl-N-(naphthalen-1-ylmethyl)benzamide | 517 | ++++ | ++ |
| 136 | 2-(2-amino-3-morpholinoquinolin-6-yl)-N-benzyl-N,3-dimethylbenzamide | 467 | ++++ | ++ |
| 137 | 2-(2-amino-3-morpholinoquinolin-6-yl)-N,3-dimethyl-N-phenethylbenzamide | 481 | ++++ | ++ |
| 138 | 2-(2-amino-3-morpholinoquinolin-6-yl)-N-(4-fluorophenyl)-N,3-dimethylbenzamide | 471 | ++++ | ++ |
| 139 | 2-(2-amino-3-morpholinoquinolin-6-yl)-N-(2-methoxyphenyl)-N,3-dimethylbenzamide | 483 | +++++ | ++ |
| 140 | (2-(2-amino-7-fluoro-3-morpholinoquinolin-6-yl)phenyl)(pyrrolidin-1-yl)methanone | 421 | ++++ | ++ |
| 141 | (2-(2-amino-3-morpholinoquinolin-6-yl)-6-chlorophenyl)(pyrrolidin-1-yl)methanone | 437 | ++ | + |
| 142 | (2-(2-amino-3-morpholinoquinolin-6-yl)-6-fluorophenyl)(pyrrolidin-1-yl)methanone | 421 | ++ | + |
| 143 | (2-(2-amino-3-morpholinoquinolin-6-yl)-3-chlorophenyl)(piperidin-1-yl)methanone | 451 | +++++ | ++ |
| 144 | (2-(2-amino-3-morpholinoquinolin-6-yl)-3-chlorophenyl)(morpholino)methanone | 453 | ++++ | ++ |
| 145 | cyclopentyl 2-(2-amino-3-morpholinoquinolin-6-yl)benzoate | 418 | +++++ | +++ |
| 19 | cyclopentyl 2-(2-amino-3-morpholinoquinolin-6-yl)-3-methylbenzoate | 432 | +++++ | ++++ |
| 11 | (2-(2-amino-3-morpholinoquinolin-6-yl)phenyl)(tetrahydro-2H-pyran-4-yl)methanone | 418 | ++++ | ++ |
| 12 | (2-(2-amino-3-morpholinoquinolin-6-yl)phenyl)(tetrahydro-2H-pyran-4-yl)methanol | 420 | ++ | + |
| 13 | 3-morpholino-6-(2-((tetrahydro-2H-pyran-4-yl)methyl)phenyl)quinolin-2-amine | 404 | ++++ | ++ |
| 39 | (2-(2-amino-7-fluoro-3-morpholinoquinolin-6-yl)-3-methylphenyl)(pyrrolidin-1-yl)methanone | 435 | +++++ | +++ |
| 146 | (2-(2-amino-3-morpholinoquinolin-6-yl)phenyl)(pyrrolidin-1-yl)methanone | 403 | ++++ | ++ |
| 147 | (2-(2-amino-3-morpholinoquinolin-6-yl)-5-chlorophenyl)(pyrrolidin-1-yl)methanone | 437 | ++++ | ++ |
| 148 | (2-(2-amino-3-morpholinoquinolin-6-yl)-3-fluorophenyl)(pyrrolidin-1-yl)methanone | 421 | ++++ | ++ |
| 149 | (2-(2-amino-3-morpholinoquinolin-6-yl)phenyl)(cyclopentyl)methanone | 402 | ++++ | + |
| 150 | (2-(2-amino-3-morpholinoquinolin-6-yl)-4-methylphenyl)(pyrrolidin-1-yl)methanone | 417 | +++++ | ++++ |
| 151 | (2-(2-amino-3-morpholinoquinolin-6-yl)phenyl)(phenyl)methanone | 410 | ++++ | ++ |
| 152 | (2-(2-amino-3-morpholinoquinolin-6-yl)phenyl)(cyclohexyl)methanone | 416 | +++++ | ++ |
| 153 | 1-(2-(2-amino-3-morpholinoquinolin-6-yl)phenyl)-3,3-dimethylbutan-1-one | 404 | ++++ | + |

TABLE 1-continued

| Ex. No. | Compound Name | Observed MS | BACE1 FRET assay (uM) | HEK cell assay (uM) |
|---|---|---|---|---|
| 154 | (2-(2-amino-3-morpholinoquinolin-6-yl)-4-chlorophenyl)(pyrrolidin-1-yl)methanone | 437 | +++++ | +++ |
| 155 | (2-(2-amino-3-morpholinoquinolin-6-yl)-3-(trifluoromethyl)phenyl)(pyrrolidin-1-yl)methanone | 471 | ++++ | ++ |
| 156 | 1-(2-(2-amino-3-morpholinoquinolin-6-yl)phenyl)-2-cyclopentylethanone | 416 | +++++ | ++ |
| 3 | (2-(2-amino-3-morpholinoquinolin-6-yl)-3-methylphenyl)(o-tolyl)methanone | 438 | +++++ | +++ |
| 2 | (2-(2-amino-3-morpholinoquinolin-6-yl)-3-methylphenyl)(phenyl)methanone | 424 | +++++ | ++ |
| 157 | (2-(2-amino-3-morpholinoquinolin-6-yl)-3-methylphenyl)(pyridin-2-yl)methanone | 425 | +++++ | +++ |
| 158 | (2-(2-amino-3-morpholinoquinolin-6-yl)-3-methylphenyl)(thiazol-2-yl)methanone | 431 | ++++ | ++ |
| 7 | (2-(2-amino-3-morpholinoquinolin-6-yl)-3-methylphenyl)(2-methoxyphenyl)methanone | 454 | +++++ | ++++ |
| 159 | (2-(2-amino-3-morpholinoquinolin-6-yl)-3-methylphenyl)(3-chloropyridin-2-yl)methanone | 459 | +++++ | +++ |
| 4 | 6-(2-(3,4-dihydroisoquinolin-1-yl)-6-methylphenyl)-3-morpholinoquinolin-2-amine | 449 | ++++ | +++ |
| 5 | (2-(2-amino-3-morpholinoquinolin-6-yl)-3-methylphenyl)(tetrahydrofuran-2-yl)methanone | 418 | ++++ | +++ |
| 6 | 6-(2-(imino(2-methoxyphenyl)methyl)-6-methylphenyl)-3-morpholinoquinolin-2-amine | 453 | +++++ | +++++ |
| 8 | 6-(2-((1H-imidazol-1-yl)(phenyl)methyl)-6-methylphenyl)-3-morpholinoquinolin-2-amine | 476 | ++ | ++ |
| 9 | 6-(2-methyl-6-(phenyl(pyrrolidin-1-yl)methyl)phenyl)-3-morpholinoquinolin-2-amine | 479 | +++ | ++++ |
| 10 | 6-(2-methyl-6-(1,2,3,4-tetrahydroisoquinolin-1-yl)phenyl)-3-morpholinoquinolin-2-amine | 451 | ++ | ++++ |
| 40 | 6-(2-(3,3-dimethylbut-1-ynyl)-6-methylphenyl)-3-morpholinoquinolin-2-amine | 400 | +++++ | ++ |
| 41 | 2-(2-amino-3-morpholinoquinolin-6-yl)-N,3-dimethyl-N-neopentylbenzamide | 447 | +++++ | +++ |
| 160 | 6-(2-(3,3-dimethylbut-1-ynyl)phenyl)-3-morpholinoquinolin-2-amine | 386 | +++ | + |
| 42 | (2-(2-amino-3-morpholinoquinolin-6-yl)-3-chlorophenyl)(pyrrolidin-1-yl)methanone | 437 | +++++ | +++ |
| 43 | (2-(2-amino-3-morpholinoquinolin-6-yl)-3-methylphenyl)(2,2-dimethylmorpholino)methanone | 461 | ++++ | ++ |
| 44 | (2-(2-amino-3-morpholinoquinolin-6-yl)-3-(3,3-dimethylbut-1-ynyl)phenyl)(pyrrolidin-1-yl)methanone | 483 | +++++ | ++++ |
| 45 | (2-(2-amino-3-morpholinoquinolin-6-yl)-3-(3,3-dimethylbutyl)phenyl)(pyrrolidin-1-yl)methanone | 487 | +++++ | +++++ |
| 46 | 1-(2-(2-amino-3-morpholinoquinolin-6-yl)-3-(pyrrolidine-1-carbonyl)phenyl)-3,3-dimethylbutan-1-one | 501 | +++++ | ++++ |
| 161 | (2-(2-amino-3-morpholinoquinolin-6-yl)-3-(phenylethynyl)phenyl)(pyrrolidin-1-yl)methanone | 502 (M) | +++++ | +++ |
| 162 | (2-(2-amino-3-morpholinoquinolin-6-yl)-3-phenethylphenyl)(pyrrolidin-1-yl)methanone | 507 | +++++ | +++++ |
| 47 | (S)-(2-(2-amino-3-morpholinoquinolin-6-yl)-3-(3,3-dimethylbutyl)phenyl)(3-fluoropyrrolidin-1-yl)methanone | 505 | +++++ | +++++ |
| 163 | (2-(2-amino-3-morpholinoquinolin-6-yl)-3-(3,3-dimethylbutyl)phenyl)(morpholino)methanone | 503 | +++++ | +++++ |
| 164 | (2-(2-amino-3-morpholinoquinolin-6-yl)-3-(3,3-dimethylbutyl)phenyl)(azetidin-1-yl)methanone | 473 | +++++ | +++++ |
| 165 | (2-(2-amino-3-((1S,4S)-2-oxa-5-azabicyclo[2.2.1]heptan-5-yl)quinolin-6-yl)-3-(3,3-dimethylbutyl)phenyl)(pyrrolidin-1-yl)methanone | 499 | +++++ | +++++ |
| 166 | (S)-(2-(2-amino-3-morpholinoquinolin-6-yl)-3-(3,3-dimethylbutyl)phenyl)(3-fluoropyrrolidin-1-yl)methanone | 505 | +++++ | +++++ |
| 167 | (2-(2-amino-3-morpholinoquinolin-6-yl)-3-(cyclohexylethynyl)phenyl)(pyrrolidin-1-yl)methanone | 509 | +++++ | +++++ |

TABLE 1-continued

| Ex. No. | Compound Name | Observed MS | BACE1 FRET assay (uM) | HEK cell assay (uM) |
|---|---|---|---|---|
| 168 | (2-(2-amino-3-morpholinoquinolin-6-yl)-3-(2-cyclohexylethyl)phenyl)(pyrrolidin-1-yl)methanone | 513 | +++++ | +++++ |
| 48 | 4-(2-(2-amino-3-morpholinoquinolin-6-yl)-3-methylphenyl)morpholin-3-one | 419 | +++ | ++ |
| 50 | N-(2-(2-amino-3-morpholinoquinolin-6-yl)-3-methylphenyl)-N,3,3-trimethylbutanamide | 447 | +++ | ++ |
| 55 | 6-(2-methyl-6-(phenylamino)phenyl)-3-morpholinoquinolin-2-amine | 411 | ++++ | + |
| 49 | 4-(2-(2-amino-3-morpholinoquinolin-6-yl)-3-methylphenyl)-6,6-dimethylmorpholin-3-one | 447 | ++++ | ++ |
| 51 | 3-morpholino-6-(2-(neopentyloxy)phenyl)quinolin-2-amine | 392 | +++ | + |
| 52 | 6-(2-methyl-6-(neopentyloxy)phenyl)-3-morpholinoquinolin-2-amine | 406 | +++++ | + |
| 53 | 6-(2-(benzyloxy)phenyl)-3-morpholinoquinolin-2-amine | 412 | ++++ | + |
| 169 | 6-(2-(benzyloxy)-6-methylphenyl)-3-morpholinoquinolin-2-amine | 426 | +++++ | + |
| 54 | 6-(2-methyl-6-(tetrahydrofuran-3-yloxy)phenyl)-3-morpholinoquinolin-2-amine | 406 | +++ | ++__ |
| 170 | 6-(2-(2-isopropoxyethoxy)-6-methylphenyl)-3-morpholinoquinolin-2-amine | 422 | +++++ | ++ |
| 171 | 6-(2-methyl-6-phenoxyphenyl)-3-morpholinoquinolin-2-amine | 412 | +++++ | + |
| 172 | 6-(2-(3,3-dimethylbutyl)-6-methylphenyl)-3-morpholinoquinolin-2-amine | 404 | +++++ | ++ |
| 173 | (2-(2-amino-3-morpholinoquinolin-6-yl)-3-methylphenyl)(m-tolyl)methanone | 438.1 | +++++ | ++ |
| 174 | (2-(2-amino-3-morpholinoquinolin-6-yl)-3-methylphenyl)(3-chlorophenyl)methanone | 458.1 | +++++ | ++ |
| 175 | (2-(2-amino-3-morpholinoquinolin-6-yl)-3-methylphenyl)(4-methoxyphenyl)methanone | 454.1 | +++++ | ++ |
| 176 | (2-(2-amino-3-morpholinoquinolin-6-yl)-3-methylphenyl)(4-chlorophenyl)methanone | 458 | +++++ | ++ |
| 177 | (2-(2-amino-3-morpholinoquinolin-6-yl)-3-methylphenyl)(3-methoxyphenyl)methanone | 454.1 | ++++ | ++ |
| 178 | (2-(2-amino-3-morpholinoquinolin-6-yl)-3-methylphenyl)(p-tolyl)methanone | 438.1 | +++++ | ++ |
| 179 | 1-(2-(2-amino-3-morpholinoquinolin-6-yl)-3-methylphenyl)butan-1-one | 390.1 | ++++ | ++ |
| 14 | 6-(2-(1-iminobutyl)-6-methylphenyl)-3-morpholinoquinolin-2-amine | 389.2 | ++++ | + |
| 180 | 1-(2-(2-amino-3-morpholinoquinolin-6-yl)-3-methylphenyl)pentan-1-one | 404.2 | +++++ | ++ |
| 181 | (2-(2-amino-3-morpholinoquinolin-6-yl)-3-methylphenyl)(cyclohexyl)methanone | 430.1 | +++++ | ++ |
| 182 | 1-(2-(2-amino-3-morpholinoquinolin-6-yl)-3-methylphenyl)-3-methylbutan-1-one | 404.1 | +++++ | +++ |
| 183 | 1-(2-(2-amino-3-morpholinoquinolin-6-yl)-3-methylphenyl)but-2-en-1-one | 388.1 | ++++ | ++ |
| 184 | (2-(2-amino-3-morpholinoquinolin-6-yl)-3-methylphenyl)(cyclopentyl)methanone | 416.1 | +++++ | +++ |
| 185 | 1-(2-(2-amino-3-morpholinoquinolin-6-yl)-3-methylphenyl)-2-phenylethanone | 438 | +++++ | ++ |
| 186 | (2-(2-amino-3-morpholinoquinolin-6-yl)-3-methylphenyl)(cyclopropyl)methanone | 388.1 | ++++ | ++ |
| 187 | (2-(2-amino-3-morpholinoquinolin-6-yl)-3-methylphenyl)(3-methoxypyridin-2-yl)methanone | 455.1 | +++++ | ++++ |
| 188 | 3-((1S,4S)-2-oxa-5-azabicyclo[2.2.1]heptan-5-yl)-6-(2-(imino(2-methoxyphenyl)methyl)-6-methylphenyl)quinolin-2-amine | 465 | ++++ | +++ |
| 189 | (2-(2-amino-3-morpholinoquinolin-6-yl)-3-methylphenyl)(3-methylpyridin-2-yl)methanone | 439.1 | ++++ | +++ |
| 190 | (E)-(2-(2-amino-3-morpholinoquinolin-6-yl)-3-methylphenyl)(phenyl)methanone oxime | 439.1 | +++++ | ++++ |
| 16 | (Z)-(2-(2-amino-3-morpholinoquinolin-6-yl)-3-methylphenyl)(phenyl)methanone oxime | 439.1 | +++++ | +++ |
| 15 | (E)-(2-(2-amino-3-morpholinoquinolin-6-yl)-3-methylphenyl)(phenyl)methanone O-methyl oxime | 453 | +++++ | +++ |
| 191 | (Z)-(2-(2-amino-3-morpholinoquinolin-6-yl)-3-methylphenyl)(phenyl)methanone O-methyl oxime | 453.2 | +++++ | ++ |

TABLE 1-continued

| Ex. No. | Compound Name | Observed MS | BACE1 FRET assay (uM) | HEK cell assay (uM) |
|---|---|---|---|---|
| 192 | (3-((1,3-dioxolan-2-yl)methyl)-2-(2-amino-3-morpholinoquinolin-6-yl)phenyl)(pyrrolidin-1-yl)methanone | 489.2 | +++++ | ++++ |
| 17 | 6-(2-(amino(phenyl)methyl)-6-methylphenyl)-3-morpholinoquinolin-2-amine | 425.1 | +++++ | +++++ |
| 193 | 6-(2-(amino(o-tolyl)methyl)-6-methylphenyl)-3-morpholinoquinolin-2-amine | 439.1 | +++++ | +++++ |
| 194 | 6-(2-(amino(3-methylpyridin-2-yl)methyl)-6-methylphenyl)-3-morpholinoquinolin-2-amine | 440.1 | +++ | ++++ |
| 195 | 6-(2-(amino(2-methoxyphenyl)methyl)-6-methylphenyl)-3-morpholinoquinolin-2-amine | 455.1 | +++++ | +++++ |
| 196 | 6-(2-(amino(pyridin-2-yl)methyl)-6-methylphenyl)-3-morpholinoquinolin-2-amine | 426 | ++++ | ++++ |
| 197 | 6-(2-(amino(3-chloropyridin-2-yl)methyl)-6-methylphenyl)-3-morpholinoquinolin-2-amine | 460.1 | ++++ | ++++ |
| 198 | 6-(2-(amino(3-methoxypyridin-2-yl)methyl)-6-methylphenyl)-3-morpholinoquinolin-2-amine | 456 | ++++ | +++++ |
| 199 | (2-(2-amino-3-morpholinoquinolin-6-yl)-3-methylphenyl)(phenyl)methanol | 426 | +++++ | ++++ |
| 18 | 6-(2-benzyl-6-methylphenyl)-3-morpholinoquinolin-2-amine | 410.1 | +++++ | ++ |
| 200 | 3-(2-(2-amino-3-morpholinoquinolin-6-yl)-3-methylbenzyl)benzonitrile | 435 | +++++ | ++ |
| 201 | 6-(2-(4-fluorobenzyl)-6-methylphenyl)-3-morpholinoquinolin-2-amine | 428.1 | +++++ | ++ |
| 202 | 6-(2-(2-fluorobenzyl)-6-methylphenyl)-3-morpholinoquinolin-2-amine | 428.1 | +++++ | ++ |
| 203 | 6-(2-(3-methoxybenzyl)-6-methylphenyl)-3-morpholinoquinolin-2-amine | 440.1 | +++++ | + |
| 204 | 6-(2-(4-chloro-1H-pyrazol-1-yl)-6-methylphenyl)-3-morpholinoquinolin-2-amine | 420.2 | +++ | + |
| 34 | 6-(2-(4-chloro-3-methyl-1H-pyrazol-1-yl)-6-methylphenyl)-3-morpholinoquinolin-2-amine | 434 | +++++ | ++ |
| 33 | 3-morpholino-6-(2-(4,5,6,7-tetrahydro-1H-indazol-1-yl)phenyl)quinolin-2-amine | 426 | ++++ | ++ |
| 28 | (2-(2-amino-3-(tetrahydro-2H-pyran-4-yl)quinolin-6-yl)-3-methylphenyl)(pyrrolidin-1-yl)methanone | 416.1 | +++++ | +++++ |
| 32 | 6-(2-methyl-6-(5-methyloxazol-2-yl)phenyl)-3-morpholinoquinolin-2-amine | 401 | ++ | + |
| 31 | 6-(2-methyl-6-(4-methyloxazol-2-yl)phenyl)-3-morpholinoquinolin-2-amine | 401 | ++++ | + |
| 30 | 6-(2-(imidazo[1,5-a]pyridin-3-yl)-6-methylphenyl)-3-morpholinoquinolin-2-amine | 436 | ++++ | ++ |
| 205 | (2-(2-amino-3-(2,2-dimethyltetrahydro-2H-pyran-4-yl)quinolin-6-yl)-3-methylphenyl)(pyrrolidin-1-yl)methanone | 444.2 | +++++ | +++++ |
| 206 | (2-(2-amino-3-(oxepan-4-yl)quinolin-6-yl)-3-methylphenyl)(pyrrolidin-1-yl)methanone | 430.2 | +++++ | ++++ |
| 29 | (2-(2-amino-3-(tetrahydro-2H-pyran-2-yl)quinolin-6-yl)-3-methylphenyl)(pyrrolidin-1-yl)methanone | 416 | ++++ | ++ |
| 207 | (2-(2-amino-3-(tetrahydrofuran-2-yl)quinolin-6-yl)-3-methylphenyl)(pyrrolidin-1-yl)methanone | 402.1 | ++++ | ++ |
| 27 | (2-(2-amino-3-morpholinoquinolin-6-yl)-5-fluoro-3-methylphenyl)(pyrrolidin-1-yl)methanone | 435 | +++++ | ++++ |
| 26 | (2-(2-amino-3-morpholinoquinolin-6-yl)-3-methylphenyl)(1H-indol-1-yl)methanone | 463 | ++++ | + |
| 208 | 6-(2-((2-chloro-5-(trifluoromethyl)phenoxy)methyl)-6-methylphenyl)-3-morpholinoquinolin-2-amine | 528 | +++++ | ++++ |
| 25 | 6-(3-methyl-3'-(trifluoromethyl)biphenyl-2-yl)-3-morpholinoquinolin-2-amine | 464 | +++++ | + |
| 20 | (R)-(2-(2-amino-3-(3-methylmorpholino)quinolin-6-yl)-3-methylphenyl)(pyrrolidin-1-yl)methanone | 431 | +++++ | +++ |
| 209 | (2-(2-amino-3-(2,3-dimethylmorpholino)quinolin-6-yl)-3-methylphenyl)(pyrrolidin-1-yl)methanone | 445.1 | +++++ | +++ |
| 210 | (S)-(2-(2-amino-3-(3-methylmorpholino)quinolin-6-yl)-3-methylphenyl)(pyrrolidin-1-yl)methanone | 431.1 | +++ | ++ |

TABLE 1-continued

| Ex. No. | Compound Name | Observed MS | BACE1 FRET assay (uM) | HEK cell assay (uM) |
|---|---|---|---|---|
| 211 | (2-(2-amino-3-(tetrahydro-2H-pyran-4-yl)quinolin-6-yl)-3-methylphenyl)(3,3-difluoropyrrolidin-1-yl)methanone | 452 | +++++ | ++++ |
| 21 | (2-(2-amino-3-(2-ethylmorpholino)quinolin-6-yl)-3-methylphenyl)(pyrrolidin-1-yl)methanone | 445 | +++++ | ++ |
| 38 | (2-(2-amino-3-(tetrahydro-2H-pyran-4-yl)quinolin-6-yl)-3-methylphenyl)(pyridin-2-yl)methanone | 424 | +++++ | ++++ |
| 212 | (2-(2-amino-3-(tetrahydro-2H-pyran-4-yl)quinolin-6-yl)-3-methylphenyl)(2-methoxyphenyl)methanone | 453 | +++++ | +++++ |
| 22 | 6-(2-([1,2,4]triazolo[4,3-a]pyridin-3-yl)-6-methylphenyl)-3-morpholinoquinolin-2-amine | 437 | ++++ | +++ |
| 23 | (2-(2-amino-3-morpholinoquinolin-6-yl)-3-methylphenyl)(pyrimidin-4-yl)methanone | 426 | ++++ | + |
| 36 | (2-(2-amino-3-morpholinoquinolin-6-yl)-3-methylphenyl)(pyrazin-2-yl)methanol | 428 | ++ | ++ |
| 37 | 6-(2-methyl-6-(pyrazin-2-ylmethyl)phenyl)-3-morpholinoquinolin-2-amine | 412 | +++ | ++ |
| 56 | (2-(2-amino-3-((1S,4S)-2-oxa-5-azabicyclo[2.2.1]heptan-5-yl)quinolin-6-yl)-3-methylphenyl)(pyrrolidin-1-yl)methanone | 429 | +++++ | +++++ |
| 213 | (2-(2-amino-3-(2-isobutylmorpholino)quinolin-6-yl)-3-methylphenyl)(pyrrolidin-1-yl)methanone | 473 | +++++ | ++ |
| 214 | (2-(2-amino-3-(2-(2-methoxyethyl)morpholino)quinolin-6-yl)-3-methylphenyl)(pyrrolidin-1-yl)methanone | 475 | +++++ | ++++ |
| 215 | (2-(2-amino-3-(2,2-dimethylmorpholino)quinolin-6-yl)-3-methylphenyl)(pyrrolidin-1-yl)methanone | 445 | +++++ | +++ |
| 57 | (2-(2-amino-3-cyclopentenylquinolin-6-yl)-3-methylphenyl)(pyrrolidin-1-yl)methanone | 398 | ++++ | ++ |
| 216 | 2-(2-amino-3-(2,6-dimethylmorpholino)quinolin-6-yl)-N-ethyl-3-methyl-N-propylbenzamide | 445 | +++++ | ++ |
| 217 | (2-(2-amino-3-(2-methyl-2-p-tolylmorpholino)quinolin-6-yl)-3-methylphenyl)(pyrrolidin-1-yl)methanone | 521 | ++++ | ++ |
| 218 | 3-morpholino-6-o-tolylquinolin-2-amine | 320 | +++ | + |
| 219 | 6-(2-chlorophenyl)-3-morpholinoquinolin-2-amine | 339.9 | +++ | + |
| 220 | 6-(2-fluorophenyl)-3-morpholinoquinolin-2-amine | 324 | ++ | + |

The present invention also provides methods for making compounds of Formulas I, 1-A, I-A-I and 1-B-I. In another embodiment of the invention, there is provided a method of making a compound of Formula I, the method comprising the steps of (a) reacting a compound 17

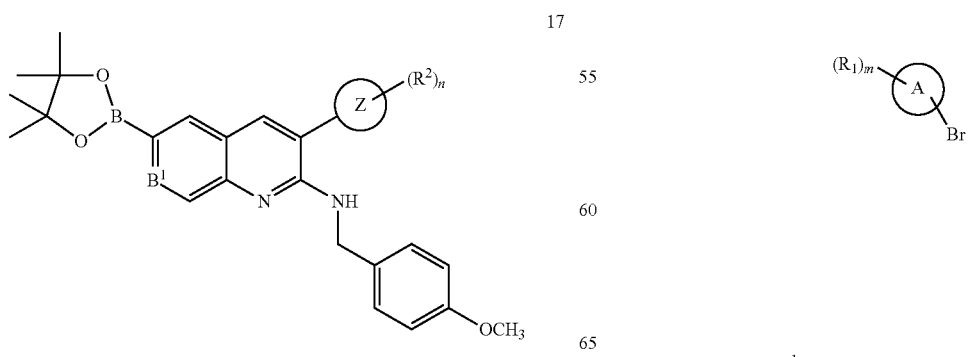

wherein $B^1$, ring Z, $R^2$ and n of Formula I are as defined herein, with a compound having the structure wherein ring A, $R^1$ and m are as defined herein to make a compound 18 of the formula

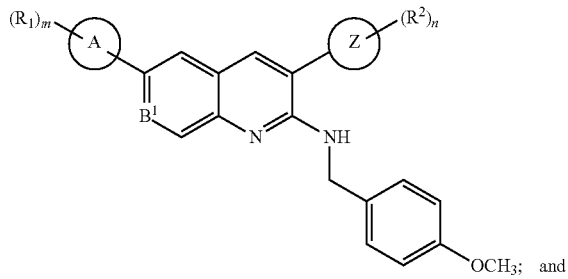

(b) deprotecting compound 18 to make a compound 19 of formula I

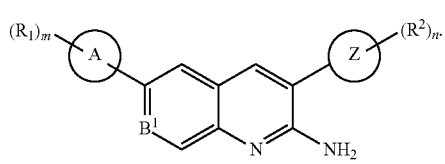

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3$^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, 2$^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, 2$^{nd}$ edition, Wiley-VCH, (1997); and L. Paquette, editor, Encyclopedia of Reagents for Organic Synthesis, John Wiley and Sons (1995).

Salts, including pharmaceutically acceptable salts, of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary and suitable salts, and their preparation, are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the H$^+$ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., Et$_2$O and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including CH$_3$CN; halogenated hydrocarbons, including CH$_2$Cl$_2$, CHCl$_3$ and CCl$_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, H$_2$SO$_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

The invention further encompasses "intermediate" compounds, including structures produced from the synthetic procedures described, whether isolated or generated in-situ and not isolated, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

The invention also provides new starting materials and/or intermediates, as well as processes for the preparation thereof. In select embodiments, such starting materials are used and reaction conditions so selected as to obtain the desired compound(s). Starting materials of the invention are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. While shown without respect to stereochemistry in Formulas I, I-A and I-B, the present invention includes such optical isomers and diastereomers, as well as the racemic and resolved, enantiomerically pure R and S stereoisomers, as well as other mixtures of R and S stereoisomers and pharmaceutically acceptable salts thereof.

The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of such compounds are expressly included in the present invention.

The compounds of the invention may also be represented in multiple tautomeric forms. Tautomers often exist in equilibrium with each other, and interconvert under environmental and physiological conditions. The compounds of the invention may also occur in cis- or trans- or E- or Z-double bond isomeric forms. The invention expressly includes all tautomeric forms of the compounds described herein.

All crystal forms of the compounds described herein are expressly included in the present invention.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{16}O$, $^{17}O$, $^{31}P$, $^{32}P$, $^{35}S$, $^{18}F$, and $^{36}Cl$.

Compounds of the present invention that contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detection. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

BIOLOGICAL EVALUATION

The compounds of the invention may be modified by appending appropriate functionalities to enhance selective biological properties. Surprisingly, the compounds of the present invention exhibit improved pharmacokinetics and pharmacodynamics, which relate, directly and indirectly, to the ability of the compound to be effective for its intended use. For example, the compounds have been found to possess favorable clearance and efflux properties, which readily lend themselves to projecting in-vivo PK and PD properties, which in turn assist in projection of therapeutic target coverage for the compounds and projected efficacious dosages via in-vivo absorption, distribution, metabolism and excretion properties. Increased biological penetration into a given biological compartment (e.g., blood, lymphatic system, central nervous system), increase oral availability, increase solubility to allow administration by injection and alter clearance, metabolism and/or rate of excretion are important factors for discovering which compound may be a useful drug and which may not.

Although the pharmacological properties of the compounds of the invention (Formulas I, 1-A, I-A-I and I-B-I) vary with structural change, in general, activity possessed by compounds of Formulas I, 1-A, I-A-I and 1-B-I may be demonstrated both in vitro as well as in vivo. The following exemplified pharmacological assays have been carried out with the compounds according to the invention, to assess and characterize the compound's ability to modulate BACE activity and to regulate the cleavage of amyloid beta precursor protein, thereby reducing or inhibiting the production of amyloid beta.

In Vitro Enzymatic BACE FRET (Fluorescence Resonance Energy Transfer) Assay (Enzyme Assay Data in Table 1)

The assay buffer used in this screen is 0.05 M acetate, pH 4.2, 10% DMSO final, 100 uM genapol (which is a nonionic detergent, below its Critical Micelle Concentration). The beta secretase enzyme (0.2 nM) is pre-incubated for one hour with inhibitors, typically in about 1 uL of DMSO according to a serial dilution, are added thereto. The assay is effectively started by the addition of FRET substrate (50 nM) and the combination is incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. Proteolytic cleavage of the FRET substrate releases quenching of fluorescence (excitation 488 nm and emission 425 nm).

Of the compounds tested, the in-vitro BACE FRET enzyme data for each of Examples 1-220, where available at the time of filing this application, is provided in Table 1. Data key for the in-vitro BACE FRET assay is as follows:

"+" means the compound example has an $IC_{50}$ value of >5.0 uM;

"++" means the compound example has an $IC_{50}$ value in the range from 1.01 uM-5.0 uM;

"+++" means the compound example has an $IC_{50}$ value in the range from 501 nM-1.0 uM;

"++++" means the compound example has an $IC_{50}$ value in the range from 100 nM-500 nM;

"+++++" means the compound example has an $IC_{50}$ value in the range less than 100 nM.

In Vitro BACE Cell-Based Assay:

The cell-based assay measures inhibition or reduction of Aβ40 in conditioned medium of test compound treated cells expressing amyloid precursor protein.

Cells stably expressing Amyloid Precursor Protein (APP) were plated at a density of 40K cells/well in 96 well plates (Costar). The cells were cultivated for 24 hours at 37° C. and 5% $CO_2$ in DMEM supplemented with 10% FBS. The test compounds were then added to cells in 10-point dose response concentrations with the starting concentration being either 100 μM or 10 μM. The compounds were diluted from stock solutions in DMSO and the final DMSO concentration of the test compounds on cells was 0.1%. After 24 h of incubation with the test compounds the supernatant conditioned media was collected and the Aβ 40 levels were determined using a sandwich ELISA. The $IC_{50}$ of the compound was calculated from the percent of control or percent inhibition of Aβ 40 as a function of the concentration of the test compound.

The sandwich ELISA to detect Aβ 40 was performed in 96 well microtiter plates, which were pre-treated with goat anti-rabbit IgG (Pierce). The capture and detecting antibody pair that were used to detect Aβ 40 from cell supernatants were affinity purified pAb40 (Biosource) and biotinylated 6E10 (Signet Labs Inc.), respectively. The optimal concentration for the pAb40 antibody was 3 μg/ml in Superblock/TBS (Pierce) that was supplemented with 0.05% Tween 20 (Sigma). Optimal concentration for the detection antibody 6E10-biotinylated was 0.5 μg/ml in Superblock/TBS (Pierce) that had been supplemented with 2% normal goat serum and 2% normal mouse serum.

Cellular supernatants were incubated with the capture antibody for 3 h at 4° C., followed by 3 wash steps in TBS-tween (0.05%). The detecting antibody incubation was for 2 h at 4° C., again followed by the wash steps as described previously. The final readout of the ELISA is Time-Resolved Fluorescence (counts per minute) using Delfia reagents Streptavidin-Europium and Enhancement solutions (Perkin Elmer) and the Victor 2 multilabel counter (Perkin Elmer).

Of the compounds tested, the cell based assay data for each of Examples 1-33 is provided in Table 1. Data key for the cell-based assay is as follows:

"+" means the compound example has an $IC_{50}$ value of >5.0 uM;

"++" means the compound example has an $IC_{50}$ value in the range from 1.01 uM-5.0 uM;

"+++" means the compound example has an $IC_{50}$ value in the range from 501 nM-1.0 uM;

"++++" means the compound example has an $IC_{50}$ value in the range from 100 nM-500 nM;

"+++++" means the compound example has an $IC_{50}$ value in the range less than 100 nM.

In Vivo Inhibition of Beta-Secretase

Several animal models, including mouse, rat, dog, and monkey, may be used to screen for inhibition of beta-secretase activity in vivo following administration of a test compound sample. Animals used in this invention can be wild type, transgenic, or gene knockout animals. For example, the Tg2576 mouse model, prepared and conducted as described in Hsiao et al., 1996, *Science* 274, 99-102, and other non-transgenic or gene knockout animals are useful to analyze in vivo inhibition of Amyloid beta peptide (Abeta) production in the presence of inhibitory test compounds. Generally, 2 to 18 month old Tg2576 mice, gene knockout mice or non-transgenic animals are administered test compounds formulated in vehicles, such as cyclodextran, phosphate buffers, hydroxypropyl methylcellulose or other suitable vehicles. One to twenty-four hours following the administration of compound, animals are sacrificed, and brains as well as cerebrospinal fluid (CSF) and plasma are removed for analysis of A-beta levels and drug or test compound concentrations (Dovey et al., 2001, *Journal of Neurochemistry*, 76, 173-181) Beginning at time 0, animals are administered by oral gavage, or other means of delivery such as intravenous injection, an inhibitory test compound of up to 100 mg/kg in a standard, conventional formulation, such as 2% hydroxypropyl methylcellulose, 1% Tween80. A separate group of animals receive 2% hydroxypropyl methylcellulose, 1% Tween80 alone, containing no test compound, and serve as a vehicle-control group. At the end of the test period, animals are sacrificed and brain tissues, plasma or cerebrospinal fluid are collected. Brains are either homogenized in 10 volumes (w/v) of 0.2% diethylamine (DEA) in 50 mM NaCl (Best et al., 2005, *Journal of Pharmacology and Experimental Therapeutics*, 313, 902-908), or in 10 volumes of 0.5% TritonX-100 in Tris-buffered saline (pH at about 7.6). Homogenates are centrifuged at 355,000 g, 4° C. for 30 minutes. CSF or brain supernatants are then analyzed for the presence of Abeta peptide by specific sandwich ELISA assays based on ECL (Electrochemiluminescence) technology. For example, rat Abeta40 is measured using biotinylated-4G8 (Signet) as a capture antibody and Fab40 (an in-house antibody specific to the C-terminal of Abeta40) as a detection antibody. For example, 4 hours after administration of 30 mg/kg oral dose of the test compound in 2% hydroxypropyl methylcellulose, 1% Tween80 (pH2.2) to 200 g male Sprague Dawley rats, Abeta peptide levels are measured for reduction by X % and Y % in cerebrospinal fluid and brain, respectively, when compared to the levels measured in the vehicle-treated or control mice.

Actual vehicles used: Oral: 2% HPMC, 1% Tween80, pH 2.2
    IV: 5% EtOH, 45% Propylene glycol in 5% Dextrose The compounds of the invention may be shown to reduce the formation and/or deposition of A-beta peptide in the brain or in the cerebrospinal fluid of a mouse or rat.

Indications

Accordingly, compounds of the invention are useful for, but not limited to, the prevention or treatment of beta-secretase related diseases, including Alzheimer's disease. The compounds of the invention have the ability to modulate the activity of beta secretase enzyme, thereby regulating the production of amyloid beta (Abeta peptide) and reducing the formation and deposition of Abeta peptide and/or plaque on the brain. In one embodiment of the invention, there is provided a method of treating a disorder related to a beta-secretase enzyme in a subject, the method comprising administering to the subject an effective dosage amount of a compound of Formulas I, 1-A, I-A-I and 1-B-I. In another embodiment, there is provided a method of reducing production of amyloid beta, and of reducing plaque formation. In another embodiment, there is provided a method for the treatment, prevention or amelioration of a disease or disorder characterized by the elevated beta-amyloid deposits or beta-amyloid levels in a subject, the method comprising administering to the subject a therapeutically effective amount of a compound according to any of Formulas I, 1-A, I-A-I and 1-B-I. In yet another embodiment, the invention provides a method of treating Alzheimer's disease, cognitive impairment including mild, moderate and/or severe, Down's Syndrome, cognitive decline, senile dementia, cerebral amyloid angiopathy or a neurodegenerative disorder.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations and Method of Use

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating neurological disorders and beta-secretase mediated diseases with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, and even more advantageously between about 0.1 and about 10 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable carrier, which includes diluents, excipients and the like as described herein. A pharmaceutical composition of the invention may comprise an effective amount of a compound of the invention or an effective dosage amount of a compound of the invention. An effective dosage amount of a compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multidose pharmaceutical composition, such as powders, liquids and the like, in which an effective amount of the compound is administered by administering a portion of the composition. Alternatively, a pharmaceutical composition in which two or more unit dosages, such as in tablets, capsules and the like, are required to administer an effective amount of the compound may be administered in less than an effective amount for one or more periods of time, for example to ascertain the effective dose for an individual subject, to desensitize an individual subject to potential side effects, to permit effective dosing readjustment or depletion of one or more other therapeutics administered to an individual subject, and/or the like.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, advantageously from about 1 to 500 mg, and typically from about 5 to 150 mg. A suitable daily dose for a human or other mammal may vary widely depending on the condition of the patient and other factors, but, once again, can be determined using routine methods and practices.

For therapeutic purposes, the active compounds of this invention are ordinarily combined with one or more adjuvants or other "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, and preferably from about 0.1 to about 10 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents. Accordingly, in yet another embodiment of the present invention, there is provided a method of manufacturing a medicament, the method comprising combining an amount of a compound according to Formulas I, 1-A, I-A-I and 1-B-I with a pharmaceutically acceptable carrier to manufacture the medicament.

In yet another embodiment, the invention provides a method of manufacturing a medicament for the treatment of Alzheimer's disease, the method comprising combining an amount of a compound according to Formulas I, 1-A, I-A-I and 1-B-I with a pharmaceutically acceptable carrier to manufacture the medicament.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of beta-secretase, gamma-secretase and/or other reagents known in influence the formation and/or deposition of amyloid beta, otherwise responsible for the formation of plaque on the brain.

If formulated as a fixed dose, such combination products employ the compounds of this invention within the accepted dosage ranges. Compounds of Formulas I, I-A and I-B may also be administered sequentially with known anti-inflammatory agents when a combination formulation is inappropriate. The invention is not limited in the sequence of administration; compounds of the invention may be administered either prior to, simultaneous with or after administration of the known anti-inflammatory agent.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:

1. A compound, or a stereoisomer or pharmaceutically acceptable salt thereof, having a Formula I-B-I

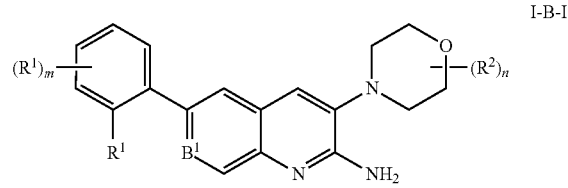

I-B-I wherein
$B^1$ is —CF, —CCH$_3$ or CH;
each $R^1$, independently, is halo, haloalkyl, CN, OH, NO$_2$, NH$_2$, acetyl, C$_{1-6}$-alkyl, C$_{2-6}$-alkenyl, C$_{2-6}$-alkynyl, C$_{3-7}$-cycloalkyl, C$_{4-7}$-cycloalkenyl, C$_{1-6}$-alkylamino-, C$_{1-6}$-dialkylamino-, C$_{1-6}$-alkoxyl, C$_{1-6}$-thioalkoxyl, —C(O)—R$^3$, —C(O)NHR$^3$, —C(O)OR$^3$ or —C(O)NR$^a$R$^b$, wherein R$^a$ is H or C$_{1-6}$alkyl and R$^b$ is R$^3$, alternatively, R$^a$ and R$^b$ taken together with the nitrogen atom to which they are attached form a 4-7 membered monocyclic heterocycle, optionally substituted with 1-3 substituents of R$^3$; or
R$^1$ is a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^3$;

each $R^2$ independently, is F, Cl, $CF_3$, $OCF_3$, $C_{1-6}$-alkyl, CN, OH, —$OC_{1-6}$-alkyl, —$OCF_3$, —$NH_2$, $NHCH_3$ or —$C(O)CH_3$;

each $R^3$, independently, is halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

m is 0 or 1; and n is 0 or 1.

2. The compound of claim 1, or a stereoisomer or pharmaceutically acceptable salt thereof, selected from (2-(2-amino-3-morpholinoquinolin-6-yl)-3-methylphenyl)(pyrrolidin-1-yl)methanone;
(2-(2-amino-3-morpholinoquinolin-6-yl)-3-methylphenyl)(piperidin-1-yl)methanone;
(2-(2-amino-3-morpholinoquinolin-6-yl)-3-methylphenyl)(morpholino)methanone;
ethyl 2-(2-amino-3-morpholinoquinolin-6-yl)-3-methylbenzoate;
(2-(2-amino-3-morpholinoquinolin-6-yl)-3-methylphenyl)(2-propylpyrrolidin-1-yl)methanone;
(2-(2-amino-3-morpholinoquinolin-6-yl)-3-methylphenyl)(2-tert-butylpyrrolidin-1-yl)methanone;
(2-(2-amino-3-morpholinoquinolin-6-yl)-3-methylphenyl)(2-ethylpyrrolidin-1-yl)methanone;
(2-(2-amino-3-morpholinoquinolin-6-yl)-3-methylphenyl)(2-isopropylpyrrolidin-1-yl)methanone;
(2-(2-amino-3-morpholinoquinolin-6-yl)-3-methylphenyl)(2-methylpyrrolidin-1-yl)methanone;
(2-(2-amino-3-morpholinoquinolin-6-yl)-3-methylphenyl) ((1R,4S)-2-azabicyclo[2.2.1]heptan-2-yl)methanone;
(R)-(2-(2-amino-3-morpholinoquinolin-6-yl)-3-methylphenyl)(3-fluoropyrrolidin-1-yl)methanone;
(R)-(2-(2-amino-3-morpholinoquinolin-6-yl)-3-methylphenyl)(2-(methoxymethyl)pyrrolidin-1-yl)methanone;
2-(2-amino-3-morpholinoquinolin-6-yl)-N-(2-methoxyethyl)-N,3-dimethylbenzamide;
(2-(2-amino-3-morpholinoquinolin-6-yl)-3-methylphenyl)(4-methoxypiperidin-1-yl)methanone;
(2-(2-amino-3-morpholinoquinolin-6-yl)-3-methylphenyl)(4-(methoxymethyl)piperidin-1-yl)methanone;
(2-(2-amino-3-morpholinoquinolin-6-yl)-3-methylphenyl)(4-(ethoxymethyl)piperidin-1-yl)methanone;
(2-(2-amino-3-morpholinoquinolin-6-yl)-3-methylphenyl)(4-(2-methoxyethyl)piperidin-1-yl)methanone;
(2-(2-amino-3-morpholinoquinolin-6-yl)-3-methylphenyl)(4-ethoxypiperidin-1-yl)methanone;
(R)-(2-(2-amino-3-morpholinoquinolin-6-yl)-3-methylphenyl)(3-methylpiperidin-1-yl)methanone;
(2-(2-amino-3-morpholinoquinolin-6-yl)-3-methylphenyl)(4-propylpiperidin-1-yl)methanone;
(2-(2-amino-3-morpholinoquinolin-6-yl)-3-methylphenyl)(2-propylpiperidin-1-yl)methanone;
(2-(2-amino-3-morpholinoquinolin-6-yl)-3-methylphenyl)(4-methylpiperidin-1-yl)methanone;
(2-(2-amino-3-morpholinoquinolin-6-yl)-3-methylphenyl)(2-ethylpiperidin-1-yl)methanone;
(2-(2-amino-3-morpholinoquinolin-6-yl)-3-methylphenyl)(3-methoxypiperidin-1-yl)methanone;
(2-(2-amino-3-morpholinoquinolin-6-yl)-3-methylphenyl)(2-(2-methoxyethyl)piperidin-1-yl)methanone;
(2-(2-amino-3-morpholinoquinolin-6-yl)-3-methylphenyl)((2S,6R)-2,6-dimethylpiperidin-1-yl)methanone;
(2-(2-amino-3-morpholinoquinolin-6-yl)-3-methylphenyl)(3-ethoxypiperidin-1-yl)methanone;
(2-(2-amino-3-morpholinoquinolin-6-yl)-3-methylphenyl)(3,3-dimethylpiperidin-1-yl)methanone;
(2-(2-amino-3-morpholinoquinolin-6-yl)-3-methylphenyl)(2-methylpiperidin-1-yl)methanone;
(2-(2-amino-3-morpholinoquinolin-6-yl)-3-methylphenyl)(3,5-dimethylpiperidin-1-yl)methanone;
(2-(2-amino-3-morpholinoquinolin-6-yl)-3-methylphenyl)(thiazolidin-3-yl)methanonel;
(2-(2-amino-3-morpholinoquinolin-6-yl)-3-methylphenyl)(2,5-dihydro-1H-pyrrol-1-yl)methanone;
(2-(2-amino-3-morpholinoquinolin-6-yl)-3-methylphenyl)(thiomorpholino)methanone;
2-(2-amino-3-morpholinoquinolin-6-yl)-N-cyclopentyl-N,3-dimethylbenzamide;
(2-(2-amino-3-morpholinoquinolin-6-yl)-3-methylphenyl)(4-tert-butylpiperidin-1-yl)methanone;
(S)-(2-(2-amino-3-morpholinoquinolin-6-yl)-3-methylphenyl)(2-(trifluoromethyl)pyrrolidin-1-yl)methanone;
(2-(2-amino-3-morpholinoquinolin-6-yl)-3-methylphenyl)(4-fluoropiperidin-1-yl)methanone;
(2-(2-amino-3-morpholinoquinolin-6-yl)-3-methylphenyl)(3-(trifluoromethyl)pyrrolidin-1-yl)methanone;
(2-(2-amino-3-morpholinoquinolin-6-yl)-3-methylphenyl)(3,3-difluoropiperidin-1-yl)methanone;
(2-(2-amino-3-morpholinoquinolin-6-yl)-3-methylphenyl)(3,3-difluoropyrrolidin-1-yl)methanone;
(2-(2-amino-3-morpholinoquinolin-6-yl)-3-methylphenyl)(3,3-difluoroazetidin-1-yl)methanone;
2-(2-amino-3-morpholinoquinolin-6-yl)-N,3-dimethyl-N-(2,2,2-trifluoroethyl)benzamide;
(R)-(2-(2-amino-3-morpholinoquinolin-6-yl)-3-methylphenyl)(3-methylpyrrolidin-1-yl)methanone;
2-(2-amino-3-morpholinoquinolin-6-yl)-N,N-diethyl-3-methylbenzamide;
(2-(2-amino-3-morpholinoquinolin-6-yl)-3-methylphenyl)(azetidin-1-yl)methanone;
2-(2-amino-3-morpholinoquinolin-6-yl)-N-isobutyl-N,3-dimethylbenzamide;
2-(2-amino-3-morpholinoquinolin-6-yl)-N-ethyl-3-methyl-N-propylbenzamide;

2-(2-amino-3-morpholinoquinolin-6-yl)-N-isopropyl-3-methyl-N-propylbenzamide;
2-(2-amino-3-morpholinoquinolin-6-yl)-N-cyclopropyl-N-ethyl-3-methylbenzamide;
2-(2-amino-3-morpholinoquinolin-6-yl)-N,3-dimethyl-N-(prop-2-ynyl)benzamide;
(2-(2-amino-3-morpholinoquinolin-6-yl)-3-methylphenyl)(4,4-difluoropiperidin-1-yl)methanone;
2-(2-amino-3-morpholinoquinolin-6-yl)-N,3-dimethyl-N-propylbenzamide;
2-(2-amino-3-morpholinoquinolin-6-yl)-N-(cyclopropylmethyl)-3-methyl-N-propylbenzamide;
2-(2-amino-3-morpholinoquinolin-6-yl)-N-cyclohexyl-N,3-dimethylbenzamide;
2-(2-amino-3-morpholinoquinolin-6-yl)-N-cyclohexyl-N-ethyl-3-methylbenzamide;
(2-(2-amino-3-morpholinoquinolin-6-yl)-3-methylphenyl)(2-(methylthio)-4,5-dihydro-1H-imidazol-1-yl)methanone;
(2-(2-amino-3-morpholinoquinolin-6-yl)-3-methylphenyl)(3-methylpiperidin-1-yl)methanone;
N,N-diallyl-2-(2-amino-3-morpholinoquinolin-6-yl)-3-methylbenzamide;
2-(2-amino-3-morpholinoquinolin-6-yl)-N-butyl-N,3-dimethylbenzamide;
2-(2-amino-3-morpholinoquinolin-6-yl)-N-butyl-N-ethyl-3-methylbenzamide;
2-(2-amino-3-morpholinoquinolin-6-yl)-N-isopentyl-N,3-dimethylbenzamide;
2-(2-amino-3-morpholinoquinolin-6-yl)-N,3-dimethyl-N-(pentan-2-yl)benzamide;
2-(2-amino-3-morpholinoquinolin-6-yl)-N-ethyl-N,3-dimethylbenzamide;
2-(2-amino-3-morpholinoquinolin-6-yl)-N,3-dimethyl-N-(4-methylcyclohexyl)benzamide;
2-(2-amino-3-morpholinoquinolin-6-yl)-N-tert-butyl-N,3-dimethylbenzamide;
(2-(2-amino-3-morpholinoquinolin-6-yl)-3-methylphenyl)(2,6-dimethylpiperidin-1-yl)methanone;
(2-(2-amino-3-morpholinoquinolin-6-yl)-3-methylphenyl)(2,5-dimethyl-2,5-dihydro-1H-pyrrol-1-yl)methanone;
2-(2-amino-3-morpholinoquinolin-6-yl)-N,3-dimethyl-N-phenylbenzamide;
2-(2-amino-3-morpholinoquinolin-6-yl)-3-methyl-N-phenylbenzamide;
(2-(2-amino-3-morpholinoquinolin-6-yl)-5-fluorophenyl)(azetidin-1-yl)methanone;
ethyl 2-(2-amino-3-morpholinoquinolin-6-yl)-5-fluoro-3-methylbenzoate;
(R)-(2-(2-amino-3-morpholinoquinolin-6-yl)-5-fluoro-3-methylphenyl)(3-fluoropyrrolidin-1-yl)methanone;
2-(2-amino-3-morpholinoquinolin-6-yl)-N,3-dimethyl-N-p-tolylbenzamide;
2-(2-amino-3-morpholinoquinolin-6-yl)-N-(4-methoxyphenyl)-N,3-dimethylbenzamide;
(R)-2-(2-amino-3-morpholinoquinolin-6-yl)-N,3-dimethyl-N-(1-phenylethyl)benzamide;
2-(2-amino-3-morpholinoquinolin-6-yl)-N,N,3-trimethylbenzamide;
2-(2-amino-3-morpholinoquinolin-6-yl)-N,3-dimethyl-N-(naphthalen-1-ylmethyl)benzamide;
2-(2-amino-3-morpholinoquinolin-6-yl)-N-benzyl-N,3-dimethylbenzamide;
2-(2-amino-3-morpholinoquinolin-6-yl)-N,3-dimethyl-N-phenethylbenzamide;
2-(2-amino-3-morpholinoquinolin-6-yl)-N-(4-fluorophenyl)-N,3-dimethylbenzamide;
2-(2-amino-3-morpholinoquinolin-6-yl)-N-(2-methoxyphenyl)-N,3-dimethylbenzamide;
(2-(2-amino-7-fluoro-3-morpholinoquinolin-6-yl)phenyl)(pyrrolidin-1-yl)methanone;
(2-(2-amino-3-morpholinoquinolin-6-yl)-6-chlorophenyl)(pyrrolidin-1-yl)methanone;
(2-(2-amino-3-morpholinoquinolin-6-yl)-6-fluorophenyl)(pyrrolidin-1-yl)methanone;
(2-(2-amino-3-morpholinoquinolin-6-yl)-3-chlorophenyl)(piperidin-1-yl)methanone;
(2-(2-amino-3-morpholinoquinolin-6-yl)-3-chlorophenyl)(morpholino)methanone;
cyclopentyl 2-(2-amino-3-morpholinoquinolin-6-yl)benzoate;
cyclopentyl 2-(2-amino-3-morpholinoquinolin-6-yl)-3-methylbenzoate;
(2-(2-amino-3-morpholinoquinolin-6-yl)phenyl)(tetrahydro-2H-pyran-4-yl)methanone;
(2-(2-amino-3-morpholinoquinolin-6-yl)phenyl)(tetrahydro-2H-pyran-4-yl)methanol;
3-morpholino-6-(2-((tetrahydro-2H-pyran-4-yl)methyl)phenyl)quinolin-2-amine;
(2-(2-amino-7-fluoro-3-morpholinoquinolin-6-yl)-3-methylphenyl)(pyrrolidin-1-yl)methanone;
(2-(2-amino-7-fluoro-3-morpholinoquinolin-6-yl)-3-methylphenyl)(pyrrolidin-1-yl)methanone;
(2-(2-amino-3-morpholinoquinolin-6-yl)-5-chlorophenyl)(pyrrolidin-1-yl)methanone;
(2-(2-amino-3-morpholinoquinolin-6-yl)-3-fluorophenyl)(pyrrolidin-1-yl)methanone;
(2-(2-amino-3-morpholinoquinolin-6-yl)phenyl)(cyclopentyl)methanone;
(2-(2-amino-3-morpholinoquinolin-6-yl)-4-methylphenyl)(pyrrolidin-1-yl)methanone;
(2-(2-amino-3-morpholinoquinolin-6-yl)phenyl)(phenyl)methanone;
(2-(2-amino-3-morpholinoquinolin-6-yl)phenyl)(cyclohexyl)methanone;
1-(2-(2-amino-3-morpholinoquinolin-6-yl)phenyl)-3,3-dimethylbutan-1-one;
(2-(2-amino-3-morpholinoquinolin-6-yl)-4-chlorophenyl)(pyrrolidin-1-yl)methanone;
(2-(2-amino-3-morpholinoquinolin-6-yl)-3-(trifluoromethyl)phenyl)(pyrrolidin-1-yl)methanone;
1-(2-(2-amino-3-morpholinoquinolin-6-yl)phenyl)-2-cyclopentylethanone;
(2-(2-amino-3-morpholinoquinolin-6-yl)-3-methylphenyl)(o-tolyl)methanone;
(2-(2-amino-3-morpholinoquinolin-6-yl)-3-methylphenyl)(phenyl)methanone;
(2-(2-amino-3-morpholinoquinolin-6-yl)-3-methylphenyl)(pyridin-2-yl)methanone;
(2-(2-amino-3-morpholinoquinolin-6-yl)-3-methylphenyl)(thiazol-2-yl)methanone;
(2-(2-amino-3-morpholinoquinolin-6-yl)-3-methylphenyl)(2-methoxyphenyl)methanone;
(2-(2-amino-3-morpholinoquinolin-6-yl)-3-methylphenyl)(3-chloropyridin-2-yl)methanone;
6-(2-(3,4-dihydroisoquinolin-1-yl)-6-methylphenyl)-3-morpholinoquinolin-2-amine;
(2-(2-amino-3-morpholinoquinolin-6-yl)-3-methylphenyl)(tetrahydrofuran-2-yl)methanone;
6-(2-(imino(2-methoxyphenyl)methyl)-6-methylphenyl)-3-morpholinoquinolin-2-amine;

6-(2-((1H-imidazol-1-yl)(phenyl)methyl)-6-methylphenyl)-3-morpholinoquinolin-2-amine;
6-(2-methyl-6-(phenyl(pyrrolidin-1-yl)methyl)phenyl)-3-morpholinoquinolin-2-amine;
6-(2-methyl-6-(1,2,3,4-tetrahydroisoquinolin-1-yl)phenyl)-3-morpholinoquinolin-2-amine;
6-(2-(3,3-dimethylbut-1-ynyl)-6-methylphenyl)-3-morpholinoquinolin-2-amine;
2-(2-amino-3-morpholinoquinolin-6-yl)-N,3-dimethyl-N-neopentylbenzamide;
6-(2-(3,3-dimethylbut-1-ynyl)phenyl)-3-morpholinoquinolin-2-amine;
(2-(2-amino-3-morpholinoquinolin-6-yl)-3-chlorophenyl)(pyrrolidin-1-yl)methanone;
(2-(2-amino-3-morpholinoquinolin-6-yl)-3-methylphenyl)(2,2-dimethylmorpholino)methanone;
(2-(2-amino-3-morpholinoquinolin-6-yl)-3-(3,3-dimethylbut-1-ynyl)phenyl)(pyrrolidin-1-yl)methanone;
(2-(2-amino-3-morpholinoquinolin-6-yl)-3-(3,3-dimethylbutyl)phenyl)(pyrrolidin-1-yl)methanone;
1-(2-(2-amino-3-morpholinoquinolin-6-yl)-3-(pyrrolidine-1-carbonyl)phenyl)-3,3-dimethylbutan-1-one;
(2-(2-amino-3-morpholinoquinolin-6-yl)-3-(phenylethynyl)phenyl)(pyrrolidin-1-yl)methanone;
(2-(2-amino-3-morpholinoquinolin-6-yl)-3-phenethylphenyl)(pyrrolidin-1-yl)methanone;
S)-(2-(2-amino-3-morpholinoquinolin-6-yl)-3-(3,3-dimethylbutyl)phenyl) (3-fluoropyrrolidin-1-yl)methanone;
(2-(2-amino-3-morpholinoquinolin-6-yl)-3-(3,3-dimethylbuyl)phenyl)(morpholino)methanone;
(2-(2-amino-3-morpholinoquinolin-6-yl)-3-(3,3-dimethylbutyl)phenyl)(azetidin-1-yl)methanone;
(S)-(2-(2-amino-3-morpholinoquinolin-6-yl)-3-(3,3-dimethylbutyl)phenyl)(3-fluoropyrrolidin-1-yl)methanone;
(2-(2-amino-3-morpholinoquinolin-6-yl)-3-(cyclohexylethynyl)phenyl)(pyrrolidin-1-yl)methanone;
(2-(2-amino-3-morpholinoquinolin-6-yl)-3-(2-cyclohexylethyl)phenyl)(pyrrolidin-1-yl)methanone;
4-(2-(2-amino-3-morpholinoquinolin-6-yl)-3-methylphenyl)morpholin-3-one;
N-(2-(2-amino-3-morpholinoquinolin-6-yl)-3-methylphenyl)-N,3,3-trimethylbutanamide;
6-(2-methyl-6-(phenylamino)phenyl)-3-morpholinoquinolin-2-amine;
4-(2-(2-amino-3-morpholinoquinolin-6-yl)-3-methylphenyl)-6,6-dimethylmorpholin-3-one;
3-morpholino-6-(2-(neopentyloxy)phenyl)quinolin-2-amine;
6-(2-methyl-6-(neopentyloxy)phenyl)-3-morpholinoquinolin-2-amine;
6-(2-(benzyloxy)phenyl)-3-morpholinoquinolin-2-amine;
6-(2-(benzyloxy)-6-methylphenyl)-3-morpholinoquinolin-2-amine;
6-(2-methyl-6-(tetrahydrofuran-3-yloxy)phenyl)-3-morpholinoquinolin-2-amine;
6-(2-(2-isopropoxyethoxy)-6-methylphenyl)-3-morpholinoquinolin-2-amine;
6-(2-methyl-6-phenoxyphenyl)-3-morpholinoquinolin-2-amine;
6-(2-(3,3-dimethylbutyl)-6-methylphenyl)-3-morpholinoquinolin-2-amine;
(2-(2-amino-3-morpholinoquinolin-6-yl)-3-methylphenyl)(m-tolyl)methanone;
(2-(2-amino-3-morpholinoquinolin-6-yl)-3-methylphenyl)(3-methoxypyridin-2-yl)methanone;
(2-(2-amino-3-morpholinoquinolin-6-yl)-3-methylphenyl)(3-methylpyridin-2-yl)methanone;
(E)-(2-(2-amino-3-morpholinoquinolin-6-yl)-3-methylphenyl)(phenyl)methanone oxime;
(Z)-(2-(2-amino-3-morpholinoquinolin-6-yl)-3-methylphenyl)(phenyl)methanone oxime;
E)-(2-(2-amino-3-morpholinoquinolin-6-yl)-3-methylphenyl)(phenyl)methanone O-methyl oxime;
(Z)-(2-(2-amino-3-morpholinoquinolin-6-yl)-3-methylphenyl)(phenyl)methanone O-methyl oxime;
(3-((1,3-dioxolan-2-yl)methyl)-2-(2-amino-3-morpholinoquinolin-6-yl)phenyl)(pyrrolidin-1-yl)methanone;
6-(2-(amino(phenyl)methyl)-6-methylphenyl)-3-morpholinoquinolin-2-amine;
6-(2-(amino(o-tolyl)methyl)-6-methylphenyl)-3-morpholinoquinolin-2-amine;
6-(2-(amino(2-methoxyphenyl)methyl)-6-methylphenyl)-3-morpholinoquinolin-2-amine;
6-(2-(amino(pyridin-2-yl)methyl)-6-methylphenyl)-3-morpholinoquinolin-2-amine;
6-(2-(amino(3-chloropyridin-2-yl)methyl)-6-methylphenyl)-3-morpholinoquinolin-2-amine;
6-(2-(amino(3-methoxypyridin-2-yl)methyl)-6-methylphenyl)-3-morpholinoquinolin-2-amine;
6-(2-(amino(3-methylpyridin-2-yl)methyl)-6-methylphenyl)-3-morpholinoquinolin-2-amine;
(2-(2-amino-3-morpholinoquinolin-6-yl)-3-methylphenyl)(phenyl)methanol;
6-(2-benzyl-6-methylphenyl)-3-morpholinoquinolin-2-amine;
3-(2-(2-amino-3-morpholinoquinolin-6-yl)-3-methylbenzyl)benzonitrile;
6-(2-(4-fluorobenzyl)-6-methylphenyl)-3-morpholinoquinolin-2-amine;
6-(2-(2-fluorobenzyl)-6-methylphenyl)-3-morpholinoquinolin-2-amine;
6-(2-(3-methoxybenzyl)-6-methylphenyl)-3-morpholinoquinolin-2-amine;
6-(2-(4-chloro-1H-pyrazol-1-yl)-6-methylphenyl)-3-morpholinoquinolin-2-amine;
6-(2-(4-chloro-3-methyl-1H-pyrazol-1-yl)-6-methylphenyl)-3-morpholinoquinolin-2-amine;
3-morpholino-6-(2-(4,5,6,7-tetrahydro-1H-indazol-1-yl)phenyl)quinolin-2-amine;
6-(2-methyl-6-(5-methyloxazol-2-yl)phenyl)-3-morpholinoquinolin-2-amine;
6-(2-methyl-6-(4-methyloxazol-2-yl)phenyl)-3-morpholinoquinolin-2-amine;
6-(2-(imidazo[1,5-a]pyridin-3-yl)-6-methylphenyl)-3-morpholinoquinolin-2-amine;
(2-(2-amino-3-morpholinoquinolin-6-yl)-5-fluoro-3-methylphenyl)(pyrrolidin-1-yl)methanone;
(2-(2-amino-3-morpholinoquinolin-6-yl)-3-methylphenyl)(1H-indol-1-yl)methanone;
6-(2-((2-chloro-5-(trifluoromethyl)phenoxy)methyl)-6-methylphenyl)-3-morpholinoquinolin-2-amine;
6-(3-methyl-3'-(trifluoromethyl)biphenyl-2-yl)-3-morpholinoquinolin-2-amine;
(R)-(2-(2-amino-3-(3-methylmorpholino)quinolin-6-yl)-3-methylphenyl)(pyrrolidin-1-yl)methanone;
(2-(2-amino-3-(2,3-dimethylmorpholino)quinolin-6-yl)-3-methylphenyl)(pyrrolidin-1-yl)methanone;
(S)-(2-(2-amino-3-(3-methylmorpholino)quinolin-6-yl)-3-methylphenyl)(pyrrolidin-1-yl)methanone;
6-(2-([1,2,4]triazolo[4,3-a]pyridin-3-yl)-6-methylphenyl)-3-morpholinoquinolin-2-amine;

(2-(2-amino-3-morpholinoquinolin-6-yl)-3-methylphenyl)(pyrimidin-4-yl)methanone;
(2-(2-amino-3-morpholinoquinolin-6-yl)-3-methylphenyl)(pyrazin-2-yl)methanol;
6-(2-methyl-6-(pyrazin-2-ylmethyl)phenyl)-3-morpholinoquinolin-2-amine;
(2-(2-amino-3-(2-isobutylmorpholino)quinolin-6-yl)-3-methylphenyl)(pyrrolidin-1-yl)methanone;
(2-(2-amino-3-(2-(2-methoxyethyl)morpholino)quinolin-6-yl)-3-methylphenyl)(pyrrolidin-1-yl)methanone;
(2-(2-amino-3-(2,2-dimethylmorpholino)quinolin-6-yl)-3-methylphenyl)(pyrrolidin-1-yl)methanone;
2-(2-amino-3-(2,6-dimethylmorpholin in))-N-ethyl-3-methyl-N-propylbenzamide;
(2-(2-amino-3-(2-methyl-2-p-tolylmorpholino)quinolin-6-hy)-3-methylphenyl)(pyrrolidin-1-yl)methanone;
3-morpholino-6-o-tolylquinolin-2-amine;
6-(2-chlorophenyl)-3-morpholinoquinolin-2-amine;
3-morpholino-6-o-tolylquinolin-2-amine; and
6-(2-fluorophenyl)-3-morpholinoquinolin-2-amine.

3. A pharmaceutical composition comprising a compound according to claim 1 and a pharmaceutically acceptable excipient.

* * * * *